(12) United States Patent
Berlin et al.

(10) Patent No.: US 9,795,691 B2
(45) Date of Patent: Oct. 24, 2017

(54) CHEMICALLY-LINKED NANOPARTICLES

(71) Applicant: City of Hope, Duarte, CA (US)

(72) Inventors: Jacob Berlin, Monrovia, CA (US); Desiree van Haute, Duarte, CA (US)

(73) Assignee: City of Hope, Duarte, CA (US)

( * ) Notice: Subject to any disclaimer, the term of this patent is extended or adjusted under 35 U.S.C. 154(b) by 0 days.

(21) Appl. No.: 14/313,736

(22) Filed: Jun. 24, 2014

(65) Prior Publication Data

US 2014/0377175 A1    Dec. 25, 2014

Related U.S. Application Data

(60) Provisional application No. 61/838,597, filed on Jun. 24, 2013.

(51) Int. Cl.
*A61K 49/00* (2006.01)
*A61K 47/48* (2006.01)

(52) U.S. Cl.
CPC ...... *A61K 49/0002* (2013.01); *A61K 47/4893* (2013.01); *Y10T 428/2982* (2015.01)

(58) Field of Classification Search
CPC ............ A61K 47/4893; A61K 49/0002; Y10T 428/2982
See application file for complete search history.

(56) References Cited

U.S. PATENT DOCUMENTS

| | | | |
|---|---|---|---|
| 4,861,760 A | 8/1989 | Mazuel et al. | |
| 4,911,920 A | 3/1990 | Jani et al. | |
| 5,212,162 A | 5/1993 | Missel et al. | |
| 5,403,841 A | 4/1995 | Lang et al. | |
| 2012/0269721 A1* | 10/2012 | Weng et al. | 424/1.11 |
| 2013/0023714 A1* | 1/2013 | Johnston | A61K 9/0009 600/1 |

OTHER PUBLICATIONS

Boal, A.K. et al. (Apr. 13, 2000). "Self-Assembly of Nanoparticles into Structured Spherical and Network Aggregates" *Letters to Nature* 404:746-748.
Elghanian, R. et al. (Aug. 22, 1997). "Selective Colorimetric Detection of polynucleotides Based on the Distance-Dependent Optical Properties of Gold Nanoparticles," *Science* 277:1078-1081.
Hossain, M.K. et al. (2008). "SPR and SERS Characteristics of Gold Nanoaggregates with Different Morphologies," *Applied Physics B* 93(1):165-170.
Hussain, I. et al. (2006). "Formation of Spherical Nanostructures by the Controlled Aggregation of Gold Colloids," *Langmuir* 22(7):2938-2941.
Keren, S. et al. (2008). "Noninvasive Molecular Imaging of Small Living Subjects Using Raman Spectroscopy," *PNAS* 105(15):5844-5849.
Klajn, R. et al. (Apr. 13, 2007). "Plastic and moldable metals by self-assembly of sticky nanoparticle aggregates," *Science* 316(5822):261-264.
Kneipp, J. et al. (Oct. 2006). "In vivo molecular probing of cellular compartments with gold nanoparticles and nanoaggregates," *Nano Lett* 6(10):2225-2231.
Lee, K. et al. (Mar. 22, 2011, e-published Feb. 11, 2011). "DNA-gold nanoparticle reversible networks grown on cell surface marker sites: application in diagnostic," *ACS Nano* 5(3):2109-2117.
Maye, M.M. et al. (2005, e-published Jan. 11, 2005). "Mediator-Template Assembly of Nanoparticles," *J Am Chem Soc* 127:1519-152.
Niles, A.L. et al. (Jun. 11, 2009). "In vitro viability and cytotoxicity testing and same-well multi-parametric combinations for high throughput screening," *Curr Chem Genomics* 3:33-41.
Schwartzberg, A.M. et al. (2004, e-published Nov. 17, 2004). "Unique Gold Nanoparticle Aggregates as a Highly Active Surface-Enhanced Raman Scattering Substrate," *J Phys Chem B* 108(50):19191-19197.
Stiles, P.L. et al. (2008, e-published Mar. 18, 2008). "Surface-Enhanced Raman Spectroscopy," *Annu Rev Anal Chem* 1(1):601-626.
Storhoff, J.J. et al. (2000). "What Controls the Optical Properties of DNA-Linked Gold Nanoparticle Assemblies?" *J Am Chem Soc* 122(19):4640-4650.
Tam, J.M. et al. (Apr. 27, 2010). "Controlled assembly of biodegradable plasmonic nanoclusters for near-infrared imaging and therapeutic applications," *ACS Nano* 4(4):2178-2184.
Al-Zaki, A. et al. (Jan. 28, 2014, e-published Jan. 7, 2014). "Gold-loaded polymeric micelles for computed tomography-guided radiation therapy treatment and radiosensitization," *ACS Nano* 8(1):104-112.
Chou, L.Y. et al. (Feb. 2014, e-published Jan. 26, 2014). "DNA assembly of nanoparticle superstructures for controlled biological delivery and elimination," *Nat Nanotechnol* 9(2):148-155.
Guo, Z. et al. (2010). "Effects of iron oxide nanoparticles on polyvinyl alcohol: interfacial layer and bulk nanocomposites thin film," *J Nanopart Res* 12:2415-2426.
Ma, L.L. et al. (Jan. 18, 2013, e-published Dec. 13, 2012). "Growth of textured thin Au coatings on iron oxide nanoparticles with near infrared absorbance," *Nanotechnology* 24(2):025606.
Ma, L.L. et al (Sep. 22, 2009). "Small Multifunctional Nanoclusters (Nanoroses) for Targeted Cellular Imaging and Therapy," *ACS Nano* 3(9):2686-2696.
Shen, T. et al (1993). "Monocrystalline Iron Oxide Nanocompounds (Mion): Physicochemical Properties," *Magn Reson Med* 29:599-604.

* cited by examiner

*Primary Examiner* — Robert Cabral
(74) *Attorney, Agent, or Firm* — Mintz Levin Cohn Ferris Glovsky and Popeo, P.C.

(57) ABSTRACT

Provided herein are compositions and methods of preparing nanoparticle aggregates.

20 Claims, 17 Drawing Sheets

|  | Methanol | Water | Chloroform | Toluene | DMSO | Acetonitrile | Hexanes | THF |
|---|---|---|---|---|---|---|---|---|
| Phenyl-Maleimide | Yes | Slightly | No | No | Yes | Slightly | No | Slightly |
| PEG-Maleimide | No | Yes | No | No | Yes | No | No | Slightly |

A

B

A

B

C

Particles were conjugated to a targeting moiety, Folate, and a detection moiety FITC. Particle size was determine by analyzing TEM images with Matlab.

Figure 15

| | VS-PEG-FITC | Mal-PEG-FITC |
|---|---|---|
| HD | 54.9 | 55.5 |
| PDI | 0.081 | 0.031 |
| Fluorescence Intensity | 3190 | 4603 |

CHEMICALLY-LINKED NANOPARTICLES

RELATED APPLICATIONS

This application claims the benefit of U.S. Provisional Application No. 61/838,597 filed Jun. 24, 2013, which is hereby incorporated by reference in its entirety and for all purposes.

BACKGROUND OF THE INVENTION

Previous nanoparticle aggregate synthesis methods are limited by the variation in aggregate size leading to variation in aggregate morphology. Uncontrolled morphology may lead to inconsistent and irregular behaviors in vivo. Further, such methods result in free reactive groups present in the aggregates, leading to aggregate formation issues and undesired complexation. Accordingly, there is a need in the art for methods of synthesizing nanoparticle aggregates having in-vivo and ex-vivo applications that are formed with stable morphology. Provided herein are solutions to these and other problems in the art.

BRIEF SUMMARY OF THE INVENTION

Provided herein are nanoparticle aggregates. In a first aspect is a nanoparticle aggregate that includes a plurality of interior nanoparticle cores bound together and enclosed by a plurality of exterior nanoparticle cores bound together, wherein at least a portion of the plurality of interior nanoparticle cores are bound to the plurality of exterior nanoparticle cores. The nanoparticle aggregate further includes a plurality of interior polyvalent linkers binding the interior nanoparticle cores together, binding the exterior nanoparticle cores together, and binding the portion of the interior nanoparticle cores to the exterior nanoparticle cores, wherein each of the plurality of interior polyvalent linkers includes a central polyvalent moiety covalently bound to at least two nanoparticle linkers, each of the nanoparticle linkers bound to one of the interior nanoparticle cores or one of the exterior nanoparticle cores. The nanoparticle aggregate further includes a plurality of exterior polyvalent linkers binding at least one capping substituent to at least a portion of the exterior nanoparticle cores, wherein each of the plurality of exterior polyvalent linkers includes the central polyvalent moiety covalently bound to at least one of the nanoparticle linkers, the nanoparticle linkers bound to one of the exterior nanoparticle cores, and at least one capping linker bound to the capping substituent, wherein the exterior polyvalent linker includes at least two nanoparticle linkers and capping linkers combined.

Also provided herein are methods of preparing nanoparticle aggregates. In one aspect is a method for preparing a nanoparticle aggregate as described herein, including embodiments. The method includes contacting a plurality of nanoparticle cores with a first plurality of reactive polyvalent linkers thereby forming a plurality of polyvalent linkers binding the nanoparticle cores together, wherein a first portion of the plurality of nanoparticle cores are bound to together to form a plurality of interior nanoparticle cores and a second portion of the plurality of nanoparticle cores are bound together to form a plurality of exterior nanoparticle cores enclosing the plurality of interior nanoparticle cores, wherein the plurality of exterior nanoparticle cores are bound to a portion of the plurality of interior nanoparticle cores. The method further includes allowing a portion of the plurality of reactive polyvalent linkers to react with a portion of the exterior nanoparticle cores thereby forming a plurality of reactive exterior polyvalent linkers bound to the portion of the plurality of exterior nanoparticle cores. The method further includes contacting the nanoparticle aggregate with a reactive capping substituent and allowing the reactive capping substituent to react with the plurality of reactive exterior polyvalent linkers thereby forming the nanoparticle aggregate.

Further provided herein are methods of delivering or administering a nanoparticle aggregate to a subject in need thereof. In one aspect, is a method of treating cancer in a subject in need thereof. The method includes administering to a subject in need thereof a nanoparticle aggregate as described herein, where the nanoparticle aggregate includes a therapeutic moiety (e.g. an anticancer agent) as described herein, thereby treating the cancer. In another aspect, is a method of detecting a solid tumor in a subject in need thereof. The method includes administering to a subject in need thereof, a nanoparticle aggregate as described herein, where the nanoparticle aggregate includes a detectable moiety as described herein thereby detecting a solid tumor in a subject in need thereof.

BRIEF DESCRIPTION OF THE DRAWINGS

FIG. 15: Effects of vinyl sulfone (VS): particles were capped with a mixture of PEG-Maleimide and either Vinyl Sulfone-PEG-FITC or Maleimide-PEG-FITC and particle size was analyzed by DLS and Fluorescence intensity was measured using a fluormeter.

DETAILED DESCRIPTION OF THE INVENTION

I. Definitions

Figure 1:
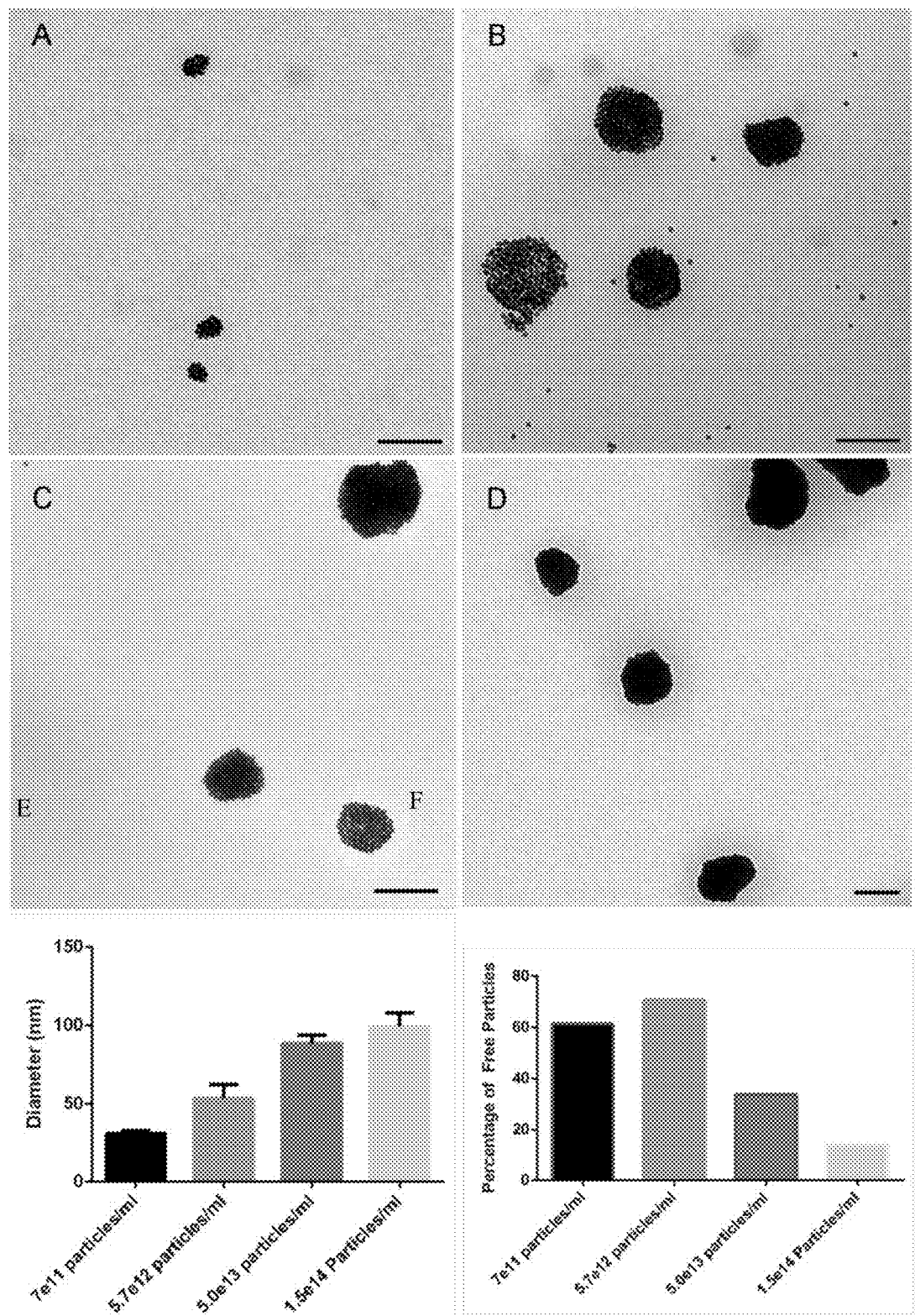
FIG. 1: Impact of particle concentration on nanoparticle aggregate using 10 nm nanoparticle cores, where A) shows $7 \times 10^{11}$ particles/ml; B) shows $5.7 \times 10^{12}$ particles/ml; C) shows $5.0 \times 10^{13}$ particles/ml; D) shows $1.5 \times 10^{14}$ particles/ml, (scale bars represent 100 nm); E) shows the average diameter of the aggregates, not including free particles, measured with an image analysis program (error bars are SEM); and F) shows the number of free particles (<20 nm) out of the entire population as a measure of efficiency.
Figure 2:
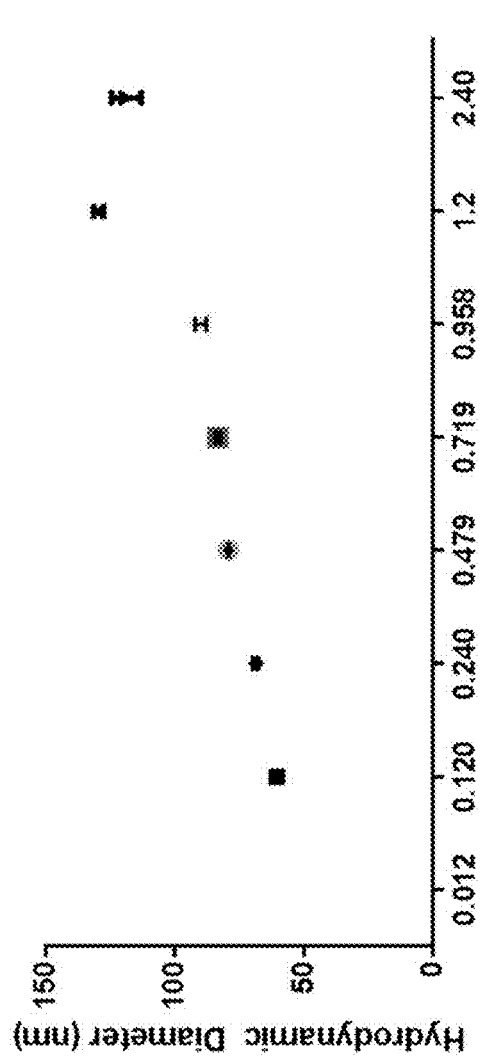
FIG. 2: Impact of pentaerythritol tetrakis (3-mercaptopropionate) (PTMP) on nanoparticle aggregate formation, particle size can be controlled by varying the concentration of the crosslinker from 0.12 mM to 2.4 mM PTMP.
Figure 2:
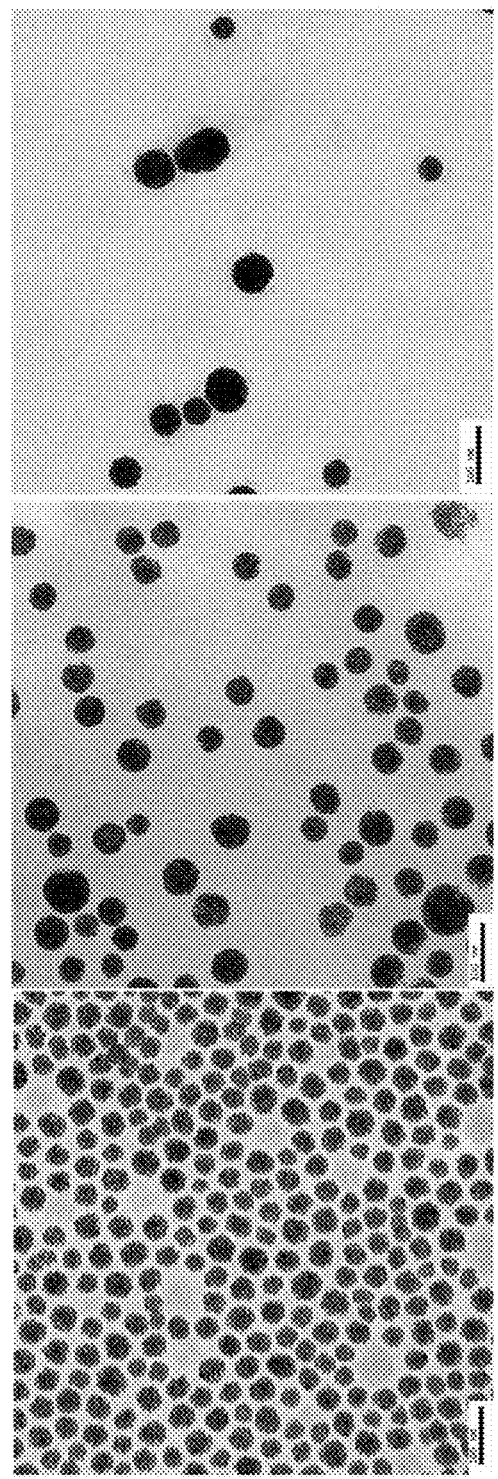

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e., unbranched) or branched chain, or combination thereof, which may be fully saturated, mono- or polyunsaturated and can include di- and multivalent radicals, having the number of carbon atoms designated (i.e., $C_1$-$C_{10}$ means one to ten carbons). Alkyl is not cyclized. Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —$CH_2CH_2CH_2CH_2$—. Typically, an alkyl (or alkylene) group will have from 1 to 24 carbon atoms. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or combinations thereof, consisting of at least one carbon atom and at least one heteroatom selected from the group consisting of O, N, P, S, Se and Si, and wherein the nitrogen, selenium, and sulfur atoms may optionally be oxidized, and the nitrogen heteroatom may optionally be quaternized. The heteroatom(s) O, N, P, S, Se, and Si may be placed at any interior position of the heteroalkyl group or at the position at which the alkyl group is attached to the remainder of the molecule. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH═CH—O—$CH_3$, —Si($CH_3$)$_3$, —$CH_2$—CH═N—$OCH_3$, —CH═CH—N($CH_3$)—$CH_3$, —O—$CH_3$, —O—$CH_2$—$CH_3$, and —CN. Up to two heteroatoms may be consecutive, such as, for example, —$CH_2$—NH—$OCH_3$.

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. Heteroalkyl is not cyclized. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SeR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (e.g. 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain from one to four heteroatoms (e.g. N, O, or S), wherein sulfur heteroatoms are optionally oxidized, and the nitrogen heteroatoms are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively.

A fused ring heterocycloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein. Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The term "oxo," as used herein, means an oxygen that is double bonded to a carbon atom.

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN, and —NO$_2$ in a number ranging from zero to (2m'+1), where m' is the total number of carbon atoms in such radical. R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy, or thioalkoxy groups, or arylalkyl groups. When a compound of the invention includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN, —NO$_2$, —R', —N$_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R'", and R'''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R''', and R'''' groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR"—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R''')$_d$—, where s and d are independently integers of from 0 to 3, and X' is —O—, —NR'—, —S—, —S(O)—, —S(O)$_2$—, or —S(O)$_2$NR'—. The substituents R, R', R", and R''' are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from: oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, and each substituted or unsubstituted heterocycloalkyl is a substituted or unsubstituted 3 to 8 membered heterocycloalkyl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, and each substituted or unsubstituted heterocycloalkyl is a substituted or unsubstituted 3 to 7 membered heterocycloalkyl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, and/or each substituted or unsubstituted heterocycloalkyl is a substituted or unsubstituted 3 to 8 membered heterocycloalkyl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, and/or each substituted or unsubstituted heterocycloalkylene is a substituted or unsubstituted 3 to 8 membered heterocycloalkylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, and/or each substituted or unsubstituted heterocycloalkyl is a substituted or unsubstituted 3 to 7 membered heterocycloalkyl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, and/or each substituted or unsubstituted heterocycloalkylene is a substituted or unsubstituted 3 to 7 membered heterocycloalkylene.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C). All isotopic variations of the compounds of the present invention, whether radioactive or not, are encompassed within the scope of the present invention.

The symbol "$\sim\!\!\sim$" denotes the point of attachment of a chemical moiety to the remainder of a molecule or chemical formula.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different (i.e. independently substituted). Where a particular R group is present in the description of a chemical genus (such as Formula (I)), a Roman alphabetic symbol may be used to distinguish each appearance of that particular R group. For example, where multiple $R^3$ substituents are present, each $R^3$ substituent may be distinguished as $R^{3A}$, $R^{3B}$, $R^{3C}$, $R^{3D}$, etc., wherein each of $R^{3A}$, $R^{3B}$, $R^{3C}$, $R^{3D}$, etc. is defined within the scope of the definition of $R^3$ and optionally differently.

Description of the present invention is limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

The nanoparticle aggregates of the present invention may exist as salts, such as with pharmaceutically acceptable acids. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms are preferably regenerated by contacting the salt with a base or acid and isolating the parent in the conventional manner. The parent form differs from the various salt forms in certain physical properties, such as solubility in polar solvents.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be, for example, a linker as described herein and a nanoparticle core. In some embodiments contacting includes, for example, allowing a linker described herein to interact with a capping substituent.

The terms "treating", or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, include prevention of an injury, pathology, condition, or disease.

As defined herein, the term "inhibitor" and the like refer to reduction of a disease or symptoms of disease. In some embodiments, inhibition refers to a reduction in the activity of a particular protein or nucleic acid target. Thus, inhibition includes, at least in part, partially or totally blocking stimulation, decreasing, preventing, or delaying activation, or inactivating, desensitizing, or down-regulating signal transduction or enzymatic activity or the amount of a protein.

The term "modulator" refers to a composition that increases or decreases the level of a target molecule or the function of a target molecule. In some embodiments, a modulator refers to a composition that reduces the severity of one or more symptoms of a disease or symptom of a disease (e.g. cancer).

An "effective amount" is an amount sufficient for an active to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations.

For any nanoparticle aggregate described herein, the therapeutically effective amount can be initially determined from cell culture assays. Target concentrations will be those concentrations of nanoparticle aggregates that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring effectiveness and adjusting the dosage upwards or downwards, as described above. Adjusting the dose to achieve maximal efficacy in humans based on the methods described above and other methods is well within the capabilities of the ordinarily skilled artisan. Dosages may be varied depending upon the requirements of the patient and the nanoparticle aggregate being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the nanoparticle aggregate. Thereafter, the dosage is increased by small increments until the optimum effect under circumstances is reached. Dosage amounts and intervals can be adjusted individually to provide levels of the administered nanoparticle aggregate effective for the particular clinical indication being treated. This will provide a therapeutic regimen that is commensurate with the severity of the individual's disease state.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

"Disease" or "condition" refer to a state of being or health status of a patient or subject capable of being treated with the compounds or methods provided herein. Disease or condition may refer to cancer, including solid tumor cancers.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active or prodrug form of a nanoparticle aggregate as provided herein with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

By "co-administer" it is meant that a composition described herein is administered at the same time, just prior to, or just after the administration of one or more additional therapies. The compound of the invention can be administered alone or can be co-administered to the patient. Co-administration is meant to include simultaneous or sequential administration of the compound individually or in combination (more than one compound or agent). Thus, the preparations can also be combined, when desired, with other active substances (e.g. to reduce metabolic degradation).

The nanoparticle aggregates disclosed herein can be delivered transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Liquid form preparations may include solutions, suspensions, and emulsions, for example, water or water/propylene glycol solutions. The compositions of the nanoparticle aggregates described herein may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions disclosed herein can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997).

Pharmaceutical compositions of the nanoparticle aggregates described herein may include compositions having a therapeutic moiety contained in a therapeutically effective amount, i.e., in an amount effective to achieve its intended purpose. The pharmaceutical compositions of the nanoparticle aggregates described herein may include compositions having detectable moieties contained in an effective amount, i.e., in an amount effective to achieve its intended purpose. The actual amount effective for a particular application will depend, inter alia, on the condition being treated, tested, detected, or diagnosed. When administered in methods to treat a disease, such compositions will contain an amount of active ingredient effective to achieve the desired result, e.g., modulating the activity of a target molecule, and/or reducing, eliminating, or slowing the progression of disease symptoms. When administered in methods to diagnose or detect a disease, such compositions will contain an amount of a detectable moiety described herein effective to achieve the desired result, e.g., detecting the absence or presence of a target molecule, cell, or tumor in a subject.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic/detection regimens or agents can be used in conjunction with the methods and compounds of nanoparticle aggregates described herein. Adjustment and manipulation of established dosages (e.g., frequency and duration) are well within the ability of those skilled in the art.

For any nanoparticle aggregate described herein, which contains a therapeutic or detectable moiety, the effective (i.e. therapeutically effective) amount can be initially determined from cell culture assays. Target concentrations will be those concentrations of nanoparticle aggregates that are capable of achieving the methods described herein, as measured using the methods described herein or known in the art.

As is well known in the art, effective amounts for use in humans can also be determined from animal models. For example, a dose for humans can be formulated to achieve a concentration that has been found to be effective in animals. The dosage in humans can be adjusted by monitoring effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the nanoparticle aggregate being employed. The dose administered to a patient, in the context of the present invention should be sufficient to effect a beneficial response (e.g. therapeutic or detect/diagnose) in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered nanoparticle aggregate effective for the particular indication being investigated. This will provide a regimen that is commensurate with the severity of the individual's disease state.

"Nucleic acid" refers to deoxyribonucleotides or ribonucleotides and polymers thereof in either single- or double-stranded form, and complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA. Nucleic acid as used herein also refers nucleic acids that have the same basic chemical structure as a naturally occurring nucleic acids. Such analogues have modified sugars and/or modified ring substituents, but retain the same basic chemical structure as the naturally occurring nucleic acid. A nucleic acid mimetic refers to chemical compounds that have a structure that is different the general chemical structure of a nucleic acid, but that functions in a manner similar to a naturally occurring nucleic acid. Examples of such analogues include, without limitation, phosphorothioates, phosphoramidates, methyl phosphonates, chiral-methyl phosphonates, 2-O-methyl ribonucleotides, and peptide-nucleic acids (PNAs).

"Synthetic mRNA" as used herein refers to any mRNA derived through non-natural means such as standard oligonucleotide synthesis techniques or cloning techniques. Such mRNA may also include non-proteinogenic derivatives of naturally occurring nucleotides. Additionally, "synthetic mRNA" herein also includes mRNA that has been expressed through recombinant techniques or exogenously, using any expression vehicle, including but not limited to prokaryotic cells, eukaryotic cell lines, and viral methods. "Synthetic mRNA" includes such mRNA that has been purified or otherwise obtained from an expression vehicle or system.

The terms "polypeptide," "peptide" and "protein" are used interchangeably herein to refer to a polymer of amino acid residues, wherein the polymer may optionally be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "peptidyl" and "peptidyl moiety" means a monovalent peptide.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

For preparation of suitable antibodies of the invention and for use according to the invention, e.g., recombinant, monoclonal, or polyclonal antibodies, many techniques known in the art can be used (see, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy*, Alan R. Liss, Inc. (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, *Immunology* ($3^{rd}$ ed. 1997)). Techniques for the production of single chain antibodies or recombinant antibodies (U.S. Pat. No. 4,946,778, U.S. Pat. No. 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., *Bio/Technology* 10:779-783 (1992); Lonberg et al., *Nature* 368:856-859 (1994); Morrison, *Nature* 368:812-13 (1994); Fishwild et al., *Nature Biotechnology* 14:845-51 (1996); Neuberger, *Nature Biotechnology* 14:826 (1996); and Lonberg & Huszar, *Intern. Rev. Immunol.* 13:65-93 (1995)). Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)). Antibodies can also be made bispecific, i.e., able to recognize two different antigens (see, e.g., WO 93/08829, Traunecker et al., *EMBO J.* 10:3655-3659 (1991); and Suresh et al., *Methods in Enzymology* 121:210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Methods for humanizing or primatizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Jones et al., *Nature* 321:522-525 (1986); Riechmann et al., *Nature* 332:323-327 (1988); Verhoeyen et al., *Science* 239:1534-1536 (1988) and Presta, *Curr. Op. Struct. Biol.* 2:593-596 (1992)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. The preferred antibodies of, and for use according to the invention include humanized and/or chimeric monoclonal antibodies.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., spodoptera) and human cells. Cells may be useful when they are naturally nonadherent or have been treated not to adhere to surfaces, for example by trypsinization.

A "nanoparticle core," as used herein, is a particle wherein the longest diameter is less than 1000 nanometers. The nanoparticle aggregates of the present invention are formed of nanoparticle cores. Nanoparticles may be composed of any appropriate material. For example, nanoparticle cores may include appropriate metals and metal oxides thereof (a metal nanoparticle core), carbon (an organic nanoparticle core) silicon and oxides thereof (a silicon nanoparticle core) or boron and oxides thereof (a boron nanoparticle core).

The nanoparticle aggregates herein include, in part, polyvalent linkers. A "polyvalent linker," as provided herein, chemically links together element of a nanoparticle aggregates (e.g. nanoparticle cores). Polyvalent linkers may include the conjugated product of reactive groups at the point of attachment to a nanoparticle core, at the point of attachment to a cleavage site, at the point of attachment to a capping substituent, or at a location between. Thus, polyvalent linkers may be formed by conjugate chemistry techniques.

A "nanoparticle linker" as used herein refers to a portion of a polyvalent linker covalently bonded to a nanoparticle core and covalently bonded to a central polyvalent moiety. The nanoparticle linker moiety may be a linker formed by reacting a functional (reactive) group attached to the linker with a nanoparticle core. The nanoparticle linker moiety may be a linker formed by reacting a functional (reactive) group attached to the linker with the central polyvalent linker. A nanoparticle linker may have the formula:

NC1-NL1-CPM-NL2-NC2    (I).

In Formula (I), NC1 is a first nanoparticle core, NL1 is a first nanoparticle linker, CPM is a central polyvalent moiety, NC2 is a second nanoparticle core, and NL2 is a second nanoparticle core. The CPM may have more than two NLs as described herein, including embodiments thereof. NC1 and NC2 may be further linked to additional nanoparticle linkers or capping linkers as described herein.

A "capping linker" as used herein refers to a portion of a polyvalent linker covalently bonded to central polyvalent moiety and a capping substituent. The capping linker moiety may be a linker formed by reacting a functional (reactive) group attached to the linker with the capping substituent. The capping linker moiety may be a linker formed by reacting a functional (reactive) group attached to the linker with the central polyvalent linker. A capping linker may have the formula:

CS1-CL1-CPM-NL1-NC1    (II).

In Formula (II), CS1 is a first capping substituent, CL1 is a first capping linker, CPM is a central polyvalent moiety, NL1 is a first nanoparticle linker and NC1 is a first nanoparticle core. The CPM may have more than two NLs and/or CLs as described herein, including embodiments thereof. NC1 may be further linked to additional nanoparticle linkers or capping linkers as described herein.

A "central polyvalent linker" as used herein refers to a polyvalent moiety covalently attached to at least two nanoparticle linkers and capping linkers combined. The valency of the central polyvalent linker is equal to the number of nanoparticle linkers and capping linkers combined.

An "amino acid sequence linker" as used herein refers to a polyvalent linker, nanoparticle linker, or capping linker having an amino acid sequence. In embodiments, the amino acid sequence linker is a bivalent amino acid sequence. Likewise, a "nucleic acid sequence linker" refers to a polyvalent linker, nanoparticle linker, or capping linker having a nucleic acid sequence. In embodiments, the nucleic acid sequence linker is a bivalent nucleic acid sequence.

A "capping substituent" as used herein is a chemical moiety that is covalently attached to a capping linker (typically linked to the remainder of the molecule using conjugate chemistry as known in the art and described herein). In embodiments, the capping substituent further includes a capping functional group. A capping functional group is a moiety non-covalently or covalently bonded to the capping substituent typically formed or linked to the remainder of the molecule using by conjugate chemistry. Currently favored classes of conjugate chemistry reactions available with reactive known reactive groups are those which proceed under relatively mild conditions. These include, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

Useful reactive functional groups used for conjugate chemistries herein include, for example:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups which can be converted to esters, ethers, aldehydes, etc.

(c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups which are capable of participating in Diels-Alder reactions such as, for example, maleimido groups;

(e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be converted to disulfides, reacted with acyl halides, or bonded to metals such as gold;

(h) amine or sulfhydryl groups, which can be, for example, acylated, alkylated or oxidized;

(i) alkenes, which can undergo, for example, cycloadditions, acylation, Michael addition, etc;

(j) epoxides, which can react with, for example, amines and hydroxyl compounds;

(k) phosphoramidites and other standard functional groups useful in nucleic acid synthesis;

(i) metal silicon oxide bonding; and (l) metal bonding to reactive phosphorus groups (e.g. phosphines) to form, for example, phosphate diester bonds.

The reactive functional groups can be chosen such that they do not participate in, or interfere with, the chemical stability of the nanoparticle aggregates described herein. Alternatively, a reactive functional group can be protected from participating in the crosslinking reaction by the presence of a protecting group.

A "cleavage site" as used herein, refers to a recognizable site for cleavage of a portion of the polyvalent linker from the nanoparticle core or capping substituent. The cleavage site may be located within a capping linker or a nanoparticle linker. In embodiments, the cleavage site is an amino acid sequence that is recognized and cleaved by a cleavage agent. Exemplary cleavage agents include proteins, enzymes, DNAzymes, RNAzymes, metals, acids, bases, or photocleavage. Exemplary cleavage sites are defined herein.

A "biological moiety" as used herein refers a monovalent molecule produced in a living cell or any synthetically derived molecule that mimics or is an analogue of a molecule produced in a living cell and maintains biological activity. Biomolecules that may serve as biological moieties in their monovalent form include nucleotides, polynucleotides (e.g. RNA, DNA), amino acids, peptides, polypeptides, proteins, polysaccharides, lipids. glycans, and small molecules (e.g. vitamins, primary and secondary metabolites, hormones, neurotransmitters). Amino acids may include moieties other than those found in the naturally occurring 20 amino acids (e.g. selenocysteine, pyrrolysine, carnitine, ornithine, GABA, and taurine). Amino acids may also include non-proteinogenic functional groups (e.g. $CF_3$, $N_3$, F, $NO_2$). Likewise, polypeptides and proteins may contain such amino acids. "Polysaccharides" include mono-, di-, and oligo-saccharides including O— and N— glycosyl-linkages. Polysaccharides may include functional group moieties not commonly found in a cellular. Lipids include amphipathic-, phospho-, and glycol-lipids and sterols such as cholesterol. An "amphipathic lipid" refers to a lipid having hydrophilic and hydrophobic characteristics. A "phospholipid" refers to a lipid bound to a phosphate group and carries a charge. Exemplary phospholipids include phosphatidic acid, phosphatidylethanolamine, phosphatidylcholine, phosphatidylserine, and phosphatidylinositol. A "glycolipid" refers to a lipid bound to a poly- or oligo-saccharide. Exemplary glycolipids include galactolipids, sulfolipids, glycosphingolipids, and glycosylphosphatidylinositol. Lipids may include substituents not commonly found in the cellular environment. A "small molecule" as used herein refers to any small molecule produced naturally in a biological environment and may contain unnatural moieties or linkages not typically found in a cell but tolerated during processing within a cell.

A "hydrophilic moiety" as used herein, refers to a monovalent compound that increases the hydrophilicity of the nanoparticle aggregate thereby increasing solubilization in a hydrophilic solution. A hydrophilic moiety may increase solubility of a nanoparticle aggregate in polar organic solvents.

A "hydrophobic moiety" as used herein, refers to a monovalent compound that increases the hydrophobicity of a nanoparticle aggregate. The hydrophobic moiety may increase solubility of the nanoparticle aggregate in hydrophobic solutions. A hydrophobic moiety may increase solubility of a nanoparticle aggregate in nonpolar organic solvents. A hydrophobic moiety may alter the partitioning coefficient of the nanoparticle aggregate to which it is bound thereby making aggregate more hydrophobic.

A "therapeutic moiety" as used herein refers to a monovalent compound having a prophylactic effect for a disease or condition (e.g. cancer) when given to a subject in need thereof. In embodiments, a therapeutic moiety is an anticancer agent or chemotherapeutic agent as described herein.

A "targeting moiety" includes a monovalent compound capable of binding to, or otherwise exhibiting an affinity for, a particular type of tissue or component thereof. The addition of a targeting moiety to a nanoparticle aggregate can direct the nanoparticle aggregate to particular sites within the body. Targeting moieties may include, for example, proteins, antibodies, antibody fragments, peptides, carbohydrates, lipids, oligonucleotides, DNA, RNA, or small molecules having a molecular weight less than 2000 Daltons. A targeting moiety also includes any chemical moiety capable of binding to, or otherwise exhibiting an affinity for a particular exogenous or environmental agent, for example, detection of environment contaminates or oil.

A "detectable moiety" as used herein refers to a moiety that can be covalently or noncovalently attached to a compound or biomolecule that can be detected for instance, using techniques known in the art, for example Raman spectroscopy, magnetic resonance imaging (MRI), ultrasound, radiolabeling, elemental analysis (e.g. X-ray photoelectron spectroscopy) or fluorescence. In embodiments, the detectable moiety is covalently attached. The detection moiety may provide for imaging of the attached compound or biomolecule. The detection moiety may indicate the contacting between two compounds. The detection may be to image a solid tumor in a subject in need thereof. Thus, in embodiments, the detectable moiety may be used to diagnose cancer in a subject. Exemplary detectable moieties are fluorophores, antibodies, reactive dies, radio-labeled moieties, magnetic contrast agents, quantum dots, molecules detectable by Raman spectroscopy, molecules having predetermined measurable masses, or bioluminescent molecules.

A "water soluble polymer moiety" as used herein refers to a monovalent compound that enhances the water solubility of the compound or molecule to which it is bound. moiety may alter the partitioning coefficient of a compound or molecule to which it is bound thereby making the molecule more or less hydrophilic. The more hydrophobic a compound, the higher its partition constant. The more hydrophilic a compound, the lower its partition constant. In some embodiments, the water soluble groups can decrease the partition constant of precursor molecules (which have a higher partition constant before attachment of the water soluble group) at least by about 10%, 20%, 30%, 40%, 50%, 60%, 70%, 80%, or 90%. In some embodiments, the water soluble groups described herein can decrease the partition constant of precursor molecules by 1-fold, 2-fold, 3-fold, 4-fold, or greater. Exemplary water soluble moieties include moieties such as poly(oxyethylated polyols) such as poly(oxyethylated glycerol), poly(oxyethylated sorbitol), and poly(oxyethylated glucose); poly(vinyl alcohol) ("PVA"); dextran; carbohydrate-based polymers and the like (including linear chains or branched chains); polyethylene glycol moieties terminating in —OH or —OMe; polyvinylpyroolidone moieties; or poly 2-ethyl oxazoline moieties. Polyethylene glycol moieties may have molecular weights from about 200 (e.g. $PEG_{200}$) to about 40,000 ($PEG_{40,000}$)

In some embodiments, the water soluble group can include a moiety containing a heteroatom (e.g., oxygen or nitrogen). In some embodiments to improve the water solubility of compounds herein a water soluble group is covalently attached at one or more positions. Such moieties include substituted alkyl moiety, substituted heteroalkyl moiety, substituted cycloalkyl moiety, substituted heteroalkyl moiety, or substituted aryl moiety. In embodiments, the moiety contains an alcohol moiety (an organic moiety having an —OH bound to a carbon atom), ester linker moiety (the linker moiety —C(O)O— between two carbon atoms), ether linker moiety (the linker moiety —O— between two carbon atoms), amine (—$NH_2$) moiety, nitrile (—CN) moiety, ketone moiety (the linker moiety —C(O)— between two carbon atoms), or aldehyde (—C(O)H) moiety.

Lengths and sizes of nanoparticles and nanoparticle aggregates as described herein may be measured using Transmission Electron Microscopy. For the transmission electron microscopy measurements 2 µL of solution were dried onto a 200 mesh carbon copper grid from TED Pella. TEM images were taken using FEI Tecnai 12 Twin. Images were analyzed using a Matlab program that found the edges of each aggregate/particle by identifying transitions in contrast in the TEM images and then calculated the area of each aggregate/particle in the image, the area was converted to diameter by assuming a circular shape of the aggregate/particle. The diameters described in this document represent the means of the measured diameters. The efficiency of each reaction was determined by counting the number of free particles (defined as less than twice the single particle radius) and dividing by total events counted. Lengths and sizes may be measured by dynamic light scattering (DLS) as described herein.

As used herein, the term "cancer" refers to all types of cancer, neoplasm, or malignant solid tumors found in mammals, including melanomas, lymphomas, carcinomas and sarcomas. Exemplary cancers include cancer of the brain, breast, pancreas, colon, liver, kidney, lung, non-small cell lung, melanoma, ovary, sarcoma, and prostate. Additional examples include, cervix cancers, stomach cancers, head & neck cancers, uterus cancers, mesothelioma, metastatic bone cancer, Medulloblastoma, Hodgkin's Disease, Non-Hodgkin's Lymphoma, multiple myeloma, neuroblastoma, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine and exocrine pancreas, and prostate cancer The term "sarcoma" generally refers to a tumor which is made up of a substance like the embryonic connective tissue and is generally composed of closely packed cells embedded in a fibrillar or homogeneous substance. Sarcomas which can be treated with a combination of antineoplastic thiol-binding mitochondrial oxidant and an anticancer agent include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumor arising from the melanocytic system of the skin and other organs. Melanomas which can be treated with a combination of antineoplastic thiol-binding mitochondrial oxidant and an anticancer agent include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, and superficial spreading melanoma.

The term "carcinoma" refers to a malignant new growth made up of epithelial cells tending to infiltrate the surrounding tissues and give rise to metastases. Exemplary carcinomas which can be treated with a combination of antineoplastic thiol-binding mitochondrial oxidant and an anticancer agent include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

Cancer model organism, as used herein, is an organism exhibiting a phenotype indicative of cancer, or the activity of cancer causing elements, within the organism. The term cancer is defined above. A wide variety of organisms may serve as cancer model organisms, and include for example, cancer cells and mammalian organisms such as rodents (e.g. mouse or rat) and primates (such as humans). Cancer cell lines are widely understood by those skilled in the art as cells exhibiting phenotypes or genotypes similar to in vivo cancers. Cancer cell lines as used herein includes cell lines from animals (e.g. mice) and from humans.

"Anti-cancer agent" is used in accordance with its plain ordinary meaning and refers to a composition (e.g. compound, drug, antagonist, inhibitor, modulator) having anti-neoplastic properties or the ability to inhibit (e.g. decrease) the growth or proliferation of cells. In some embodiments, an anti-cancer agent is a chemotherapeutic. In some embodiments, an anti-cancer agent is an agent approved by the FDA or similar regulatory agency of a country other than the USA, for treating cancer.

"Chemotherapeutic" or "chemotherapeutic agent" is used in accordance with its plain ordinary meaning and refers to a chemical composition or compound that is an anti-cancer agent (having anti-neoplastic properties or the ability to inhibit the growth or proliferation of cells).

Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethylmelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec™), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin I1 (including recombinant interleukin II, or rIL.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol™ (i.e. paclitaxel), Taxotere™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39.HCl), AC-7700 (Ajinomoto, i.e. AVE-8062, AVE-8062A, CS-39-L-Ser.HCl, and RPR-258062A), Vitilevuamide, Tubulysin A, Canadensol, Centaureidin (i.e. NSC-106969), T-138067 (Tularik, i.e. T-67, TL-138067 and TI-138067), COBRA-1 (Parker Hughes Institute, i.e. DDE-261 and WHI-261), H10 (Kansas State University), H16 (Kansas State University), Oncocidin A1 (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, i.e. MF-191), TMPN (Arizona State University), Vanadocene acetylacetonate, T-138026 (Tularik), Monsatrol, lnanocine (i.e. NSC-698666), 3-IAABE (Cytoskeleton/Mt. Sinai School of Medicine), A-204197 (Abbott), T-607 (Tuiarik, i.e. T-900607), RPR-115781 (Aventis), Eleutherobins (such as Desmethyleleutherobin, Desaetyleleutherobin, lso-eleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (i.e. NSCL-96F037), D-68838 (Asta Medica), D-68836 (Asta Medica), Myoseverin B, D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., Bacillus Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like.

II. Compositions

In a first aspect a nanoparticle aggregate is provided. The aggregate includes a plurality of interior nanoparticle cores bound together and enclosed by a plurality of exterior nanoparticle cores bound together, wherein at least a portion of the plurality of interior nanoparticle cores are bound to the plurality of exterior nanoparticle cores. The aggregate further includes a plurality of interior polyvalent linkers binding the interior nanoparticle cores together, binding the exterior nanoparticle cores together, and binding the portion of the interior nanoparticle cores to the exterior nanoparticle cores, wherein each of the plurality of interior polyvalent linkers includes a central polyvalent moiety covalently bound to at least two nanoparticle linkers, each of the nanoparticle linkers bound to one of the interior nanoparticle cores or one of the exterior nanoparticle cores. The aggregate further includes a plurality of exterior polyvalent linkers binding at least one capping substituent to at least a portion of the exterior nanoparticle cores, wherein each of the plurality of exterior polyvalent linkers includes the central polyvalent moiety covalently bound to at least one of the nanoparticle linkers, the nanoparticle linkers bound to one of the exterior nanoparticle cores, and at least one capping linker bound to the capping substituent, wherein the exterior polyvalent linker includes at least two nanoparticle linkers and capping linkers combined.

The interior nanoparticle cores and exterior nanoparticle cores may be chemically identical. The interior nanoparticle cores and exterior nanoparticle cores may have a different chemical composition from each other. The interior nanoparticle cores and exterior nanoparticle may independently be metal nanoparticle cores. When the nanoparticle cores are metal nanoparticle cores, they may be any appropriate metal, including metal oxides. Appropriate metals include, for example, titanium, zirconium, gold, silver, platinum, cerium, arsenic, iron, cadmium, selenium, aluminum, or zinc, including oxides thereof. Metal interior nanoparticle cores and exterior nanoparticle may independently be transition metals such as, for example, titanium, iron, cobalt, nickel, copper, zinc, zirconium, palladium, cadmium, tungsten, silver, platinum, or gold. The interior nanoparticle cores and exterior nanoparticle may be gold. The interior nanoparticle cores and exterior nanoparticle may independently be carbon nanoparticle cores (e.g. organic nanoparticle cores). The interior nanoparticle cores and exterior nanoparticle may independently be silicon nanoparticle cores, including oxides thereof. The interior nanoparticle cores and exterior nanoparticle may independently be boron nanoparticle cores, including oxides thereof.

The interior nanoparticle cores and exterior nanoparticle may independently be about 2 nm to about 750 nm in diameter, wherein the diameter is the measure of the longest width of the nanoparticle core, as measured by TEM as described herein. The interior nanoparticle cores and exterior nanoparticle may independently be about 2 nm to about 750 nm in diameter, wherein the diameter is the measure of the longest width of the nanoparticle core, as measured by DLS as described herein. The nanoparticle cores described herein may be measured using TEM or DLS as described herein. The diameter of the interior nanoparticle cores and exterior nanoparticle may independently be about 2 nm to about 500 nm. The diameter of the interior nanoparticle cores and exterior nanoparticle may independently be about 2 nm to about 250 nm. The diameter of the interior nanoparticle cores and exterior nanoparticle may independently be about 2 nm to about 100 nm. The diameter of the interior nanoparticle cores and exterior nanoparticle may independently be about 2 nm to about 50 nm. The diameter of the interior nanoparticle cores and exterior nanoparticle may independently be about 2 nm to about 30 nm. The diameter of the interior nanoparticle cores and exterior nanoparticle may independently be about 2 nm to about 20 nm. The diameter of the interior nanoparticle cores and exterior nanoparticle may independently be about 2 nm to about 15 nm. The diameter of the interior nanoparticle cores and exterior nanoparticle may independently be about 2 nm to about 10 nm. The diameter of the interior nanoparticle cores and exterior nanoparticle may independently be about 2 nm to about 5 nm. The diameter of the interior nanoparticle cores and exterior nanoparticle may independently be about 5 nm to about 100 nm. The diameter of the interior nanoparticle cores and exterior nanoparticle may independently be about 5 nm to about 50 nm. The diameter of the interior nanoparticle cores and exterior nanoparticle may independently be about 5 nm to about 25 nm. The diameter of the interior nanoparticle cores and exterior nanoparticle may independently be about 5 nm to about 20 nm. The diameter of the interior nanoparticle cores and exterior nanoparticle may independently be about 5 nm to about 10 nm.

The diameter of the interior nanoparticle cores and exterior nanoparticle may independently be about 500 nm. The diameter of the interior nanoparticle cores and exterior nanoparticle may independently be about 250 nm. The diameter of the interior nanoparticle cores and exterior nanoparticle may independently be about 100 nm. The diameter of the interior nanoparticle cores and exterior nanoparticle may independently be about 50 nm. The diameter of the interior nanoparticle cores and exterior nanoparticle may independently be about 25 nm. The diameter of the interior nanoparticle cores and exterior nanoparticle may independently be about 20 nm. The diameter of the interior nanoparticle cores and exterior nanoparticle may independently be about 15 nm. The diameter of the interior nanoparticle cores and exterior nanoparticle may independently be about 10 nm. The diameter of the interior nanoparticle cores and exterior nanoparticle may independently be about 5 nm. The diameter of the interior nanoparticle cores and exterior nanoparticle may independently be about 2 nm.

The diameter of the interior nanoparticle cores and the exterior nanoparticle cores may be measured as the average size distribution of the cores. Accordingly, the average diameter of the interior nanoparticle cores and exterior nanoparticle may independently be about 2 nm to about 500 nm. The average diameter of the interior nanoparticle cores and exterior nanoparticle may independently be about 2 nm to about 250 nm. The average diameter of the interior nanoparticle cores and exterior nanoparticle may independently be about 2 nm to about 100 nm. The average diameter of the interior nanoparticle cores and exterior nanoparticle may independently be about 2 nm to about 50 nm. The average diameter of the interior nanoparticle cores and exterior nanoparticle may independently be about 2 nm to about 20 nm. The average diameter of the interior nanoparticle cores and exterior nanoparticle may independently be about 2 nm to about 10 nm. The average diameter of the interior nanoparticle cores and exterior nanoparticle may independently be about 2 nm to about 5 nm. The average diameter of the interior nanoparticle cores and exterior nanoparticle may independently be about 5 nm to about 100 nm. The average diameter of the interior nanoparticle cores and exterior nanoparticle may independently be about 5 nm to about 50 nm. The average diameter of the interior nanoparticle cores and exterior nanoparticle may independently be about 5 nm to about 20 nm. The average diameter of the interior nanoparticle cores and exterior nanoparticle may independently be about nm to about 10 nm.

The average diameter of the interior nanoparticle cores and exterior nanoparticle may independently be about 500 nm. The average diameter of the interior nanoparticle cores and exterior nanoparticle may independently be about 250 nm. The average diameter of the interior nanoparticle cores and exterior nanoparticle may independently be about 100 nm. The average diameter of the interior nanoparticle cores and exterior nanoparticle may independently be about 50 nm. The average diameter of the interior nanoparticle cores and exterior nanoparticle may independently be about 30 nm. The average diameter of the interior nanoparticle cores and exterior nanoparticle may independently be about 20 nm. The average diameter of the interior nanoparticle cores and exterior nanoparticle may independently be about 15 nm. The average diameter of the interior nanoparticle cores and exterior nanoparticle may independently be about 10 nm. The average diameter of the interior nanoparticle cores and exterior nanoparticle may independently be about 5 nm. The average diameter of the interior nanoparticle cores and exterior nanoparticle may independently be about 2 nm.

The nanoparticle aggregate may be about 13 nm to about 750 nm in diameter, wherein the diameter is the measure of the longest width of the nanoparticle core. The nanoparticle aggregate may be about 13 nm to about 500 nm in diameter. The nanoparticle aggregate may be about 13 nm to about 250 nm in diameter. The nanoparticle aggregate may be about 13 nm to about 100 nm in diameter. The nanoparticle aggregate may be about 35 nm to about 100 nm in diameter. The nanoparticle aggregate may be about 50 nm in diameter.

The nanoparticle linker may be —C(O)—, —C(O)O—, —O—, —S—, —NH—, —NR$^1$—, —C(O)NR$^2$—, —S(O)$_n$—, —S(O)NR$^3$—, —OP(O)(OR$^4$)O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, an amino acid sequence linker, or a nucleic acid sequence linker. R$^1$, R$^2$, R$^3$, R$^4$, are independently hydrogen, halogen, —N$_3$, —NO$_2$, —CF$_3$, —CCl$_3$, —CBr$_3$, —CI$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, OCH$_3$, —NHCNHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbol n is 1 or 2.

The nanoparticle linker may have formula:

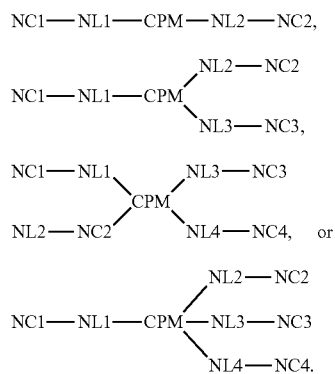

NC1 is a first nanoparticle core, NC2 is a second nanoparticle core, NC3 is a third nanoparticle core, and NC4 is a fourth nanoparticle core. CPM is a central polyvalent moiety, NL1 is a first nanoparticle linker, NL2 is a second nanoparticle linker, NL3 is a third nanoparticle linker, and NL4 is a fourth nanoparticle linker. Each nanoparticle core may be further linked to additional nanoparticle linkers or capping linkers as described herein. Each central polyvalent moiety may have at least two nanoparticle linkers and/or capping linkers as described herein, including embodiments thereof.

The nanoparticle linker may be —O—, —S—, C(O)O—, —SO$_2$—, or —NH—. The nanoparticle linker may be —O—, —S—, C(O)O—, or —NH—. The nanoparticle linker may be substituted or unsubstituted $C_1$-$C_{20}$ alkylene. The nanoparticle linker may be substituted or unsubstituted $C_1$-$C_{15}$ alkylene. The nanoparticle linker may be substituted or unsubstituted $C_1$-$C_{10}$ alkylene. The nanoparticle linker may be substituted or unsubstituted $C_1$-$C_5$ alkylene. The nanoparticle linker may be substituted or unsubstituted $C_1$-$C_3$ alkylene. The nanoparticle linker may be substituted or unsubstituted $C_3$-$C_8$ alkylene. The nanoparticle linker may be substituted or unsubstituted $C_3$-$C_6$ alkylene. The nanoparticle linker may be substituted or unsubstituted $C_3$-$C_5$ alkylene. The nanoparticle linker may be substituted or unsubstituted $C_6$ alkylene. The nanoparticle linker may be substituted or unsubstituted $C_5$ alkylene. The nanoparticle linker may be substituted or unsubstituted $C_4$ alkylene. The nanoparticle linker may be substituted or unsubstituted $C_3$ alkylene. The nanoparticle linker may be substituted or unsubstituted $C_2$ alkylene.

The nanoparticle linker may be $R^5$-substituted or unsubstituted $C_1$-$C_{15}$ alkylene. The nanoparticle linker may be $R^5$-substituted or unsubstituted $C_1$-$C_{10}$ alkylene. The nanoparticle linker may be $R^5$-substituted or unsubstituted $C_1$-$C_5$ alkylene. The nanoparticle linker may be $R^5$-substituted or unsubstituted $C_1$-$C_3$ alkylene. The nanoparticle linker may be $R^5$-substituted or unsubstituted $C_3$-$C_8$ alkylene. The nanoparticle linker may be $R^5$-substituted or unsubstituted $C_3$-$C_6$ alkylene. The nanoparticle linker may be $R^5$-substituted or unsubstituted $C_3$-$C_5$ alkylene. The nanoparticle linker may be $R^5$-substituted or unsubstituted $C_6$ alkylene. The nanoparticle linker may be $R^5$-substituted or unsubstituted $C_5$ alkylene. The nanoparticle linker may be $R^5$-substituted or unsubstituted $C_4$ alkylene. The nanoparticle linker may be $R^5$-substituted or unsubstituted $C_3$ alkylene. The nanoparticle linker may be $R^5$-substituted or unsubstituted $C_2$ alkylene.

The nanoparticle linker may be substituted or unsubstituted 2 to 20 membered heteroalkylene. The nanoparticle linker may be substituted or unsubstituted 2 to 15 membered heteroalkylene. The nanoparticle linker may be substituted or unsubstituted 2 to 10 membered heteroalkylene. The nanoparticle linker may be substituted or unsubstituted 2 to 5 membered heteroalkylene. The nanoparticle linker may be substituted or unsubstituted 2 to 3 membered heteroalkylene. The nanoparticle linker may be substituted or unsubstituted 3 to 8 membered heteroalkylene. The nanoparticle linker may be substituted or unsubstituted 2 to 20 membered heteroalkylene. The nanoparticle linker may be substituted or unsubstituted 3 to 6 membered heteroalkylene. The nanoparticle linker may be substituted or unsubstituted 3 to 5 membered heteroalkylene. The nanoparticle linker may be substituted or unsubstituted 6 membered heteroalkylene. The nanoparticle linker may be substituted 6 membered heteroalkylene. The nanoparticle linker may be unsubstituted 6 membered heteroalkylene. The nanoparticle linker may be substituted or unsubstituted 5 membered heteroalkylene. The nanoparticle linker may be substituted 5 membered heteroalkylene. The nanoparticle linker may be unsubstituted 5 membered heteroalkylene. The nanoparticle linker may be substituted or unsubstituted 4 membered heteroalkylene. The nanoparticle linker may be substituted 4 membered heteroalkylene. The nanoparticle linker may be unsubstituted 4 membered heteroalkylene. The nanoparticle linker may be substituted or unsubstituted 3 membered heteroalkylene. The nanoparticle linker may be substituted 3 membered heteroalkylene. The nanoparticle linker may be unsubstituted 3 membered heteroalkylene. In embodiments, the nanoparticle linker has formula:

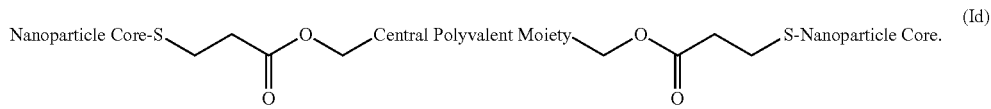

Each nanoparticle core may be further linked to additional nanoparticle linkers or capping linkers as described herein. Each central polyvalent moiety may have at least two nanoparticle linkers and/or capping linkers as described herein, including embodiments thereof.

The nanoparticle linker may be $R^5$-substituted or unsubstituted 2 to 20 membered heteroalkylene. The nanoparticle linker may be $R^5$-substituted or unsubstituted 2 to 15 membered heteroalkylene. The nanoparticle linker may be $R^5$-substituted or unsubstituted 2 to 10 membered heteroalkylene. The nanoparticle linker may be $R^5$-substituted or unsubstituted 2 to 5 membered heteroalkylene. The nanoparticle linker may be $R^5$-substituted or unsubstituted 2 to 3 membered heteroalkylene. The nanoparticle linker may be $R^5$-substituted or unsubstituted 3 to 8 membered heteroalkylene. The nanoparticle linker may be $R^5$-substituted or unsubstituted 2 to 20 membered heteroalkylene. The nanoparticle linker may be $R^5$-substituted or unsubstituted 3 to 6 membered heteroalkylene. The nanoparticle linker may be $R^5$-substituted or unsubstituted 3 to 5 membered heteroalkylene. The nanoparticle linker may be $R^5$-substituted or unsubstituted 6 membered heteroalkylene. The nanoparticle linker may be $R^5$-substituted 6 membered heteroalkylene. The nanoparticle linker may be $R^5$-substituted or unsubstituted 5 membered heteroalkylene. The nanoparticle linker may be $R^5$-substituted 5 membered heteroalkylene. The nanoparticle linker may be $R^5$-substituted or unsubstituted 4 membered heteroalkylene. The nanoparticle linker may be $R^5$-substituted 4 membered heteroalkylene. The nanoparticle linker may be $R^5$-substituted or unsubstituted 3 membered heteroalkylene. The nanoparticle linker may be $R^5$-substituted 3 membered heteroalkylene.

The nanoparticle linker may be substituted or unsubstituted 3 to 20 membered cycloalkylene. The nanoparticle linker may be substituted or unsubstituted 3 to 15 membered cycloalkylene. The nanoparticle linker may be substituted or unsubstituted 3 to 12 membered cycloalkylene. The nanoparticle linker may be substituted or unsubstituted 3 to 10 membered cycloalkylene. The nanoparticle linker may be substituted or unsubstituted 3 to 8 membered cycloalkylene. The nanoparticle linker may be substituted or unsubstituted 3 to 6 membered cycloalkylene. The nanoparticle linker may be substituted or unsubstituted 3 to 5 membered cycloalkylene. The nanoparticle linker may be substituted or unsubstituted 6 membered cycloalkylene. The nanoparticle linker may be substituted 6 membered cycloalkylene. The nanoparticle linker may be unsubstituted 6 membered cycloalkylene. The nanoparticle linker may be substituted or unsubstituted 5 membered cycloalkylene. The nanoparticle linker may be substituted 5 membered cycloalkylene. The nanoparticle linker may be unsubstituted 5 membered cycloalkylene. The nanoparticle linker may be substituted or unsubstituted 4 membered cycloalkylene. The nanoparticle linker may be substituted 4 membered cycloalkylene. The nanoparticle linker may be unsubstituted 4 membered cycloalkylene. The nanoparticle linker may be substituted or unsubstituted 3 membered cycloalkylene. The nanoparticle linker may be substituted 3 membered cycloalkylene. The nanoparticle linker may be unsubstituted 3 membered cycloalkylene.

The nanoparticle linker may be $R^5$-substituted or unsubstituted 3 to 20 membered cycloalkylene. The nanoparticle linker may be $R^5$-substituted or unsubstituted 3 to 15 membered cycloalkylene. The nanoparticle linker may be $R^5$-substituted or unsubstituted 3 to 12 membered cycloalkylene. The nanoparticle linker may be $R^5$-substituted or unsubstituted 3 to 10 membered cycloalkylene. The nanoparticle linker may be $R^5$-substituted or unsubstituted 3 to 8 membered cycloalkylene. The nanoparticle linker may be $R^5$-substituted or unsubstituted 3 to 6 membered cycloalkylene. The nanoparticle linker may be $R^5$-substituted or unsubstituted 3 to 5 membered cycloalkylene. The nanoparticle linker may be $R^5$-substituted or unsubstituted 6 membered cycloalkylene. The nanoparticle linker may be $R^5$-substituted 6 membered cycloalkylene. The nanoparticle linker may be $R^5$-substituted or unsubstituted 5 membered cycloalkylene. The nanoparticle linker may be $R^5$-substituted 5 membered cycloalkylene. The nanoparticle linker may be $R^5$-substituted or unsubstituted 4 membered cycloalkylene. The nanoparticle linker may be $R^5$-substituted 4 membered cycloalkylene. The nanoparticle linker may be $R^5$-substituted or unsubstituted 3 membered cycloalkylene. The nanoparticle linker may be $R^5$-substituted 3 membered cycloalkylene.

The nanoparticle linker may be substituted or unsubstituted 3 to 20 membered heterocycloalkylene. The nanoparticle linker may be substituted or unsubstituted 3 to 15 membered heterocycloalkylene. The nanoparticle linker may be substituted or unsubstituted 3 to 12 membered heterocycloalkylene. The nanoparticle linker may be substituted or unsubstituted 3 to 10 membered heterocycloalkylene. The nanoparticle linker may be substituted or unsubstituted 3 to 8 membered heterocycloalkylene. The nanoparticle linker may be substituted or unsubstituted 3 to 6 membered heterocycloalkylene. The nanoparticle linker may be substituted or unsubstituted 3 to 5 membered heterocycloalkylene. The nanoparticle linker may be substituted or unsubstituted 6 membered heterocycloalkylene. The nanoparticle linker may be substituted 6 membered heterocycloalkylene. The nanoparticle linker may be unsubstituted 6 membered heterocycloalkylene. The nanoparticle linker may be substituted or unsubstituted 5 membered heterocycloalkylene. The nanoparticle linker may be substituted 5 membered heterocycloalkylene. The nanoparticle linker may be unsubstituted 5 membered heterocycloalkylene. The nanoparticle linker may be substituted or unsubstituted 4 membered heterocycloalkylene. The nanoparticle linker may be substituted 4 membered heterocycloalkylene. The nanoparticle linker may be unsubstituted 4 membered heterocycloalkylene. The nanoparticle linker may be substituted or unsubstituted 3 membered heterocycloalkylene. The nanoparticle linker may be substituted 3 membered heterocycloalkylene. The nanoparticle linker may be unsubstituted 3 membered heterocycloalkylene.

The nanoparticle linker may be $R^5$-substituted or unsubstituted 3 to 20 membered heterocycloalkylene. The nanoparticle linker may be $R^5$-substituted or unsubstituted 3 to 15 membered heterocycloalkylene. The nanoparticle linker may be $R^5$-substituted or unsubstituted 3 to 12 membered heterocycloalkylene. The nanoparticle linker may be $R^5$-substituted or unsubstituted 3 to 10 membered heterocycloalkylene. The nanoparticle linker may be $R^5$-substituted or unsubstituted 3 to 8 membered heterocycloalkylene. The nanoparticle linker may be $R^5$-substituted or unsubstituted 3 to 6 membered heterocycloalkylene. The nanoparticle linker may be $R^5$-substituted or unsubstituted 3 to 5 membered heterocycloalkylene. The nanoparticle linker may be $R^5$-substituted or unsubstituted 6 membered heterocycloalkylene. The nanoparticle linker may be $R^5$-substituted 6 membered heterocycloalkylene. The nanoparticle linker may be $R^5$-substituted or unsubstituted 5 membered heterocycloalkylene. The nanoparticle linker may be $R^5$-substituted 5 membered heterocycloalkylene. The nanoparticle linker may be $R^5$-substituted or unsubstituted 4 membered heterocycloalkylene. The nanoparticle linker may be $R^5$-substituted 4 membered heterocycloalkylene. The nanoparticle linker may be $R^5$-substituted or unsubstituted 3 membered heterocycloalkylene. The nanoparticle linker may be $R^5$-substituted 3 membered heterocycloalkylene.

The nanoparticle linker may be substituted or unsubstituted 5 to 20 membered arylene. The nanoparticle linker may be substituted or unsubstituted 5 to 15 membered arylene. The nanoparticle linker may be substituted or unsubstituted 5 to 10 membered arylene. The nanoparticle linker may be substituted or unsubstituted 5 to 8 membered arylene. The nanoparticle linker may be substituted or unsubstituted 5 or 6 membered arylene. The nanoparticle linker may be substituted or unsubstituted 6 membered arylene. The nanoparticle linker may be substituted 6 membered arylene. The nanoparticle linker may be unsubstituted 6 membered arylene. The nanoparticle linker may be substituted or unsubstituted 5 membered arylene. The nanoparticle linker may be substituted 5 membered arylene. The nanoparticle linker may be unsubstituted 5 membered arylene.

The nanoparticle linker may be $R^5$-substituted or unsubstituted 5 to 20 membered arylene. The nanoparticle linker may be $R^5$-substituted or unsubstituted 5 to 15 membered arylene. The nanoparticle linker may be $R^5$-substituted or unsubstituted 5 to 10 membered arylene. The nanoparticle linker may be $R^5$-substituted or unsubstituted 5 to 8 membered arylene. The nanoparticle linker may be $R^5$-substituted or unsubstituted 5 or 6 membered arylene. The nanoparticle linker may be $R^5$-substituted or unsubstituted 6 membered arylene. The nanoparticle linker may be $R^5$-substituted 6 membered arylene. The nanoparticle linker may be $R^5$-substituted or unsubstituted 5 membered arylene. The nanoparticle linker may be $R^5$-substituted 5 membered arylene.

The nanoparticle linker may be substituted or unsubstituted 5 to 20 membered heteroarylene. The nanoparticle linker may be substituted or unsubstituted 5 to 15 membered heteroarylene. The nanoparticle linker may be substituted or unsubstituted 5 to 10 membered heteroarylene. The nanoparticle linker may be substituted or unsubstituted 5 to 8 membered heteroarylene. The nanoparticle linker may be substituted or unsubstituted 5 or 6 membered heteroarylene. The nanoparticle linker may be substituted or unsubstituted 6 membered heteroarylene. The nanoparticle linker may be substituted 6 membered heteroarylene. The nanoparticle linker may be unsubstituted 6 membered heteroarylene. The nanoparticle linker may be substituted or unsubstituted 5 membered heteroarylene. The nanoparticle linker may be substituted 5 membered heteroarylene. The nanoparticle linker may be unsubstituted 5 membered heteroarylene.

The nanoparticle linker may be $R^5$-substituted or unsubstituted 5 to 20 membered heteroarylene. The nanoparticle linker may be $R^5$-substituted or unsubstituted 5 to 15 membered heteroarylene. The nanoparticle linker may be $R^5$-substituted or unsubstituted 5 to 10 membered heteroarylene. The nanoparticle linker may be $R^5$-substituted or unsubstituted 5 to 8 membered heteroarylene. The nanoparticle linker may be $R^5$-substituted or unsubstituted 5 or 6 membered heteroarylene. The nanoparticle linker may be $R^5$-substituted or unsubstituted 6 membered heteroarylene. The nanoparticle linker may be $R^5$-substituted 6 membered heteroarylene. The nanoparticle linker may be $R^5$-substituted or unsubstituted 5 membered heteroarylene. The nanoparticle linker may be $R^5$-substituted 5 membered heteroarylene.

The nanoparticle linker may be substituted or unsubstituted $C_1$-$C_5$ alkylene, 2 to 5 membered heteroalkylene, or an amino acid sequence linker. The nanoparticle linker may be an amino acid sequence linker. The amino acid sequence may be recognized by an enzyme. The enzyme may be an esterase that recognizes an ester bond. The nanoparticle linker may be a nucleic acid sequence linker.

$R^5$ is halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, $R^6$-substituted or unsubstituted alkyl (e.g. $C_1$-$C_8$ alkyl), $R^6$-substituted or unsubstituted heteroalkyl (e.g. 2 to 8 membered heteroalkyl), $R^6$-substituted or unsubstituted cycloalkyl (e.g. $C_3$-$C_8$ cycloalkyl), $R^6$-substituted or unsubstituted heterocycloalkyl (e.g. 3 to 6 membered heterocycloalkyl), $R^6$-substituted or unsubstituted aryl (e.g. 5 or 6 membered aryl), or $R^6$-substituted or unsubstituted heteroaryl (e.g. 5 or 6 membered heteroaryl).

$R^6$ is halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, unsubstituted alkyl (e.g. $C_1$-$C_8$ alkyl), heteroalkyl (e.g. 2 to 8 membered heteroalkyl), unsubstituted cycloalkyl (e.g. $C_3$-$C_8$ cycloalkyl), unsubstituted heterocycloalkyl (e.g. 3 to 6 membered heterocycloalkyl), unsubstituted aryl (e.g. 5 or 6 membered aryl), or unsubstituted heteroaryl (e.g. 5 or 6 membered heteroaryl).

The capping linker may be C(O)—, —C(O)O—, —O—, —S—, —NH—, —$NR^1$—, —C(O)$NR^2$—, —S(O)$_n$—, —S(O)$NR^3$—, —OP(O)(O$R^4$)O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, an amino acid sequence linker, or a nucleic acid sequence linker. $R^1$, $R^2$, $R^3$, and $R^4$ are as described herein, including embodiments thereof. The symbol n is as described herein, including embodiments thereof.

The capping linker may be —O—, —S—, C(O)O—, —$SO_2$—, or —NH—. The capping linker may be —O—, —S—, C(O)O—, or —NH—. The capping linker may be substituted or unsubstituted $C_1$-$C_{20}$ alkylene. The capping linker may be substituted or unsubstituted $C_1$-$C_{15}$ alkylene. The capping linker may be substituted or unsubstituted $C_1$-$C_{10}$ alkylene. The capping linker may be substituted or unsubstituted $C_1$-$C_5$ alkylene. The capping linker may be substituted or unsubstituted $C_1$-$C_3$ alkylene. The capping linker may be substituted or unsubstituted $C_3$-$C_8$ alkylene. The capping linker may be substituted or unsubstituted $C_3$-$C_6$ alkylene. The capping linker may be substituted or unsubstituted $C_3$-$C_5$ alkylene. The capping linker may be substituted or unsubstituted $C_6$ alkylene. The capping linker may be substituted or unsubstituted $C_5$ alkylene. The capping linker may be substituted or unsubstituted $C_4$ alkylene. The capping linker may be substituted or unsubstituted $C_3$ alkylene. The capping linker may be substituted or unsubstituted $C_2$ alkylene.

The capping linker may be $R^7$-substituted or unsubstituted $C_1$-$C_{20}$ alkylene. The capping linker may be $R^7$-substituted or unsubstituted $C_1$-$C_{15}$ alkylene. The capping linker may be $R^7$-substituted or unsubstituted $C_1$-$C_{10}$ alkylene. The capping linker may be $R^7$-substituted or unsubstituted $C_1$-$C_5$ alkylene. The capping linker may be $R^7$-substituted or unsubstituted $C_1$-$C_3$ alkylene. The capping linker may be $R^7$-substituted or unsubstituted $C_3$-$C_8$ alkylene. The capping linker may be $R^7$-substituted or unsubstituted $C_3$-$C_6$ alkylene. The capping linker may be $R^7$-substituted or unsubstituted $C_3$-$C_5$ alkylene. The capping linker may be $R^7$-substituted or unsubstituted $C_6$ alkylene. The capping linker may be $R^7$-substituted or unsubstituted $C_5$ alkylene. The capping linker may be $R^7$-substituted or unsubstituted $C_4$ alkylene. The capping linker may be $R^7$-substituted or unsubstituted $C_3$ alkylene. The capping linker may be $R^7$-substituted or unsubstituted $C_2$ alkylene.

The capping linker may have, for example, formula:

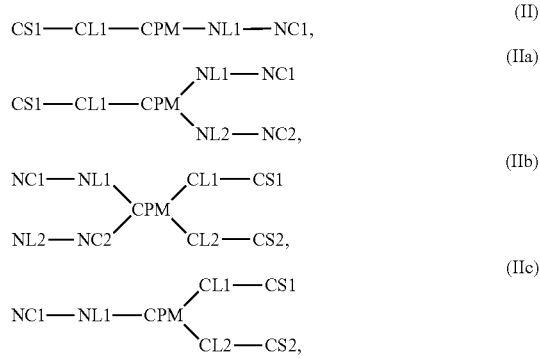

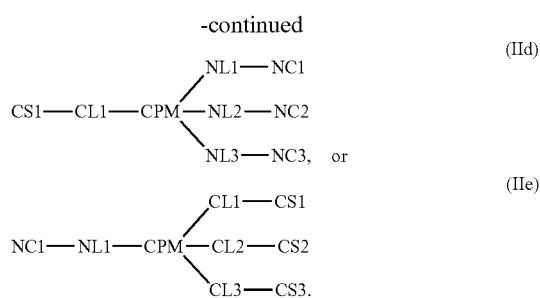

NC1 is a first nanoparticle core and NC2 is a second nanoparticle core. CS1 is a first capping substituent and CS2 is a second capping substituent. CL1 is a first capping linker and CL2 is a second capping linker. CPM is a central polyvalent moiety. NL1 is a first nanoparticle linker and NL2 is a second nanoparticle linker. Each nanoparticle core may be further linked to additional nanoparticle linkers or capping linkers as described herein. Each central polyvalent moiety may have at least two nanoparticle linkers and/or capping linkers as described herein, including embodiments thereof.

The capping linker may be substituted or unsubstituted 2 to 20 membered heteroalkylene. The capping linker may be substituted or unsubstituted 2 to 15 membered heteroalkylene. The capping linker may be substituted or unsubstituted 2 to 10 membered heteroalkylene. The capping linker may be substituted or unsubstituted 2 to 5 membered heteroalkylene. The capping linker may be substituted or unsubstituted 2 to 3 membered heteroalkylene. The capping linker may be substituted or unsubstituted 3 to 8 membered heteroalkylene. The capping linker may be substituted or unsubstituted 2 to 20 membered heteroalkylene. The capping linker may be substituted or unsubstituted 3 to 6 membered heteroalkylene. The capping linker may be substituted or unsubstituted 3 to 5 membered heteroalkylene. The capping linker may be substituted or unsubstituted 6 membered heteroalkylene. The capping linker may be substituted 6 membered heteroalkylene. The capping linker may be unsubstituted 6 membered heteroalkylene. The capping linker may be substituted or unsubstituted 5 membered heteroalkylene. The capping linker may be substituted 5 membered heteroalkylene. The capping linker may be unsubstituted 5 membered heteroalkylene. The capping linker may be substituted or unsubstituted 4 membered heteroalkylene. The capping linker may be substituted 4 membered heteroalkylene. The capping linker may be unsubstituted 4 membered heteroalkylene. The capping linker may be substituted or unsubstituted 3 membered heteroalkylene. The capping linker may be substituted or unsubstituted 3 membered heteroalkylene. The capping linker may be unsubstituted 3 membered heteroalkylene. In embodiments, the capping linker has formula:

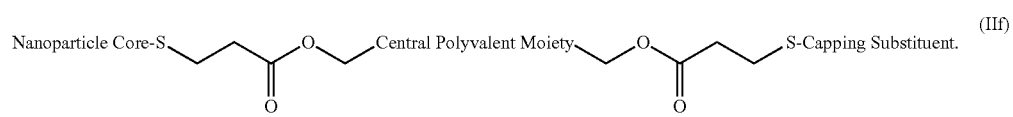

Each nanoparticle core may be further linked to additional nanoparticle linkers or capping linkers as described herein. Each central polyvalent moiety may have at least two nanoparticle linkers and/or capping linkers as described herein, including embodiments thereof.

The capping linker may be $R^7$-substituted or unsubstituted 2 to 20 membered heteroalkylene. The capping linker may be $R^7$-substituted or unsubstituted 2 to 15 membered heteroalkylene. The capping linker may be $R^7$-substituted or unsubstituted 2 to 10 membered heteroalkylene. The capping linker may be $R^7$-substituted or unsubstituted 2 to 5 membered heteroalkylene. The capping linker may be $R^7$-substituted or unsubstituted 2 to 3 membered heteroalkylene. The capping linker may be $R^7$-substituted or unsubstituted 3 to 8 membered heteroalkylene. The capping linker may be $R^7$-substituted or unsubstituted 2 to 20 membered heteroalkylene. The capping linker may be $R^7$-substituted or unsubstituted 3 to 6 membered heteroalkylene. The capping linker may be $R^7$-substituted or unsubstituted 3 to 5 membered heteroalkylene. The capping linker may be $R^7$-substituted or unsubstituted 6 membered heteroalkylene. The capping linker may be $R^7$-substituted 6 membered heteroalkylene. The capping linker may be $R^7$-substituted or unsubstituted 5 membered heteroalkylene. The capping linker may be $R^7$-substituted 5 membered heteroalkylene. The capping linker may be $R^7$-substituted or unsubstituted 4 membered heteroalkylene. The capping linker may be $R^7$-substituted 4 membered heteroalkylene. The capping linker may be $R^7$-substituted or unsubstituted 3 membered heteroalkylene. The capping linker may be $R^7$-substituted 3 membered heteroalkylene.

The capping linker may be substituted or unsubstituted 3 to 20 membered cycloalkylene. The capping linker may be substituted or unsubstituted 3 to 15 membered cycloalkylene. The capping linker may be substituted or unsubstituted 3 to 12 membered cycloalkylene. The capping linker may be substituted or unsubstituted 3 to 10 membered cycloalkylene. The capping linker may be substituted or unsubstituted 3 to 8 membered cycloalkylene. The capping linker may be substituted or unsubstituted 3 to 6 membered cycloalkylene. The capping linker may be substituted or unsubstituted 3 to 5 membered cycloalkylene. The capping linker may be substituted or unsubstituted 6 membered cycloalkylene. The capping linker may be substituted 6 membered cycloalkylene. The capping linker may be unsubstituted 6 membered cycloalkylene. The capping linker may be substituted or unsubstituted 5 membered cycloalkylene. The capping linker may be substituted 5 membered cycloalkylene. The capping linker may be unsubstituted 5 membered cycloalkylene. The capping linker may be substituted or unsubstituted 4 membered cycloalkylene. The capping linker may be substituted 4 membered cycloalkylene. The capping linker may be unsubstituted 4 membered cycloalkylene. The capping linker may be substituted or unsubstituted 3 membered cycloalkylene. The capping linker may be substituted 3 membered cycloalkylene. The capping linker may be unsubstituted 3 membered cycloalkylene.

The capping linker may be $R^7$-substituted or unsubstituted 3 to 20 membered cycloalkylene. The capping linker may be $R^7$-substituted or unsubstituted 3 to 15 membered cycloalkylene. The capping linker may be $R^7$-substituted or unsubstituted 3 to 12 membered cycloalkylene. The capping linker may be $R^7$-substituted or unsubstituted 3 to 10 membered cycloalkylene. The capping linker may be $R^7$-substituted or unsubstituted 3 to 8 membered cycloalkylene. The capping linker may be $R^7$-substituted or unsubstituted 3 to 6 membered cycloalkylene. The capping linker may be $R^7$-substituted or unsubstituted 3 to 5 membered cycloalkylene. The capping linker may be $R^7$-substituted or unsubstituted 6 membered cycloalkylene. The capping linker may be $R^7$-substituted 6 membered cycloalkylene. The capping linker may be $R^7$-substituted or unsubstituted 5 membered cycloalkylene. The capping linker may be $R^7$-substituted 5 membered cycloalkylene. The capping linker may be $R^7$-substituted or unsubstituted 4 membered cycloalkylene. The capping linker may be $R^7$-substituted or unsubstituted 3 membered cycloalkylene. The capping linker may be $R^7$-substituted 3 membered cycloalkylene.

The capping linker may be substituted or unsubstituted 3 to 20 membered heterocycloalkylene. The capping linker may be substituted or unsubstituted 3 to 15 membered heterocycloalkylene. The capping linker may be substituted or unsubstituted 3 to 12 membered heterocycloalkylene. The capping linker may be substituted or unsubstituted 3 to 10 membered heterocycloalkylene. The capping linker may be substituted or unsubstituted 3 to 8 membered heterocycloalkylene. The capping linker may be substituted or unsubstituted 3 to 6 membered heterocycloalkylene. The capping linker may be substituted or unsubstituted 3 to 5 membered heterocycloalkylene. The capping linker may be substituted or unsubstituted 6 membered heterocycloalkylene. The capping linker may be substituted 6 membered heterocycloalkylene. The capping linker may be unsubstituted 6 membered heterocycloalkylene. The capping linker may be substituted or unsubstituted 5 membered heterocycloalkylene. The capping linker may be substituted 5 membered heterocycloalkylene. The capping linker may be unsubstituted 5 membered heterocycloalkylene. The capping linker may be substituted or unsubstituted 4 membered heterocycloalkylene. The capping linker may be substituted 4 membered heterocycloalkylene. The capping linker may be unsubstituted 4 membered heterocycloalkylene. The capping linker may be substituted or unsubstituted 3 membered heterocycloalkylene. The capping linker may be substituted 3 membered heterocycloalkylene. The capping linker may be unsubstituted 3 membered heterocycloalkylene.

The capping linker may be $R^7$-substituted or unsubstituted 3 to 20 membered heterocycloalkylene. The capping linker may be $R^7$-substituted or unsubstituted 3 to 15 membered heterocycloalkylene. The capping linker may be $R^7$-substituted or unsubstituted 3 to 12 membered heterocycloalkylene. The capping linker may be $R^7$-substituted or unsubstituted 3 to 10 membered heterocycloalkylene. The capping linker may be $R^7$-substituted or unsubstituted 3 to 8 membered heterocycloalkylene. The capping linker may be $R^7$-substituted or unsubstituted 3 to 6 membered heterocycloalkylene. The capping linker may be $R^7$-substituted or unsubstituted 3 to 5 membered heterocycloalkylene. The capping linker may be $R^7$-substituted or unsubstituted 6 membered heterocycloalkylene. The capping linker may be $R^7$-substituted 6 membered heterocycloalkylene. The capping linker may be $R^7$-substituted or unsubstituted 5 membered heterocycloalkylene. The capping linker may be $R^7$-substituted 5 membered heterocycloalkylene. The capping linker may be $R^7$-substituted or unsubstituted 4 membered heterocycloalkylene. The capping linker may be $R^7$-substituted 4 membered heterocycloalkylene. The capping linker may be $R^7$-substituted or unsubstituted 3 membered heterocycloalkylene. The capping linker may be $R^7$-substituted 3 membered heterocycloalkylene.

The capping linker may be substituted or unsubstituted 5 to 20 membered arylene. The capping linker may be substituted or unsubstituted 5 to 15 membered arylene. The capping linker may be substituted or unsubstituted 5 to 10 membered arylene. The capping linker may be substituted or unsubstituted 5 to 8 membered arylene. The capping linker may be substituted or unsubstituted 5 or 6 membered arylene. The capping linker may be substituted or unsubstituted 6 membered arylene. The capping linker may be substituted 6 membered arylene. The capping linker may be unsubstituted 6 membered arylene. The capping linker may be substituted or unsubstituted 5 membered arylene. The capping linker may be substituted 5 membered arylene. The capping linker may be unsubstituted 5 membered arylene.

The capping linker may be $R^7$-substituted or unsubstituted 5 to 20 membered arylene. The capping linker may be $R^7$-substituted or unsubstituted 5 to 15 membered arylene. The capping linker may be $R^7$-substituted or unsubstituted 5 to 10 membered arylene. The capping linker may be $R^7$-substituted or unsubstituted 5 to 8 membered arylene. The capping linker may be $R^7$-substituted or unsubstituted 5 or 6 membered arylene. The capping linker may be $R^7$-substituted or unsubstituted 6 membered arylene. The capping linker may be $R^7$-substituted 6 membered arylene. The capping linker may be $R^7$-substituted or unsubstituted 5 membered arylene. The capping linker may be $R^7$-substituted 5 membered arylene.

The capping linker may be substituted or unsubstituted 5 to 20 membered heteroarylene. The capping linker may be substituted or unsubstituted 5 to 15 membered heteroarylene. The capping linker may be substituted or unsubstituted 5 to 10 membered heteroarylene. The capping linker may be substituted or unsubstituted 5 to 8 membered heteroarylene. The capping linker may be substituted or unsubstituted 5 or 6 membered heteroarylene. The capping linker may be substituted or unsubstituted 6 membered heteroarylene. The capping linker may be substituted 6 membered heteroarylene. The capping linker may be unsubstituted 6 membered heteroarylene. The capping linker may be substituted or unsubstituted 5 membered heteroarylene. The capping linker may be substituted 5 membered heteroarylene. The capping linker may be unsubstituted 5 membered heteroarylene.

The capping linker may be $R^7$-substituted or unsubstituted 5 to 20 membered heteroarylene. The capping linker may be $R^7$-substituted or unsubstituted 5 to 15 membered heteroarylene. The capping linker may be $R^7$-substituted or unsubstituted 5 to 10 membered heteroarylene. The capping linker may be $R^7$-substituted or unsubstituted 5 to 8 membered heteroarylene. The capping linker may be $R^7$-substituted or unsubstituted 5 or 6 membered heteroarylene. The capping linker may be $R^7$-substituted or unsubstituted 6 membered heteroarylene. The capping linker may be $R^7$-substituted 6 membered heteroarylene. The capping linker may be $R^7$-substituted or unsubstituted 5 membered heteroarylene. The capping linker may be $R^7$-substituted 5 membered heteroarylene.

$R^7$ is halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, $R^8$-substituted or unsubstituted alkyl (e.g. $C_1$-$C_8$ alkyl), $R^8$-substituted or unsubstituted heteroalkyl (e.g. 2 to 8 membered heteroalkyl), $R^8$-substituted or unsubstituted cycloalkyl (e.g. $C_3$-$C_8$ cycloalkyl), $R^8$-substituted or unsubstituted heterocycloalkyl (e.g. 3 to 6 membered heterocycloalkyl), $R^8$-substituted or unsubstituted aryl (e.g. 5 or 6 membered aryl), or $R^8$-substituted or unsubstituted heteroaryl (e.g. 5 or 6 membered heteroaryl).

$R^8$ is halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, unsubstituted alkyl (e.g. $C_1$-$C_8$ alkyl), heteroalkyl (e.g. 2 to 8 membered heteroalkyl), unsubstituted cycloalkyl (e.g. $C_3$-$C_8$ cycloalkyl), unsubstituted heterocycloalkyl (e.g. 3 to 6 membered heterocycloalkyl), unsubstituted aryl (e.g. 5 or 6 membered aryl), or unsubstituted heteroaryl (e.g. 5 or 6 membered heteroaryl).

The capping linker may be substituted or unsubstituted $C_1$-$C_5$ alkylene, 2 to 5 membered heteroalkylene, or an amino acid sequence linker. The capping linker may be an amino acid sequence linker. The amino acid sequence may be recognized by an enzyme. The enzyme may be an esterase that recognizes an ester bond. The capping linker may be a nucleic acid sequence linker.

The exterior polyvalent linker may include at least three nanoparticle linkers and capping linkers combined. The exterior polyvalent linker may include at least four nanoparticle linkers and capping linkers combined. The interior polyvalent linker may include at least three nanoparticle linkers. The interior polyvalent linker may include at least four nanoparticle linkers. The nanoparticle linkers and capping linkers may be as described herein, including embodiments thereof.

The nanoparticle linker may include a nanoparticle-linker-cleavage site. When the nanoparticle linker includes a nanoparticle-linker-cleavage site, the nanoparticle-linker-cleavage site may be located at the juncture between the nanoparticle linker and the nanoparticle core, the juncture between the nanoparticle linker and the central polyvalent moiety, or at a location between the juncture of the nanoparticle linker and nanoparticle core and the juncture between the nanoparticle linker and the central polyvalent moiety. The nanoparticle-linker-cleavage site may be located at the juncture of nanoparticle linker and the nanoparticle core. The nanoparticle-linker-cleavage site may be located at the juncture of the nanoparticle linker and the central polyvalent linker. The nanoparticle-linker-cleavage site may be located between the juncture of the nanoparticle linker and nanoparticle core and the juncture between the nanoparticle linker and the central polyvalent moiety.

The capping linker may include a capping linker-cleavage site. When the capping linker includes a capping linker-cleavage site, the capping linker-cleavage site may be located at the juncture between the capping linker and the capping substituent, the juncture between the capping linker and the central polyvalent moiety, or at a location between the juncture of the capping linker and capping substituent and the juncture between the capping linker and the central polyvalent moiety. The capping linker-cleavage site may be located at the juncture of capping linker and the capping substituent. The capping linker-cleavage site may be located at the juncture of the capping linker and the central polyvalent linker. The capping linker-cleavage site may be located between the juncture of the capping linker and capping substituent and the juncture between the capping linker and the central polyvalent moiety.

The nanoparticle linker may include nanoparticle linker-cleavage site and the capping linker may include a capping linker-cleavage site. The nanoparticle linker-cleavage site and capping linker-cleavage cleavage site may be identical. The nanoparticle linker-cleavage site and capping linker-cleavage cleavage site may be different. When the cleavage sites are different, they may be orthogonal.

The nanoparticle linker-cleavage site and capping linker-cleavage site may independently be a metal cleavage site (e.g. a site cleaved via a metal-catalyzed reaction), an acid cleavage site (e.g. a site cleaved via an acid-catalyzed reaction), a base cleave site (e.g. a site cleaved via a base-catalyzed reaction), an enzyme cleavage site (e.g. a site cleaved via an enzyme-catalyzed reaction), or a photo-cleavage site (e.g. a site cleaved via photo-catalyzed reaction). When the nanoparticle linker-cleavage site is an enzyme cleavage site, the nanoparticle linker-cleavage site may include an ester (e.g. —C(O)O—) recognized by an esterase. When the capping linker-cleavage site is an enzyme cleavage site, the capping linker-cleavage site may include an ester (e.g. —C(O)O—) recognized by an esterase.

The nanoparticle linker-cleavage site and capping linker-cleavage site may independently be —C(O)—, —C(O)O—, —O—, —S—, —NH—, —$NR^1$—, —$C(O)NR^2$—, —$S(O)_n$—, —$S(O)NR^3$—, —$OP(O)(OR^4)O$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, an amino acid sequence, or a nucleic acid sequence. $R^1$, $R^2$, $R^3$, and $R^4$ are as described herein, including embodiments thereof. The symbol n is as described herein, including embodiments thereof.

The nanoparticle linker-cleavage site may be —O—, —S—, C(O)O—, —$SO_2$—, or —NH—. The nanoparticle linker-cleavage site may be —O—, —S—, C(O)O—, or —NH—. The nanoparticle linker-cleavage site may be substituted or unsubstituted $C_1$-$C_{20}$ alkylene. The nanoparticle linker-cleavage site may be substituted or unsubstituted $C_1$-$C_{15}$ alkylene. The nanoparticle linker-cleavage site may be substituted or unsubstituted $C_1$-$C_{10}$ alkylene. The nanoparticle linker-cleavage site may be substituted or unsubstituted $C_1$-$C_5$ alkylene. The nanoparticle linker-cleavage site may be substituted or unsubstituted $C_1$-$C_3$ alkylene. The nanoparticle linker-cleavage site may be substituted or unsubstituted $C_3$-$C_8$ alkylene. The nanoparticle linker-cleavage site may be substituted or unsubstituted $C_3$-$C_6$ alkylene. The nanoparticle linker-cleavage site may be substituted or unsubstituted $C_3$-$C_5$ alkylene. The nanoparticle linker-cleavage site may be substituted or unsubstituted $C_6$ alkylene. The nanoparticle linker-cleavage site may be substituted or unsubstituted $C_5$ alkylene. The nanoparticle linker-cleavage site may be substituted or unsubstituted $C_4$ alkylene. The nanoparticle linker-cleavage site may be substituted or unsubstituted $C_3$ alkylene. The nanoparticle linker-cleavage site may be substituted or unsubstituted $C_2$ alkylene.

The nanoparticle linker-cleavage site may be $R^9$-substituted or unsubstituted $C_1$-$C_{20}$ alkylene. The nanoparticle linker-cleavage site may be $R^9$-substituted or unsubstituted $C_1$-$C_{15}$ alkylene. The nanoparticle linker-cleavage site may be $R^9$-substituted or unsubstituted $C_1$-$C_{10}$ alkylene. The nanoparticle linker-cleavage site may be $R^9$-substituted or unsubstituted $C_1$-$C_5$ alkylene. The nanoparticle linker-cleavage site may be $R^9$-substituted or unsubstituted $C_1$-$C_3$ alkylene. The nanoparticle linker-cleavage site may be $R^9$-substituted or unsubstituted $C_3$-$C_8$ alkylene. The nanoparticle linker-cleavage site may be $R^9$-substituted or unsubstituted $C_3$-$C_6$ alkylene. The nanoparticle linker-cleavage site may be $R^9$-substituted or unsubstituted $C_3$-$C_5$ alkylene. The nanoparticle linker-cleavage site may be $R^9$-substituted or unsubstituted $C_6$ alkylene. The nanoparticle linker-cleavage site may be $R^9$-substituted or unsubstituted $C_5$ alkylene. The nanoparticle linker-cleavage site may be $R^9$-substituted or unsubstituted $C_4$ alkylene. The nanoparticle linker-cleavage site may be $R^9$-substituted or unsubstituted $C_3$ alkylene. The nanoparticle linker-cleavage site may be $R^9$-substituted or unsubstituted $C_2$ alkylene.

The nanoparticle linker-cleavage site may be substituted or unsubstituted 2 to 20 membered heteroalkylene. The nanoparticle linker-cleavage site may be substituted or unsubstituted 2 to 15 membered heteroalkylene. The nanoparticle linker-cleavage site may be substituted or unsubstituted 2 to 10 membered heteroalkylene. The nanoparticle linker-cleavage site may be substituted or unsubstituted 2 to 5 membered heteroalkylene. The nanoparticle linker-cleavage site may be substituted or unsubstituted 2 to 3 membered heteroalkylene. The nanoparticle linker-cleavage site may be substituted or unsubstituted 3 to 8 membered heteroalkylene. The nanoparticle linker-cleavage site may be substituted or unsubstituted 2 to 20 membered heteroalkylene. The nanoparticle linker-cleavage site may be substituted or unsubstituted 3 to 6 membered heteroalkylene. The nanoparticle linker-cleavage site may be substituted or unsubstituted 3 to 5 membered heteroalkylene. The nanoparticle linker-cleavage site may be substituted or unsubstituted 6 membered heteroalkylene. The nanoparticle linker-cleavage site may be substituted 6 membered heteroalkylene. The nanoparticle linker-cleavage site may be unsubstituted 6 membered heteroalkylene. The nanoparticle linker-cleavage site may be substituted or unsubstituted 5 membered heteroalkylene. The nanoparticle linker-cleavage site may be substituted 5 membered heteroalkylene. The nanoparticle linker-cleavage site may be unsubstituted 5 membered heteroalkylene. The nanoparticle linker-cleavage site may be substituted or unsubstituted 4 membered heteroalkylene. The nanoparticle linker-cleavage site may be substituted 4 membered heteroalkylene. The nanoparticle linker-cleavage site may be unsubstituted 4 membered heteroalkylene. The nanoparticle linker-cleavage site may be substituted or unsubstituted 3 membered heteroalkylene. The nanoparticle linker-cleavage site may be substituted 3 membered heteroalkylene. The nanoparticle linker-cleavage site may be unsubstituted 3 membered heteroalkylene. The nanoparticle linker-cleavage site may be a substituted or unsubstituted heteroalkylene including an ester moiety (e.g. —C(O)O—). The ester may be recognized by an enzyme, for example, an esterase.

The nanoparticle linker-cleavage site may be $R^9$-substituted or unsubstituted 2 to 20 membered heteroalkylene. The nanoparticle linker-cleavage site may be $R^9$-substituted or unsubstituted 2 to 15 membered heteroalkylene. The nanoparticle linker-cleavage site may be $R^9$-substituted or unsubstituted 2 to 10 membered heteroalkylene. The nanoparticle linker-cleavage site may be $R^9$-substituted or unsubstituted 2 to 5 membered heteroalkylene. The nanoparticle linker-cleavage site may be $R^9$-substituted or unsubstituted 2 to 3 membered heteroalkylene. The nanoparticle linker-cleavage site may be $R^9$-substituted or unsubstituted 3 to 8 membered heteroalkylene. The nanoparticle linker-cleavage site may be $R^9$-substituted or unsubstituted 2 to 20 membered heteroalkylene. The nanoparticle linker-cleavage site may be $R^9$-substituted or unsubstituted 3 to 6 membered heteroalkylene. The nanoparticle linker-cleavage site may be $R^9$-substituted or unsubstituted 3 to 5 membered heteroalkylene. The nanoparticle linker-cleavage site may be $R^9$-substituted or unsubstituted 6 membered heteroalkylene. The nanoparticle linker-cleavage site may be $R^9$-substituted 6 membered heteroalkylene. The nanoparticle linker-cleavage site may be $R^9$-substituted or unsubstituted 5 membered heteroalkylene. The nanoparticle linker-cleavage site may be $R^9$-substituted 5 membered heteroalkylene. The nanoparticle linker-cleavage site may be $R^9$-substituted or unsubstituted 4 membered heteroalkylene. The nanoparticle linker-cleavage site may be $R^9$-substituted 4 membered heteroalkylene. The nanoparticle linker-cleavage site may be $R^9$-substituted or unsubstituted 3 membered heteroalkylene. The nanoparticle linker-cleavage site may be $R^9$-substituted 3 membered heteroalkylene.

The nanoparticle linker-cleavage site may be substituted or unsubstituted 3 to 20 membered cycloalkylene. The nanoparticle linker-cleavage site may be substituted or unsubstituted 3 to 15 membered cycloalkylene. The nanoparticle linker-cleavage site may be substituted or unsubstituted 3 to 12 membered cycloalkylene. The nanoparticle linker-cleavage site may be substituted or unsubstituted 3 to 10 membered cycloalkylene. The nanoparticle linker-cleavage site may be substituted or unsubstituted 3 to 8 membered cycloalkylene. The nanoparticle linker-cleavage site may be substituted or unsubstituted 3 to 6 membered cycloalkylene. The nanoparticle linker-cleavage site may be substituted or unsubstituted 3 to 5 membered cycloalkylene. The nanoparticle linker-cleavage site may be substituted or unsubstituted 6 membered cycloalkylene. The nanoparticle linker-cleavage site may be substituted 6 membered cycloalkylene. The nanoparticle linker-cleavage site may be unsubstituted 6 membered cycloalkylene. The nanoparticle linker-cleavage site may be substituted or unsubstituted 5 membered cycloalkylene. The nanoparticle linker-cleavage site may be substituted 5 membered cycloalkylene. The nanoparticle linker-cleavage site may be unsubstituted 5 membered cycloalkylene. The nanoparticle linker-cleavage site may be substituted or unsubstituted 4 membered cycloalkylene. The nanoparticle linker-cleavage site may be substituted 4 membered cycloalkylene. The nanoparticle linker-cleavage site may be unsubstituted 4 membered cycloalkylene. The nanoparticle linker-cleavage site may be substituted or unsubstituted 3 membered cycloalkylene. The nanoparticle linker-cleavage site may be substituted 3 membered cycloalkylene. The nanoparticle linker-cleavage site may be unsubstituted 3 membered cycloalkylene.

The nanoparticle linker-cleavage site may be $R^9$-substituted or unsubstituted 3 to 20 membered cycloalkylene. The nanoparticle linker-cleavage site may be $R^9$-substituted or unsubstituted 3 to 15 membered cycloalkylene. The nanoparticle linker-cleavage site may be $R^9$-substituted or unsubstituted 3 to 12 membered cycloalkylene. The nanoparticle linker-cleavage site may be $R^9$-substituted or unsubstituted 3 to 10 membered cycloalkylene. The nanoparticle linker-cleavage site may be $R^9$-substituted or unsubstituted 3 to 8 membered cycloalkylene. The nanoparticle linker-cleavage site may be $R^9$-substituted or unsubstituted 3 to 6 membered cycloalkylene. The nanoparticle linker-cleavage site may be $R^9$-substituted or unsubstituted 3 to 5 membered cycloalkylene. The nanoparticle linker-cleavage site may be $R^9$-substituted 6 membered cycloalkylene. The nanoparticle linker-cleavage site may be $R^9$-substituted or unsubstituted 5 membered cycloalkylene. The nanoparticle linker-cleavage site may be $R^9$-substituted 5 membered cycloalkylene. The nanoparticle linker-cleavage site may be $R^9$-substituted or unsubstituted 4 membered cycloalkylene. The nanoparticle linker-cleavage site may be $R^9$-substituted 4 membered cycloalkylene. The nanoparticle linker-cleavage site may be $R^9$-substituted or unsubstituted 3 membered cycloalkylene. The nanoparticle linker-cleavage site may be $R^9$-substituted 3 membered cycloalkylene.

The nanoparticle linker-cleavage site may be substituted or unsubstituted 3 to 20 membered heterocycloalkylene. The nanoparticle linker-cleavage site may be substituted or unsubstituted 3 to 15 membered heterocycloalkylene. The nanoparticle linker-cleavage site may be substituted or unsubstituted 3 to 12 membered heterocycloalkylene. The nanoparticle linker-cleavage site may be substituted or unsubstituted 3 to 10 membered heterocycloalkylene. The nanoparticle linker-cleavage site may be substituted or unsubstituted 3 to 8 membered heterocycloalkylene. The nanoparticle linker-cleavage site may be substituted or unsubstituted 3 to 6 membered heterocycloalkylene. The nanoparticle linker-cleavage site may be substituted or unsubstituted 3 to 5 membered heterocycloalkylene. The nanoparticle linker-cleavage site may be substituted or unsubstituted 6 membered heterocycloalkylene. The nanoparticle linker-cleavage site may be substituted 6 membered heterocycloalkylene. The nanoparticle linker-cleavage site may be unsubstituted 6 membered heterocycloalkylene. The nanoparticle linker-cleavage site may be substituted or unsubstituted 5 membered heterocycloalkylene. The nanoparticle linker-cleavage site may be substituted 5 membered heterocycloalkylene. The nanoparticle linker-cleavage site may be unsubstituted 5 membered heterocycloalkylene. The nanoparticle linker-cleavage site may be substituted or unsubstituted 4 membered heterocycloalkylene. The nanoparticle linker-cleavage site may be substituted 4 membered heterocycloalkylene. The nanoparticle linker-cleavage site may be unsubstituted 4 membered heterocycloalkylene. The nanoparticle linker-cleavage site may be substituted or unsubstituted 3 membered heterocycloalkylene. The nanoparticle linker-cleavage site may be substituted 3 membered heterocycloalkylene. The nanoparticle linker-cleavage site may be unsubstituted 3 membered heterocycloalkylene.

The nanoparticle linker-cleavage site may be $R^9$-substituted or unsubstituted 3 to 20 membered heterocycloalkylene. The nanoparticle linker-cleavage site may be $R^9$-substituted or unsubstituted 3 to 15 membered heterocycloalkylene. The nanoparticle linker-cleavage site may be $R^9$-substituted or unsubstituted 3 to 12 membered heterocycloalkylene. The nanoparticle linker-cleavage site may be $R^9$-substituted or unsubstituted 3 to 10 membered heterocycloalkylene. The nanoparticle linker-cleavage site may be $R^9$-substituted or unsubstituted 3 to 8 membered heterocycloalkylene. The nanoparticle linker-cleavage site may be $R^9$-substituted or unsubstituted 3 to 6 membered heterocycloalkylene. The nanoparticle linker-cleavage site may be $R^9$-substituted or unsubstituted 3 to 5 membered heterocycloalkylene. The nanoparticle linker-cleavage site may be $R^9$-substituted or unsubstituted 6 membered heterocycloalkylene. The nanoparticle linker-cleavage site may be $R^9$-substituted 6 membered heterocycloalkylene. The nanoparticle linker-cleavage site may be $R^9$-substituted or unsubstituted 5 membered heterocycloalkylene. The nanoparticle linker-cleavage site may be $R^9$-substituted 5 membered heterocycloalkylene. The nanoparticle linker-cleavage site may be $R^9$-substituted or unsubstituted 4 membered heterocycloalkylene. The nanoparticle linker-cleavage site may be $R^9$-substituted 4 membered heterocycloalkylene. The nanoparticle linker-cleavage site may be $R^9$-substituted or unsubstituted 3 membered heterocycloalkylene. The nanoparticle linker-cleavage site may be $R^9$-substituted 3 membered heterocycloalkylene.

The nanoparticle linker-cleavage site may be substituted or unsubstituted 5 to 20 membered arylene. The nanoparticle linker-cleavage site may be substituted or unsubstituted 5 to 15 membered arylene. The nanoparticle linker-cleavage site may be substituted or unsubstituted 5 to 10 membered arylene. The nanoparticle linker-cleavage site may be substituted or unsubstituted 5 to 8 membered arylene. The nanoparticle linker-cleavage site may be substituted or unsubstituted 5 or 6 membered arylene. The nanoparticle linker-cleavage site may be substituted or unsubstituted 6 membered arylene. The nanoparticle linker-cleavage site may be substituted 6 membered arylene. The nanoparticle linker-cleavage site may be unsubstituted 6 membered arylene. The nanoparticle linker-cleavage site may be substituted or unsubstituted 5 membered arylene. The nanoparticle linker-cleavage site may be substituted 5 membered arylene. The nanoparticle linker-cleavage site may be unsubstituted 5 membered arylene.

The nanoparticle linker-cleavage site may be $R^9$-substituted or unsubstituted 5 to 20 membered arylene. The nanoparticle linker-cleavage site may be $R^9$-substituted or unsubstituted 5 to 15 membered arylene. The nanoparticle linker-cleavage site may be $R^9$-substituted or unsubstituted 5 to 10 membered arylene. The nanoparticle linker-cleavage site may be $R^9$-substituted or unsubstituted 5 to 8 membered arylene. The nanoparticle linker-cleavage site may be $R^9$-substituted or unsubstituted 5 or 6 membered arylene. The nanoparticle linker-cleavage site may be $R^9$-substituted or unsubstituted 6 membered arylene. The nanoparticle linker-cleavage site may be $R^9$-substituted 6 membered arylene. The nanoparticle linker-cleavage site may be $R^9$-substituted or unsubstituted 5 membered arylene. The nanoparticle linker-cleavage site may be $R^9$-substituted 5 membered arylene.

The nanoparticle linker-cleavage site may be substituted or unsubstituted 5 to 20 membered heteroarylene. The nanoparticle linker-cleavage site may be substituted or unsubstituted 5 to 15 membered heteroarylene. The nanoparticle linker-cleavage site may be substituted or unsubstituted 5 to 10 membered heteroarylene. The nanoparticle linker-cleavage site may be substituted or unsubstituted 5 to 8 membered heteroarylene. The nanoparticle linker-cleavage site may be substituted or unsubstituted 5 or 6 membered heteroarylene. The nanoparticle linker-cleavage site may be substituted or unsubstituted 6 membered heteroarylene. The nanoparticle linker-cleavage site may be substituted 6 membered heteroarylene. The nanoparticle linker-cleavage site may be unsubstituted 6 membered heteroarylene. The nanoparticle linker-cleavage site may be substituted or unsubstituted 5 membered heteroarylene. The nanoparticle linker-cleavage site may be substituted 5 membered heteroarylene. The nanoparticle linker-cleavage site may be unsubstituted 5 membered heteroarylene.

The nanoparticle linker-cleavage site may be $R^9$-substituted or unsubstituted 5 to 20 membered heteroarylene. The nanoparticle linker-cleavage site may be $R^9$-substituted or unsubstituted 5 to 15 membered heteroarylene. The nanoparticle linker-cleavage site may be $R^9$-substituted or unsubstituted 5 to 10 membered heteroarylene. The nanoparticle linker-cleavage site may be $R^9$-substituted or unsubstituted 5 to 8 membered heteroarylene. The nanoparticle linker-cleavage site may be $R^9$-substituted or unsubstituted 5 or 6 membered heteroarylene. The nanoparticle linker-cleavage site may be $R^9$-substituted or unsubstituted 6 membered heteroarylene. The nanoparticle linker-cleavage site may be $R^9$-substituted 6 membered heteroarylene. The nanoparticle linker-cleavage site may be $R^9$-substituted or unsubstituted 5 membered heteroarylene. The nanoparticle linker-cleavage site may be $R^9$-substituted 5 membered heteroarylene.

$R^9$ is halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, $R^{10}$-substituted or unsubstituted alkyl (e.g. $C_1$-$C_8$ alkyl), $R^{10}$-substituted or unsubstituted heteroalkyl (e.g. 2 to 8 membered heteroalkyl), $R^{10}$-substituted or unsubstituted cycloalkyl (e.g. $C_3$-$C_8$ cycloalkyl), $R^{10}$-substituted or unsubstituted heterocycloalkyl (e.g. 3 to 6 membered heterocycloalkyl), $R^{10}$-substituted or unsubstituted aryl (e.g. 5 or 6 membered aryl), or $R^{10}$-substituted or unsubstituted heteroaryl (e.g. 5 or 6 membered heteroaryl).

$R^{10}$ is halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, unsubstituted alkyl (e.g. $C_1$-$C_8$ alkyl), heteroalkyl (e.g. 2 to 8 membered heteroalkyl), unsubstituted cycloalkyl (e.g. $C_3$-$C_8$ cycloalkyl), unsubstituted heterocycloalkyl (e.g. 3 to 6 membered heterocycloalkyl), unsubstituted aryl (e.g. 5 or 6 membered aryl), or unsubstituted heteroaryl (e.g. 5 or 6 membered heteroaryl).

The nanoparticle linker-cleavage site may be substituted or unsubstituted $C_1$-$C_5$ alkylene, 2 to 5 membered heteroalkylene, or an amino acid sequence linker. The nanoparticle linker-cleavage site may be an amino acid sequence linker. The amino acid sequence may be recognized by an enzyme. The enzyme may be an esterase that recognizes an ester (e.g. —C(O)O—). The nanoparticle linker-cleavage site may be a nucleic acid sequence linker. The nanoparticle linker-cleavage site may be an ester (e.g. —C(O)O—). The ester may be recognized by an enzyme such as an esterase.

The capping linker-cleavage site may be —O—, —S—, C(O)O—, —$SO_2$—, or —NH—. The capping linker-cleavage site may be —O—, —S—, C(O)O—, or —NH—. The capping linker-cleavage site may be substituted or unsubstituted $C_1$-$C_{20}$ alkylene. The capping linker-cleavage site-cleavage site may be substituted or unsubstituted $C_1$-$C_{15}$ alkylene. The capping linker-cleavage site may be substituted or unsubstituted $C_1$-$C_{10}$ alkylene. The capping linker-cleavage site may be substituted or unsubstituted $C_1$-$C_5$ alkylene. The capping linker-cleavage site may be substituted or unsubstituted $C_1$-$C_3$ alkylene. The capping linker-cleavage site may be substituted or unsubstituted $C_3$-$C_8$ alkylene. The capping linker-cleavage site may be substituted or unsubstituted $C_3$-$C_6$ alkylene. The capping linker-cleavage site may be substituted or unsubstituted $C_3$-$C_5$ alkylene. The capping linker-cleavage site may be substituted or unsubstituted $C_6$ alkylene. The capping linker-cleavage site may be substituted or unsubstituted $C_5$ alkylene. The capping linker-cleavage site may be substituted or unsubstituted $C_4$ alkylene. The capping linker-cleavage site may be substituted or unsubstituted $C_3$ alkylene. The capping linker-cleavage site may be substituted or unsubstituted $C_2$ alkylene.

The capping linker-cleavage site may be $R^{11}$-substituted or unsubstituted $C_1$-$C_{20}$ alkylene. The capping linker-cleavage site-cleavage site may be $R^{11}$-substituted or unsubstituted $C_1$-$C_{15}$ alkylene. The capping linker-cleavage site may be $R^{11}$-substituted or unsubstituted $C_1$-$C_{10}$ alkylene. The capping linker-cleavage site may be $R^{11}$-substituted or unsubstituted $C_1$-$C_5$ alkylene. The capping linker-cleavage site may be $R^{11}$-substituted or unsubstituted $C_1$-$C_3$ alkylene. The capping linker-cleavage site may be $R^{11}$-substituted or unsubstituted $C_3$-$C_8$ alkylene. The capping linker-cleavage site may be $R^{11}$-substituted or unsubstituted $C_3$-$C_6$ alkylene. The capping linker-cleavage site may be $R^{11}$-substituted or unsubstituted $C_3$-$C_5$ alkylene. The capping linker-cleavage site may be $R^{11}$-substituted or unsubstituted $C_6$ alkylene. The capping linker-cleavage site may be $R^{11}$-substituted or unsubstituted $C_5$ alkylene. The capping linker-cleavage site may be $R^{11}$-substituted or unsubstituted $C_4$ alkylene. The capping linker-cleavage site may be $R^{11}$-substituted or unsubstituted $C_3$ alkylene. The capping linker-cleavage site may be $R^{11}$-substituted or unsubstituted $C_2$ alkylene.

The capping linker-cleavage site may be substituted or unsubstituted 2 to 20 membered heteroalkylene. The capping linker-cleavage site may be substituted or unsubstituted 2 to 15 membered heteroalkylene. The capping linker-cleavage site may be substituted or unsubstituted 2 to 10 membered heteroalkylene. The capping linker-cleavage site may be substituted or unsubstituted 2 to 5 membered heteroalkylene. The capping linker-cleavage site may be substituted or unsubstituted 2 to 3 membered heteroalkylene. The capping linker-cleavage site may be substituted or unsubstituted 3 to 8 membered heteroalkylene. The capping linker-cleavage site may be substituted or unsubstituted 2 to 20 membered heteroalkylene. The capping linker-cleavage site may be substituted or unsubstituted 3 to 6 membered heteroalkylene. The capping linker-cleavage site may be substituted or unsubstituted 3 to 5 membered heteroalkylene. The capping linker-cleavage site may be substituted or unsubstituted 6 membered heteroalkylene. The capping linker-cleavage site may be substituted 6 membered heteroalkylene. The capping linker-cleavage site may be unsubstituted 6 membered heteroalkylene. The capping linker-cleavage site may be substituted or unsubstituted 5 membered heteroalkylene. The capping linker-cleavage site may be substituted 5 membered heteroalkylene. The capping linker-cleavage site may be unsubstituted 5 membered heteroalkylene. The capping linker-cleavage site may be substituted or unsubstituted 4 membered heteroalkylene. The capping linker-cleavage site may be substituted 4 membered heteroalkylene. The capping linker-cleavage site may be unsubstituted 4 membered heteroalkylene. The capping linker-cleavage site may be substituted or unsubstituted 3 membered heteroalkylene. The capping linker-cleavage site may be substituted 3 membered heteroalkylene. The capping linker-cleavage site may be unsubstituted 3 membered heteroalkylene. The capping linker-cleavage site may be a substituted or unsubstituted heteroalkylene including an ester moiety (e.g. —C(O)O—). The ester may be recognized by an enzyme, for example, an esterase.

The capping linker-cleavage site may be $R^{11}$-substituted or unsubstituted 2 to 20 membered heteroalkylene. The capping linker-cleavage site may be $R^{11}$-substituted or unsubstituted 2 to 15 membered heteroalkylene. The capping linker-cleavage site may be $R^{11}$-substituted or unsubstituted 2 to 10 membered heteroalkylene. The capping linker-cleavage site may be $R^{11}$-substituted or unsubstituted 2 to 5 membered heteroalkylene. The capping linker-cleavage site may be $R^{11}$-substituted or unsubstituted 2 to 3 membered heteroalkylene. The capping linker-cleavage site may be $R^{11}$-substituted or unsubstituted 3 to 8 membered heteroalkylene. The capping linker-cleavage site may be $R^{11}$-substituted or unsubstituted 2 to 20 membered heteroalkylene. The capping linker-cleavage site may be $R^{11}$-substituted or unsubstituted 3 to 6 membered heteroalkylene. The capping linker-cleavage site may be $R^{11}$-substituted or unsubstituted 3 to 5 membered heteroalkylene. The capping linker-cleavage site may be $R^{11}$-substituted or unsubstituted 6 membered heteroalkylene. The capping linker-cleavage site may be $R^{11}$-substituted 6 membered heteroalkylene. The capping linker-cleavage site may be $R^{11}$-substituted or unsubstituted 5 membered heteroalkylene. The capping linker-cleavage site may be $R^{11}$-substituted 5 membered heteroalkylene. The capping linker-cleavage site may be $R^{11}$-substituted or unsubstituted 4 membered heteroalkylene. The capping linker-cleavage site may be $R^{11}$-substituted 4 membered heteroalkylene. The capping linker-cleavage site may be $R^{11}$-substituted or unsubstituted 3 membered heteroalkylene. The capping linker-cleavage site may be $R^{11}$-substituted 3 membered heteroalkylene.

The capping linker-cleavage site may be substituted or unsubstituted 3 to 20 membered cycloalkylene. The capping linker-cleavage site may be substituted or unsubstituted 3 to 15 membered cycloalkylene. The capping linker-cleavage site may be substituted or unsubstituted 3 to 12 membered cycloalkylene. The capping linker-cleavage site may be substituted or unsubstituted 3 to 10 membered cycloalkylene. The capping linker-cleavage site may be substituted or unsubstituted 3 to 8 membered cycloalkylene. The capping linker-cleavage site may be substituted or unsubstituted 3 to 6 membered cycloalkylene. The capping linker-cleavage site may be substituted or unsubstituted 3 to 5 membered cycloalkylene. The capping linker-cleavage site may be substituted or unsubstituted 6 membered cycloalkylene. The capping linker-cleavage site may be substituted 6 membered cycloalkylene. The nanoparticle linker-cleavage site may be unsubstituted 6 membered cycloalkylene. The capping linker-cleavage site may be substituted or unsubstituted 5 membered cycloalkylene. The capping linker-cleavage site may be substituted 5 membered cycloalkylene. The capping linker-cleavage site may be unsubstituted 5 membered cycloalkylene. The capping linker-cleavage site may be substituted or unsubstituted 4 membered cycloalkylene. The capping linker-cleavage site may be substituted 4 membered cycloalkylene. The capping linker-cleavage site may be unsubstituted 4 membered cycloalkylene. The capping linker-cleavage site may be substituted or unsubstituted 3 membered cycloalkylene. The capping linker-cleavage site may be substituted 3 membered cycloalkylene. The capping linker-cleavage site may be unsubstituted 3 membered cycloalkylene.

The capping linker-cleavage site may be $R^{11}$-substituted or unsubstituted 3 to 20 membered cycloalkylene. The capping linker-cleavage site may be $R^{11}$-substituted or unsubstituted 3 to 15 membered cycloalkylene. The capping linker-cleavage site may be $R^{11}$-substituted or unsubstituted 3 to 12 membered cycloalkylene. The capping linker-cleavage site may be $R^{11}$-substituted or unsubstituted 3 to 10 membered cycloalkylene. The capping linker-cleavage site may be $R^{11}$-substituted or unsubstituted 3 to 8 membered cycloalkylene. The capping linker-cleavage site may be $R^{11}$-substituted or unsubstituted 3 to 6 membered cycloalkylene. The capping linker-cleavage site may be $R^{11}$-substituted or unsubstituted 3 to 5 membered cycloalkylene. The capping linker-cleavage site may be $R^{11}$-substituted or unsubstituted 6 membered cycloalkylene. The capping linker-cleavage site may be $R^{11}$-substituted or unsubstituted 6 membered cycloalkylene. The capping linker-cleavage site may be $R^{11}$-substituted 6 membered cycloalkylene. The capping linker-cleavage site may be $R^{11}$-substituted or unsubstituted 5 membered cycloalkylene. The capping linker-cleavage site may be $R^{11}$-substituted 5 membered cycloalkylene. The capping linker-cleavage site may be substituted 4 membered cycloalkylene. The capping linker-cleavage site may be $R^{11}$-substituted or unsubstituted 3 membered cycloalkylene. The capping linker-cleavage site may be $R^{11}$-substituted 3 membered cycloalkylene.

The capping linker-cleavage site may be substituted or unsubstituted 3 to 20 membered heterocycloalkylene. The capping linker-cleavage site may be substituted or unsubstituted 3 to 15 membered heterocycloalkylene. The capping linker-cleavage site may be substituted or unsubstituted 3 to 12 membered heterocycloalkylene. The capping linker-cleavage site may be substituted or unsubstituted 3 to 10 membered heterocycloalkylene. The capping linker-cleavage site may be substituted or unsubstituted 3 to 8 membered heterocycloalkylene. The capping linker-cleavage site may be substituted or unsubstituted 3 to 6 membered heterocycloalkylene. The capping linker-cleavage site may be substituted or unsubstituted 3 to 5 membered heterocycloalkylene. The capping linker-cleavage site may be substituted or unsubstituted 6 membered heterocycloalkylene. The capping linker-cleavage site may be substituted 6 membered heterocycloalkylene. The capping linker-cleavage site may be unsubstituted 6 membered heterocycloalkylene. The capping linker-cleavage site may be substituted or unsubstituted 5 membered heterocycloalkylene. The capping linker-cleavage site may be substituted 5 membered heterocycloalkylene. The capping linker-cleavage site may be unsubstituted 5 membered heterocycloalkylene. The capping linker-cleavage site may be substituted or unsubstituted 4 membered heterocycloalkylene. The capping linker-cleavage site may be substituted 4 membered heterocycloalkylene. The capping linker-cleavage site may be unsubstituted 4 membered heterocycloalkylene. The capping linker-cleavage site may be substituted or unsubstituted 3 membered heterocycloalkylene. The capping linker-cleavage site may be substituted 3 membered heterocycloalkylene. The capping linker-cleavage site may be unsubstituted 3 membered heterocycloalkylene.

The capping linker-cleavage site may be $R^{11}$-substituted or unsubstituted 3 to 20 membered heterocycloalkylene. The capping linker-cleavage site may be $R^{11}$-substituted or unsubstituted 3 to 15 membered heterocycloalkylene. The capping linker-cleavage site may be $R^{11}$-substituted or unsubstituted 3 to 12 membered heterocycloalkylene. The capping linker-cleavage site may be $R^{11}$-substituted or unsubstituted 3 to 10 membered heterocycloalkylene. The capping linker-cleavage site may be $R^{11}$-substituted or unsubstituted 3 to 8 membered heterocycloalkylene. The capping linker-cleavage site may be $R^{11}$-substituted or unsubstituted 3 to 6 membered heterocycloalkylene. The capping linker-cleavage site may be $R^{11}$-substituted or unsubstituted 3 to 5 membered heterocycloalkylene. The capping linker-cleavage site may be $R^{11}$-substituted or unsubstituted 6 membered heterocycloalkylene. The capping linker-cleavage site may be $R^{11}$-substituted 6 membered heterocycloalkylene. The capping linker-cleavage site may be $R^{11}$-substituted 5 membered heterocycloalkylene. capping linker-cleavage site may be $R^{11}$-substituted or unsubstituted 4 membered heterocycloalkylene. The capping linker-cleavage site may be $R^{11}$-substituted 4 membered heterocycloalkylene. The capping linker-cleavage site may be $R^{11}$-substituted or unsubstituted 3 membered heterocycloalkylene. The capping linker-cleavage site may be $R^{11}$-substituted 3 membered heterocycloalkylene.

The capping linker-cleavage site may be substituted or unsubstituted 5 to 20 membered arylene. The capping linker-cleavage site may be substituted or unsubstituted 5 to 15 membered arylene. The capping linker-cleavage site may be substituted or unsubstituted 5 to 10 membered arylene. The capping linker-cleavage site may be substituted or unsubstituted 5 to 8 membered arylene. The capping linker-cleavage site may be substituted or unsubstituted 5 or 6 membered arylene. The capping linker-cleavage site may be substituted or unsubstituted 6 membered arylene. The capping linker-cleavage site may be substituted 6 membered arylene. The capping linker-cleavage site may be unsubstituted 6 membered arylene. The capping linker-cleavage site may be substituted or unsubstituted 5 membered arylene. The capping linker-cleavage site may be substituted 5 membered arylene. The capping linker-cleavage site may be unsubstituted 5 membered arylene.

The capping linker-cleavage site may be $R^{11}$-substituted or unsubstituted 5 to 20 membered arylene. The capping linker-cleavage site may be $R^{11}$-substituted or unsubstituted 5 to 15 membered arylene. The capping linker-cleavage site may be $R^{11}$-substituted or unsubstituted 5 to 10 membered arylene. The capping linker-cleavage site may be $R^{11}$-substituted or unsubstituted 5 to 8 membered arylene. The capping linker-cleavage site may be $R^{11}$-substituted or unsubstituted 5 or 6 membered arylene. The capping linker-cleavage site may be $R^{11}$-substituted or unsubstituted 6 membered arylene. The capping linker-cleavage site may be $R^{11}$-substituted 6 membered arylene. The capping linker-cleavage site may be $R^{11}$-substituted or unsubstituted 5 membered arylene. The capping linker-cleavage site may be $R^{11}$-substituted 5 membered arylene.

The capping linker-cleavage site may be substituted or unsubstituted 5 to 20 membered heteroarylene. The capping linker-cleavage site may be substituted or unsubstituted 5 to 15 membered heteroarylene. The capping linker-cleavage site may be substituted or unsubstituted 5 to 10 membered heteroarylene. The capping linker-cleavage site may be substituted or unsubstituted 5 to 8 membered heteroarylene. The capping linker-cleavage site may be substituted or unsubstituted 5 or 6 membered heteroarylene. The capping linker-cleavage site may be substituted or unsubstituted 6 membered heteroarylene. The capping linker-cleavage site may be substituted 6 membered heteroarylene. The capping linker-cleavage site may be unsubstituted 6 membered heteroarylene. The capping linker-cleavage site may be substituted or unsubstituted 5 membered heteroarylene. The capping linker-cleavage site may be substituted 5 membered heteroarylene. The capping linker-cleavage site may be unsubstituted 5 membered heteroarylene.

The capping linker-cleavage site may be $R^{11}$-substituted or unsubstituted 5 to 20 membered heteroarylene. The capping linker-cleavage site may be $R^{11}$-substituted or unsubstituted 5 to 15 membered heteroarylene. The capping linker-cleavage site may be $R^{11}$-substituted or unsubstituted 5 to 10 membered heteroarylene. The capping linker-cleavage site may be $R^{11}$-substituted or unsubstituted 5 to 8 membered heteroarylene. The capping linker-cleavage site may be $R^{11}$-substituted or unsubstituted 5 or 6 membered heteroarylene. The capping linker-cleavage site may be $R^{11}$-substituted or unsubstituted 6 membered heteroarylene. The capping linker-cleavage site may be $R^{11}$-substituted 6 membered heteroarylene. The capping linker-cleavage site may be $R^{11}$-substituted 5 membered heteroarylene.

$R^{11}$ is halogen, $-N_3$, $-CF_3$, $-CCl_3$, $-CBr_3$, $-CI_3$, $-CN$, $-CHO$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC(O)NHNH_2$, $R^{12}$-substituted or unsubstituted alkyl (e.g. $C_1$-$C_8$ alkyl), $R^{12}$-substituted or unsubstituted heteroalkyl (e.g. 2 to 8 membered heteroalkyl), $R^{12}$-substituted or unsubstituted cycloalkyl (e.g. $C_3$-$C_8$ cycloalkyl), $R^{12}$-substituted or unsubstituted heterocycloalkyl (e.g. 3 to 6 membered heterocycloalkyl), $R^{12}$-substituted or unsubstituted aryl (e.g. 5 or 6 membered aryl), or $R^{12}$-substituted or unsubstituted heteroaryl (e.g. 5 or 6 membered heteroaryl).

$R^{11}$ is halogen, $-N_3$, $-CF_3$, $-CCl_3$, $-CBr_3$, $-CI_3$, $-CN$, $-CHO$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC(O)NHNH_2$, unsubstituted alkyl (e.g. $C_1$-$C_8$ alkyl), heteroalkyl (e.g. 2 to 8 membered heteroalkyl), unsubstituted cycloalkyl (e.g. $C_3$-$C_8$ cycloalkyl), unsubstituted heterocycloalkyl (e.g. 3 to 6 membered heterocycloalkyl), unsubstituted aryl (e.g. 5 or 6 membered aryl), or unsubstituted heteroaryl (e.g. 5 or 6 membered heteroaryl).

The capping linker-cleavage site may be substituted or unsubstituted $C_1$-$C_5$ alkylene, 2 to 5 membered heteroalkylene, or an amino acid sequence linker. The capping linker-cleavage site may be an amino acid sequence linker. The amino acid sequence may be recognized by an enzyme. The enzyme may be an esterase that recognizes an ester (e.g. $-C(O)O-$). The capping linker-cleavage site may be a nucleic acid sequence linker. The capping linker-cleavage site may be an ester (e.g. $-C(O)O-$). The ester may be recognized by an enzyme such as an esterase.

The capping substituent may be halogen, $-N_3$, $-CF_3$, $-CCl_3$, $-CBr_3$, $-CI_3$, $-CN$, $-CHO$, $-OH$, $-NH_2$, $-COOH$, $-CONH_2$, $-NO_2$, $-SH$, $-SO_2$, $-SO_2Cl$, $-SO_3H$, $-SO_4H$, $-SO_2NH_2$, $-NHNH_2$, $-ONH_2$, $-NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

The capping substituent may be $-N_3$, $-CF_3$, $-CCl_3$, $-CBr_3$, $-CI_3$, $-CN$, $-CHO$, $-OH$, $-NH_2$, $-COOH$, $-CONH_2$, $-NO_2$, $-SH$, $-SO_2$, $-SO_2Cl$, $-SO_3H$, $-SO_4H$, $-SO_2NH_2$, $-NHNH_2$, $-ONH_2$, $-NHC(O)NHNH_2$. The capping substituent may be substituted or unsubstituted $C_1$-$C_{20}$ alkyl. The capping substituent site may be substituted or unsubstituted $C_1$-$C_{15}$ alkyl. The capping substituent may be substituted or unsubstituted $C_1$-$C_{10}$ alkyl. The capping substituent may be substituted or unsubstituted $C_1$-$C_5$ alkyl. The capping substituent may be substituted or unsubstituted $C_1$-$C_3$ alkyl. The capping substituent may be substituted or unsubstituted $C_3$-$C_8$ alkyl. The capping substituent may be substituted or unsubstituted $C_3$-$C_6$ alkyl. The capping substituent may be substituted or unsubstituted $C_3$-$C_5$ alkyl. The capping substituent may be substituted or unsubstituted $C_6$ alkyl. The capping substituent may be substituted or unsubstituted $C_5$ alkyl. The capping substituent may be substituted or unsubstituted $C_4$ alkyl. The capping substituent may be substituted or unsubstituted $C_3$ alkyl. The capping substituent may be substituted or unsubstituted $C_2$ alkyl.

The capping substituent may be $R^{12}$-substituted or unsubstituted $C_1$-$C_{20}$ alkyl. The capping substituent site may be $R^{12}$-substituted or unsubstituted $C_1$-$C_{15}$ alkyl. The capping substituent may be $R^{12}$-substituted or unsubstituted $C_1$-$C_{10}$ alkyl. The capping substituent may be $R^{12}$-substituted or unsubstituted $C_1$-$C_5$ alkyl. The capping substituent may be $R^{12}$-substituted or unsubstituted $C_1$-$C_3$ alkyl. The capping substituent may be $R^{12}$-substituted or unsubstituted $C_3$-$C_8$ alkyl. The capping substituent may be $R^{12}$-substituted or unsubstituted $C_3$-$C_6$ alkyl. The capping substituent may be $R^{12}$-substituted or unsubstituted $C_3$-$C_5$ alkyl. The capping substituent may be $R^{12}$-substituted or unsubstituted $C_6$ alkyl. The capping substituent may be $R^{12}$-substituted or unsubstituted $C_5$ alkyl. The capping substituent may be $R^{12}$-substituted or unsubstituted $C_4$ alkyl. The capping substituent may be $R^{12}$-substituted or unsubstituted $C_3$ alkyl. The capping substituent may be $R^{12}$-substituted or unsubstituted $C_2$ alkyl.

The capping substituent may be substituted or unsubstituted 2 to 20 membered heteroalkyl. The capping substituent may be substituted or unsubstituted 2 to 15 membered heteroalkyl. The capping substituent may be substituted or unsubstituted 2 to 10 membered heteroalkyl. The capping substituent may be substituted or unsubstituted 2 to 5 membered heteroalkyl. The capping substituent may be substituted or unsubstituted 2 to 3 membered heteroalkyl. The capping substituent may be substituted or unsubstituted 3 to 8 membered heteroalkyl. The capping substituent may be substituted or unsubstituted 2 to 20 membered heteroalkyl. The capping substituent may be substituted or unsubstituted 3 to 6 membered heteroalkyl. The capping substituent may be substituted or unsubstituted 3 to 5 membered heteroalkyl. The capping substituent may be substituted or unsubstituted 6 membered heteroalkyl. The capping substituent may be substituted 6 membered heteroalkyl. The capping substituent may be unsubstituted 6 membered heteroalkyl. The capping substituent may be substituted or unsubstituted 5 membered heteroalkyl. The capping substituent may be substituted 5 membered heteroalkyl. The capping substituent may be unsubstituted 5 membered heteroalkyl. The capping substituent may be substituted or unsubstituted 4 membered heteroalkyl. The capping substituent may be substituted 4 membered heteroalkyl. The capping substituent may be unsubstituted 4 membered heteroalkyl. The capping substituent may be substituted or unsubstituted 3 membered heteroalkyl. The capping substituent may be substituted 3 membered heteroalkyl. The capping substituent may be unsubstituted 3 membered heteroalkyl.

The capping substituent may be $R^{12}$-substituted or unsubstituted 2 to 20 membered heteroalkyl. The capping substituent may be $R^{12}$-substituted or unsubstituted 2 to 15 membered heteroalkyl. The capping substituent may be $R^{12}$-substituted or unsubstituted 2 to 10 membered heteroalkyl. The capping substituent may be $R^{12}$-substituted or unsubstituted 2 to 5 membered heteroalkyl. The capping substituent may be $R^{12}$-substituted or unsubstituted 2 to 3 membered heteroalkyl. The capping substituent may be $R^{12}$-substituted or unsubstituted 3 to 8 membered heteroalkyl. The capping substituent may be $R^{12}$-substituted or unsubstituted 2 to 20 membered heteroalkyl. The capping substituent may be $R^{12}$-substituted or unsubstituted 3 to 6 membered heteroalkyl. The capping substituent may be $R^{12}$-substituted or unsubstituted 3 to 5 membered heteroalkyl. The capping substituent may be $R^{12}$-substituted or unsubstituted 6 membered heteroalkyl. The capping substituent may be $R^{12}$-substituted 6 membered heteroalkyl. The capping substituent may be $R^{12}$-substituted or unsubstituted 5 membered heteroalkyl. The capping substituent may be $R^{12}$-substituted 5 membered heteroalkyl. The capping substituent may be $R^{12}$-substituted or unsubstituted 4 membered heteroalkyl. The capping substituent may be $R^{12}$-substituted 4 membered heteroalkyl. The capping substituent may be $R^{12}$-substituted or unsubstituted 3 membered heteroalkyl. The capping substituent may be $R^{12}$-substituted 3 membered heteroalkyl.

The capping substituent may be substituted or unsubstituted 3 to 20 membered cycloalkyl. The capping substituent may be substituted or unsubstituted 3 to 15 membered cycloalkyl. The capping substituent may be substituted or unsubstituted 3 to 12 membered cycloalkyl. The capping substituent may be substituted or unsubstituted 3 to 10 membered cycloalkyl. The capping substituent may be substituted or unsubstituted 3 to 8 membered cycloalkyl. The capping substituent may be substituted or unsubstituted 3 to 6 membered cycloalkyl. The capping substituent may be substituted or unsubstituted 3 to 5 membered cycloalkyl. The capping substituent may be substituted or unsubstituted 6 membered cycloalkyl. The capping substituent may be substituted 6 membered cycloalkyl. The capping substituent may be unsubstituted 6 membered cycloalkyl. The capping substituent may be substituted or unsubstituted 5 membered cycloalkyl. The capping substituent may be substituted 5 membered cycloalkyl. The capping substituent may be unsubstituted 5 membered cycloalkyl. The capping substituent may be substituted or unsubstituted 4 membered cycloalkyl. The capping substituent may be substituted 4 membered cycloalkyl. The capping substituent may be unsubstituted 4 membered cycloalkyl. The capping substituent may be substituted or unsubstituted 3 membered cycloalkyl. The capping substituent may be substituted 3 membered cycloalkyl. The capping substituent may be unsubstituted 3 membered cycloalkyl.

The capping substituent may be $R^{12}$-substituted or unsubstituted 3 to 20 membered cycloalkyl. The capping substituent may be $R^{12}$-substituted or unsubstituted 3 to 15 membered cycloalkyl. The capping substituent may be $R^{12}$-substituted or unsubstituted 3 to 12 membered cycloalkyl. The capping substituent may be $R^{12}$-substituted or unsubstituted 3 to 10 membered cycloalkyl. The capping substituent may be $R^{12}$-substituted or unsubstituted 3 to 8 membered cycloalkyl. The capping substituent may be $R^{12}$-substituted or unsubstituted 3 to 6 membered cycloalkyl. The capping substituent may be $R^{12}$-substituted or unsubstituted 3 to 5 membered cycloalkyl. The capping substituent may be $R^{12}$-substituted or unsubstituted 6 membered cycloalkyl. The capping substituent may be $R^{12}$-substituted 6 membered cycloalkyl. The capping substituent may be $R^{12}$-substituted or unsubstituted 5 membered cycloalkyl. The capping substituent may be $R^{12}$-substituted 5 membered cycloalkyl. The capping substituent may be $R^{12}$-substituted or unsubstituted 4 membered cycloalkyl. The capping substituent may be $R^{12}$-substituted 4 membered cycloalkyl. The capping substituent may be $R^{12}$-substituted or unsubstituted 3 membered cycloalkyl. The capping substituent may be $R^{12}$-substituted 3 membered cycloalkyl.

The capping substituent may be substituted or unsubstituted 3 to 20 membered heterocycloalkyl. The capping substituent may be substituted or unsubstituted 3 to 15 membered heterocycloalkyl. The capping substituent may be substituted or unsubstituted 3 to 12 membered heterocycloalkyl. The capping substituent may be substituted or unsubstituted 3 to 10 membered heterocycloalkyl. The capping substituent may be substituted or unsubstituted 3 to 8 membered heterocycloalkyl. The capping substituent may be substituted or unsubstituted 3 to 6 membered heterocycloalkyl. The capping substituent may be substituted or unsubstituted 3 to 5 membered heterocycloalkyl. The capping substituent may be substituted or unsubstituted 6 membered heterocycloalkyl. The capping substituent may be substituted 6 membered heterocycloalkyl. The capping substituent may be unsubstituted 6 membered heterocycloalkyl. The capping substituent may be substituted or unsubstituted 5 membered heterocycloalkyl. The capping substituent may be substituted 5 membered heterocycloalkyl. The capping substituent may be unsubstituted 5 membered heterocycloalkyl. The capping substituent may be substituted or unsubstituted 4 membered heterocycloalkyl. The capping substituent may be substituted 4 membered heterocycloalkyl. The capping substituent may be unsubstituted 4 membered heterocycloalkyl. The capping substituent may be substituted or unsubstituted 3 membered heterocycloalkyl. The capping substituent may be substituted 3 membered heterocycloalkyl. The capping substituent may be unsubstituted 3 membered heterocycloalkyl.

The capping substituent may be $R^{12}$-substituted or unsubstituted 3 to 20 membered heterocycloalkyl. The capping substituent may be $R^{12}$-substituted or unsubstituted 3 to 15 membered heterocycloalkyl. The capping substituent may be $R^{12}$-substituted or unsubstituted 3 to 12 membered heterocycloalkyl. The capping substituent may be $R^{12}$-substituted or unsubstituted 3 to 10 membered heterocycloalkyl. The capping substituent may be $R^{12}$-substituted or unsubstituted 3 to 8 membered heterocycloalkyl. The capping substituent may be $R^{12}$-substituted or unsubstituted 3 to 6 membered heterocycloalkyl. The capping substituent may be $R^{12}$-substituted or unsubstituted 3 to 5 membered heterocycloalkyl. The capping substituent may be $R^{12}$-substituted or unsubstituted 6 membered heterocycloalkyl. The capping substituent may be $R^{12}$-substituted 6 membered heterocycloalkyl. The capping substituent may be $R^{12}$-substituted or unsubstituted 5 membered heterocycloalkyl. The capping substituent may be $R^{12}$-substituted 5 membered heterocycloalkyl. The capping substituent may be $R^{12}$-substituted or unsubstituted 4 membered heterocycloalkyl. The capping substituent may be $R^{12}$-substituted 4 membered heterocycloalkyl. The capping substituent may be $R^{12}$-substituted or unsubstituted 3 membered heterocycloalkyl. The capping substituent may be $R^{12}$-substituted 3 membered heterocycloalkyl.

The capping substituent may be substituted or unsubstituted 5 to 20 membered aryl. The capping substituent may be substituted or unsubstituted 5 to 15 membered aryl. The capping substituent may be substituted or unsubstituted 5 to 10 membered aryl. The capping substituent may be substituted or unsubstituted 5 to 8 membered aryl. The capping substituent may be substituted or unsubstituted 5 or 6 membered aryl. The capping substituent may be substituted or unsubstituted 6 membered aryl. The capping substituent may be substituted 6 membered aryl. The capping substituent may be unsubstituted 6 membered aryl. The capping substituent may be substituted or unsubstituted 5 membered aryl. The capping substituent may be substituted 5 membered aryl. The capping substituent may be unsubstituted 5 membered aryl.

The capping substituent may be $R^{12}$-substituted or unsubstituted 5 to 20 membered aryl. The capping substituent may be $R^{12}$-substituted or unsubstituted 5 to 15 membered aryl. The capping substituent may be $R^{12}$-substituted or unsubstituted 5 to 10 membered aryl. The capping substituent may be $R^{12}$-substituted or unsubstituted 5 to 8 membered aryl. The capping substituent may be $R^{12}$-substituted or unsubstituted 5 or 6 membered aryl. The capping substituent may be $R^{12}$-substituted or unsubstituted 6 membered aryl. The capping substituent may be $R^{12}$-substituted 6 membered aryl. The capping substituent may be $R^{12}$-substituted or unsubstituted 5 membered aryl. The capping substituent may be $R^{12}$-substituted 5 membered aryl.

The capping substituent may be substituted or unsubstituted 5 to 20 membered heteroaryl. The capping substituent may be substituted or unsubstituted 5 to 15 membered heteroaryl. The capping substituent may be substituted or unsubstituted 5 to 10 membered heteroaryl. The capping substituent may be substituted or unsubstituted 5 to 8 membered heteroaryl. The capping substituent may be substituted or unsubstituted 5 or 6 membered heteroaryl. The capping substituent may be substituted or unsubstituted 6 membered heteroaryl. The capping substituent may be substituted 6 membered heteroaryl. The capping substituent may be unsubstituted 6 membered heteroaryl. The capping substituent may be substituted or unsubstituted 5 membered heteroaryl. The capping substituent may be substituted 5 membered heteroaryl. The capping substituent may be unsubstituted 5 membered heteroaryl.

The capping substituent may be $R^{12}$-substituted or unsubstituted 5 to 20 membered heteroaryl. The capping substituent may be $R^{12}$-substituted or unsubstituted 5 to 15 membered heteroaryl. The capping substituent may be $R^{12}$-substituted or unsubstituted 5 to 10 membered heteroaryl. The capping substituent may be $R^{12}$-substituted or unsubstituted 5 to 8 membered heteroaryl. The capping substituent may be $R^{12}$-substituted or unsubstituted 5 or 6 membered heteroaryl. The capping substituent may be $R^{12}$-substituted or unsubstituted 6 membered heteroaryl. The capping substituent may be $R^{12}$-substituted 6 membered heteroaryl. The capping substituent may be $R^{12}$-substituted or unsubstituted 5 membered heteroaryl. The capping substituent may be $R^{12}$-substituted 5 membered heteroaryl.

The capping substituent may be substituted or unsubstituted $C_1$-$C_5$ alkyl, 2 to 5 membered heteroalkyl, or 3 to 6 membered cycloalkyl. The capping substituent may be substituted or unsubstituted maleimide as described herein, including embodiments thereof. The capping substituent may be substituted or unsubstituted vinyl sulfone as described herein, including embodiments thereof.

$R^{12}$ is halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, $R^{13}$-substituted or unsubstituted alkyl (e.g. $C_1$-$C_8$ alkyl), $R^{13}$-substituted or unsubstituted heteroalkyl (e.g. 2 to 8 membered heteroalkyl), $R^{13}$-substituted or unsubstituted cycloalkyl (e.g. $C_3$-$C_8$ cycloalkyl), $R^{13}$-substituted or unsubstituted heterocycloalkyl (e.g. 3 to 6 membered heterocycloalkyl), $R^{13}$-substituted or unsubstituted aryl (e.g. 5 or 6 membered aryl), or $R^{13}$-substituted or unsubstituted heteroaryl (e.g. 5 or 6 membered heteroaryl).

$R^{13}$ is halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, $R^{14}$-substituted or unsubstituted alkyl (e.g. $C_1$-$C_8$ alkyl), $R^{14}$-substituted or unsubstituted heteroalkyl (e.g. 2 to 8 membered heteroalkyl), $R^{14}$-substituted or unsubstituted cycloalkyl (e.g. $C_3$-$C_8$ cycloalkyl), $R^{14}$-substituted or unsubstituted heterocycloalkyl (e.g. 3 to 6 membered heterocycloalkyl), $R^{14}$- substituted or unsubstituted aryl (e.g. 5 or 6 membered aryl), or $R^{14}$-substituted or unsubstituted heteroaryl (e.g. 5 or 6 membered heteroaryl).

$R^{14}$ is halogen, $-N_3$, $-CF_3$, $-CCl_3$, $-CBr_3$, $-CI_3$, $-CN$, $-CHO$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC(O)NHNH_2$, unsubstituted alkyl (e.g. $C_1$-$C_8$ alkyl), heteroalkyl (e.g. 2 to 8 membered heteroalkyl), unsubstituted cycloalkyl (e.g. $C_3$-$C_8$ cycloalkyl), unsubstituted heterocycloalkyl (e.g. 3 to 6 membered heterocycloalkyl), unsubstituted aryl (e.g. 5 or 6 membered aryl), or unsubstituted heteroaryl (e.g. 5 or 6 membered heteroaryl).

The capping substituent may be substituted with a capping functional group. The capping functional group includes a hydrophobic moiety, hydrophilic moiety, biological moiety, therapeutic moiety, targeting moiety, water soluble polymer moiety, or detectable moiety. The capping substituent may be substituted with two or more capping functional groups. The capping substituent may be substituted with a therapeutic moiety and a targeting moiety. The capping substituent may be substituted with a therapeutic moiety and a water soluble moiety. The capping substituent may be substituted with a detectable moiety and a targeting moiety. The capping substituent may be substituted with a detectable moiety and a water soluble moiety. The capping substituent may be substituted with a therapeutic moiety and a detectable moiety. The hydrophobic moiety may be a moiety that adjusts solubility of the nanoparticle aggregate in nonpolar organic solvents. The hydrophobic moiety may be substituted or unsubstituted alkyl, substituted or unsubstituted heteroalkyl, substituted or unsubstituted cycloalkyl, substituted or unsubstituted heterocycloalkyl, substituted or unsubstituted aryl (e.g. substituted or unsubstituted phenyl), or substituted or unsubstituted heteroaryl. The hydrophilic moiety may be a group that adjusts solubility of the nanoparticle aggregate in polar solvents/solutions. The biological moiety may be a group as described herein, including embodiments thereof. In embodiments, the biological moiety is a peptidyl moiety. The peptidyl moiety may be an antibody moiety. In embodiments, the biological moiety is a nucleic acid moiety.

The water soluble polymer moiety is a group that increases the water solubility of the nanoparticle aggregate. The water soluble polymer moiety may be a linear or branched polyethylene glycol (PEG) moiety. The PEG moiety may have an average molecular weight of about 200 (i.e. $PEG_{200}$) to about 40,000 (i.e. $PEG_{40,000}$). The PEG moiety may be $PEG_{200}$. The PEG moiety may be $PEG_{500}$. The PEG moiety may be $PEG_{1000}$. The PEG moiety may be $PEG_{2000}$. The PEG moiety may be $PEG_{3000}$. The PEG moiety may be $PEG_{1000}$. The PEG moiety may be $PEG_{5000}$. The PEG moiety may be $PEG_{6000}$. The PEG moiety may be $PEG_{7000}$. The PEG moiety may be $PEG_{8000}$. The PEG moiety may be $PEG_{9000}$. The PEG moiety may be $PEG_{10,000}$. The PEG moiety may be $PEG_{20,000}$. The PEG moiety may be $PEG_{30,000}$. The PEG moiety may be $PEG_{40,000}$.

The detectable moiety is a moiety detectable by methods known in the art. The detectable moiety may be a moiety detectable by imaging fluorescence (e.g. fluorophores). The detectable moiety may be a moiety detectable by spectroscopic techniques such as, for example, Raman Spectroscopy (e.g. a Raman tag such as a diyne or alkyne). The detectable moiety may be a moiety detectable by using non-ionizing radio frequency (e.g. (nuclear magnetic resonance (NMR), magnetic resonance imaging (MRI), nuclear magnetic resonance imaging (NMRI) or magnetic resonance tomography (MRT)). The detectable moiety may be a moiety detectable by using non-ionizing radiation (e.g. computerized tomography (e.g. CT)). The detectable moiety may be a moiety detectable by electromagnetic radiation (e.g. X-ray). The detectable moiety may be a moiety detectable by measuring radioactivity (e.g. radionuclides emitting alpha, gamma, beta radiation, or positron emission tomography (PET)). Exemplary radionuclides considered medically useful include radionuclides of Y, Ln, Cu, Lu, Tc, Re, Co, Fe, such as, $^{90}$Y, $^{111}$Ln, $^{67}$Cu, $^{77}$Lu, and $^{99}$Tc. The radionuclide may be $^{111}$Ln, $^{113}$mLn, $^{67}$Ga, $^{68}$Ga, $^{99}$mTc, $^{51}$Cr, $^{197}$Hg, $^{203}$Hg, $^{169}$Yb, $^{85}$Sr, and $^{87}$Sr.

The detectable moiety may be a radioisotope. The radioisotope may be a radioisotope of gallium (for example, $^{67}$Ga or $^{68}$Ga), iodine (for example, $^{123}$I, $^{126}$I, $^{131}$I, $^{132}$I, or $^{133}$I), indium (for example, $^{111}$In or $^{113}$In), thallium (for example, $^{201}$Tl or $^{203}$Tl), or radioisotypes such as $^{3}$H, $^{11}$C, $^{14}$C, $^{13}$N, $^{18}$F, $^{22}$Na, $^{24}$Na, $^{31}$Si, $^{32}$P, $^{35}$S, $^{36}$Cl, $^{38}$Cl, $^{42}$K, $^{45}$Ca, $^{51}$Cr, $^{52}$Mn, $^{54}$Mn, $^{55}$Fe, $^{59}$Fe, $\alpha$Co, $^{63}$Zn, $^{65}$Zn, $^{68}$Zn, $^{82}$Br, $^{85}$Kr, $^{89}$Sr, $^{99}$Tc, $^{99}$mTc, $^{99}$mRe, $^{101}$Re, $^{105}$Re, $^{121}$mTe, $^{122}$mTe, $^{125}$mRe, $^{137}$Cs, $^{165}$Tm, $^{167}$Tm, $^{168}$Tm, $^{81}$mKr, $^{33}$Xe, $^{90}$Y, $^{213}$Bi, $^{77}$Br, $^{18}$F, $^{95}$Ru, $^{97}$Ru, $^{103}$Ru, $^{105}$Ru, $^{107}$Hg, $^{203}$Hg, $^{182}$Ta, $^{192}$Ir, or $^{198}$Au. The detectable moiety may be a moiety detectable by ultrasonic methods (e.g. ultrasonic imaging such as sonography). The detectable moiety may be a moiety detectable by imaging bioluminescence (e.g. bioluminescence imaging). Bioluminescent detectable moieties may be detectable in the presence or absence of a substrate. The detectable moiety may be a moiety detectable by its mass (i.e. a moiety exhibiting a distinct mass spectrum using mass spectroscopy types known in the art such as, for example, inductively coupled plasma mass spectroscopy (ICP-MS), fast atom bombardment (FAB), matrix-assisted laser desorption/ionization (MALDI), electrospray ionization (ESI) or elemental analysis as described herein.

The detectable moiety is a Magnetic Resonance Imaging (MRI contrast) agent such as, for example, magnetic agents such a Gadolinium and iron-oxide chelates. In embodiments, the MRI agent is ferric chloride, ferric ammonium citrate, gadolinium-DTPA (Gd-DTPA), Gd-DOTA, Gd-EDTA, $GdCl_3$, Gadodiamide, Gadoteridol, gadopentetate dimeglumine, Cr(III) agents, Mn(III)TPPS4 (manganese(III) tetra-[4-sulfanatophenyl]porphyrin), Fe(III)TPPS4, manganese dichloride, Fe-EHPG (iron(III) ethylenebis-(2-hydroxyphenylglycine)), $^{99}$mTc-iminodiacetate (Tc-IDA), chromium diethyl HIDA meglumine (Cr-HIDA), Gd-BOPTA (gadobenate dimeglumine), manganese(II)-dipyridoxal diphosphate (Mn-DPDP), gadolinium oxide, superparamagnetic iron oxides (SPIO, also "small particle iron oxides"), ultrasmall supermagnetic particle iron oxides (USPIO, and "ultrasmall particle iron oxides").

The therapeutic moiety may be an anti-cancer agent, a chemotherapeutic agent, or a radiotherapy agent. The therapeutic moiety may be an anti-cancer agent as described herein. The therapeutic moiety may be covalently bound to the capping substituent. The therapeutic moiety may be an solid tumor anti-cancer agent (e.g. an anti-cancer agent which treats solid tumors in cancer).

The targeting moiety is a moiety capable of binding to, or otherwise exhibiting an affinity for, a particular type of tissue or component thereof. The targeting moiety may be a DNA, RNA, protein, or antibody that targets the nanoparticle aggregate to a specific location. In embodiments, the targeting moiety is an antibody. The targeting moiety may target specific tumors or cancer cells. The targeting moiety may be specific for (i.e. target) a solid tumor.

The central polyvalent moiety may be —C—, —Si—, —N—, —P—, —O—, —S—, —Se—, or a metal. The central polyvalent moiety may be CL$_n$, where L represents a linker, for example, a nanoparticle linker or capping linker and the symbol n is at least 2. The symbol n may be at least 3. The symbol n may be 3. The symbol n may be at least 4. The symbol n may be 4.

III. Methods of Preparing Nanoparticle Aggregates

In another aspect a method for preparing a nanoparticle aggregate is provided. The method includes contacting a plurality of nanoparticle cores with a first plurality of reactive polyvalent linkers thereby forming a plurality of polyvalent linkers binding the nanoparticle cores together, wherein a first portion of the plurality of nanoparticle cores are bound to together to form a plurality of interior nanoparticle cores and a second portion of the plurality of nanoparticle cores are bound together to form a plurality of exterior nanoparticle cores enclosing the plurality of interior nanoparticle cores, wherein the plurality of exterior nanoparticle cores are bound to a portion of the plurality of interior nanoparticle cores. The method further includes allowing a portion of the plurality of reactive polyvalent linkers to react with a portion of the exterior nanoparticle cores thereby forming a plurality of reactive exterior polyvalent linkers bound to the portion of the plurality of exterior nanoparticle cores. The method further includes contacting the nanoparticle aggregate with a reactive capping substituent and allowing the reactive capping substituent to react with the plurality of reactive exterior polyvalent linkers thereby forming the nanoparticle aggregate. The method may include a filtering step following the formation of the nanoparticle aggregate. The reactive exterior polyvalent linkers may include a thiol reacting group. The reactive capping substituent may include a maleimide reacting group. The reactive capping substituent may include a vinyl sulfone reacting group as described herein. In embodiments, an exterior polyvalent linker having a thiol reacting group is reacted with a reactive capping substituent having a maleimide reacting group, thereby forming a thioether.

Reactive species (e.g. reactive polyvalent linkers, reactive capping substituent) include reactive functional groups such as those used in conjugate chemistry, including functional groups described herein, and embodiments thereof. In embodiments, the reactive group is one used in conjugate chemistry, for example, a thiol, a maleimide, a dienophile, amine, or aldehyde.

The method may be performed in the presence of a surfactant. The surfactant may be a non-ionic surfactant (e.g. Triton-X-100, PEG, Brij), a polysorbate surfactant (e.g. Tween-20), an anionic surfactant (e.g. sodium dodecyl sulfate (SDS), ammonium lauryl sulfate), or other amphiphilic compounds or copolymers including NP40 or pluronic. The surfactant may be Triton-X-100, a PEG, Tween-20, SDS, NP40 or pluronic. The surfactant may be Triton-X-100. The surfactant may be a PEG. The surfactant may be Tween-20. The surfactant may be SDS. The surfactant may be NP40. The surfactant may be pluronic.

The concentration of the surfactant may be about 0% to about 10%. The concentration of the surfactant may be about 0% to about 9%. The concentration of the surfactant may be about 0% to about 8%. The concentration of the surfactant may be about 0% to about 7%. The concentration of the surfactant may be about 0% to about 6%. The concentration of the surfactant may be about 0% to about 5%. The concentration of the surfactant may be about 0% to about 4%. The concentration of the surfactant may be about 0% to about 3%. The concentration of the surfactant may be about 0% to about 2%. The concentration of the surfactant may be about 0% to about 1%. The concentration of the surfactant may be about 0% to about 0.5%. The concentration of the surfactant may be about 0% to about 0.25%. The concentration of the surfactant may be about 0% to about 0.1%. The concentration of the surfactant may be about 0% to about 0.05%. The concentration of the surfactant may be about 0% to about 0.025%. The concentration of the surfactant may be about 0% to about 0.015%.

The concentration of the surfactant may be about 0.01% to about 10%. The concentration of the surfactant may be about 0.01% to about 9%. The concentration of the surfactant may be about 0.01% to about 8%. The concentration of the surfactant may be about 0.01% to about 7%. The concentration of the surfactant may be about 0.01% to about 6%. The concentration of the surfactant may be about 0.01% to about 5%. The concentration of the surfactant may be about 0.01% to about 4%. The concentration of the surfactant may be about 0.01% to about 3%. The concentration of the surfactant may be about 0.01% to about 2%. The concentration of the surfactant may be about 0.01% to about 1%. The concentration of the surfactant may be about 0.01% to about 0.5%. The concentration of the surfactant may be about 0.01% to about 0.25%. The concentration of the surfactant may be about 0.01% to about 0.1%. The concentration of the surfactant may be about 0.01% to about 0.05%. The concentration of the surfactant may be about 0.01% to about 0.025%. The concentration of the surfactant may be about 0.01% to about 0.015%.

The concentration of the surfactant may be about 10%. The concentration of the surfactant may be about 9%. The concentration of the surfactant may be about 8%. The concentration of the surfactant may be about 0 7%. The concentration of the surfactant may be about 0.01% 6%. The concentration of the surfactant may be about 0 5%. The concentration of the surfactant may be about 4%. The concentration of the surfactant may be about 3%. The concentration of the surfactant may be about 2%. The concentration of the surfactant may be about 1%. The concentration of the surfactant may be about 0.5%. The concentration of the surfactant may be about 0.25%. The concentration of the surfactant may be about 0.1%. The concentration of the surfactant may be about 0.05%. The concentration of the surfactant may be about 0.025%. The concentration of the surfactant may be about 0.015%. The concentration of the surfactant may be about 0.025%. The concentration of the surfactant may be about 0.015%. The concentration of the surfactant may be about 0.01%.

The reactive polyvalent linkers of the method include the polyvalent linkers as described herein, including embodiments thereof, wherein said polyvalent linkers are attached to a reactive group. The reactive group includes reactive groups described herein, including embodiments thereof. The reactive group may be, for example, a thiol. The reactive polyvalent linkers may be at a concentration of about 0.4 mM to about 3 mM. The concentration of the reactive polyvalent linkers may be about 0.4 mM to about 2.7 mM. The concentration of the reactive polyvalent linkers may be about 0.5 mM to about 2 mM. The concentration of the reactive polyvalent linkers may be about 0.5 mM to about 1.5 mM. The concentration of the reactive polyvalent linkers may be about 0.5 mM to about 1.2 mM. The concentration of the reactive polyvalent linkers may be about 0.5 mM to about 1 mM. The concentration of the reactive polyvalent linkers may be about 0.5 mM to about 0.7 mM.

The reactive polyvalent linkers may be at a concentration of about 0.1 mM to about 3 mM. The concentration of the reactive polyvalent linkers may be about 0.1 mM to about 2.7 mM. The concentration of the reactive polyvalent linkers may be about 0.1 mM to about 2 mM. The concentration of the reactive polyvalent linkers may be about 0.1 mM to about 1.5 mM. The concentration of the reactive polyvalent linkers may be about 0.1 mM to about 1.2 mM. The concentration of the reactive polyvalent linkers may be about 0.1 mM to about 1 mM. The concentration of the reactive polyvalent linkers may be about 0.1 mM to about 0.7 mM. The concentration of the reactive polyvalent linkers may be about 0.1 mM to about 0.5 mM. The concentration of the reactive polyvalent linkers may be about 0.1 mM to about 0.25 mM.

The reactive polyvalent linkers may be at a concentration of about 3 mM. The concentration of the reactive polyvalent linkers may be about 2.7 mM. The concentration of the reactive polyvalent linkers may be about 2 mM. The concentration of the reactive polyvalent linkers may be about 1.5 mM. The concentration of the reactive polyvalent linkers may be about 1.2 mM. The concentration of the reactive polyvalent linkers may be about 1 mM. The concentration of the reactive polyvalent linkers may be about 0.7 mM. The concentration of the reactive polyvalent linkers may be about 0.5 mM. The concentration of the reactive polyvalent linkers may be about 0.59 mM. The concentration of the reactive polyvalent linkers may be about 0.25 mM. The concentration of the reactive polyvalent linkers may be about 0.2 mM. The concentration of the reactive polyvalent linkers may be about 0.15 mM. The concentration of the reactive polyvalent linkers may be about 0.125 mM. The concentration of the reactive polyvalent linkers may be about 0.12 mM. The concentration of the reactive polyvalent linkers may be about 0.1 mM. The concentration of the reactive polyvalent linkers may be 0.05 mM. The concentration of the reactive polyvalent linkers may be 0.025 mM. The concentration of the reactive polyvalent linkers may be 0.02 mM. The concentration of the reactive polyvalent linkers may be 0.015 mM. The concentration of the reactive polyvalent linkers may be about 0.01.

The reactive linkers may include cleavage sites as described herein, including embodiments thereof. The cleavage site may be an ester (e.g. —C(O)O—). The ester may be recognized by an enzyme. The enzyme may be an esterase.

The reactive capping substituent of the method includes the capping substituents described herein, including embodiments thereof, wherein said capping substituent is attached to a reactive group thereby forming a reactive capping substituent. The reactive group includes reactive groups described herein, including embodiments thereof. The reactive capping substituent may be substituted or unsubstituted maleimide. The reactive capping substituent may be unsubstituted maleimide. The reactive capping substituent may be a substituted maleimide, wherein said maleimide is substituted with a capping functional group as described herein, including embodiments thereof. The reactive capping substituent may be N-phenyl substituted maleimide. The reactive capping substituent may be N-PEG substituted maleimide. In embodiments, the PEG may be substituted with a detectable moiety as described herein, including embodiments thereof. The detectable moiety may be fluorescein (e.g. fluorescein isothiocyanate (FITC)). The reactive capping substituent may be substituted or unsubstituted vinyl sulfone (e.g. -alkyl, -heteroalkyl, or -aryl vinyl sulfone). The vinyl-sulfone may be PEG substituted vinyl sulfone. The vinyl-sulfone may be vinyl sulfone substituted with FITC-PEG. In embodiments, the capping substituent renders the nanoparticle aggregate biocompatible (i.e. non-toxic to the subject).

In embodiments, the concentration of the nanoparticle cores is modulated. The concentration of the nanoparticle cores may be about $7.0 \times 10^{11}$ particles/mL to about $1.5 \times 10^{14}$ particles/mL. The concentration of the nanoparticle cores may be about $7.0 \times 10^{11}$ particles/mL to about $5.0 \times 10^{13}$ particles/mL. The concentration of the nanoparticle cores may be about $1.0 \times 10^{13}$ particles/mL to about $8.0 \times 10^{13}$ particles/mL. The concentration of the nanoparticle cores may be about $7.0 \times 10^{11}$ particles/mL. The concentration of nanoparticle cores may be about $5.7 \times 10^{12}$ particles/mL. The concentration of the nanoparticle cores may be about $5.0 \times 10^{13}$ particles/mL. The concentration of the nanoparticle cores may be about $1.5 \times 10^{14}$ particles/mL.

IV. Methods of Delivering or Administering a Nanoparticle Aggregate

In another aspect is a method of delivering a nanoparticle aggregate. The method includes administering a nanoparticle aggregate as described herein, including embodiments thereof, to a subject in need thereof. The subject may have a disease, such as cancer, as described herein.

Also provided herein are methods of delivering or administering a nanoparticle aggregate described herein. In one aspect, is a method of treating cancer in subject in need thereof. The method includes administering to the subject, a nanoparticle aggregate as described herein which includes a therapeutic moiety thereby treating the cancer in the subject in need thereof. The cancer may be a solid tumor cancer. The cancer may be melanoma, sarcoma, carcinoma, or lymphoma. The cancer may be breast cancer, prostate cancer, lung cancer, non-small cell lung cancer, liver cancer, kidney cancer, urinary bladder cancer, testicular cancer, thyroid cancer, esophageal cancer, endometrial cancer, uterine cancer, pancreatic cancer, ovarian cancer, head and neck cancer, cervical cancer, brain cancer, or colon cancer. The cancer may be breast cancer. The cancer may be prostate cancer. The cancer may be lung cancer. The cancer may be non-small cell lung cancer. The cancer may be liver cancer. The cancer may be kidney cancer. The cancer may be bladder cancer. The cancer may be testicular cancer. The cancer may be thyroid cancer. The cancer may be esophageal cancer. The cancer may be endometrial cancer. The cancer may be uterine cancer. The cancer may be pancreatic cancer. The cancer may be ovarian cancer. The cancer may be head and neck cancer. The cancer may be cervical cancer. The cancer may be brain cancer. The cancer may be colon cancer.

The therapeutic moiety may be an anti-cancer agent as described herein. The therapeutic moiety may be chemotherapeutic, a radiotherapy, or a therapeutic moiety used for thermal ablation.

In another aspect, is a method of detecting a solid tumor in a subject in need thereof. The method includes administering to a subject in need thereof, a nanoparticle aggregate as described herein which includes a detectable moiety thereby detecting the solid tumor in the subject in need thereof. The detectable moiety is as described herein, including embodiments thereof. The detectable moiety may be a radioisotope or radionuclide as described herein, a fluorophore as described herein, a Raman tag as described herein, or a MRI contrast agent as described herein. The methods described herein may be used for detecting (i.e diagnosing) a solid tumor cancer by allowing imagining of the size or location of the solid tumor cancer in the subject.

The nanoparticle cores of the delivered nanoparticle aggregates described in the methods are as described hereinabove in the "Compositions" section, including embodiments thereof. The nanoparticle cores may be gold. When the nanoparticle cores are gold, they may be used to detect the nanoparticle aggregate in a subject. The detection may be performed using techniques described herein, including for example, Raman Spectroscopy or MRI.

The nanoparticle aggregates of the methods may include nanoparticle linkers and capping linkers having cleavage sites. The cleavage sites are as described herein, including embodiments thereof. The method may include exposing the nanoparticle aggregates including nanoparticle linkers and capping linkers having cleavage sites to a cleavage agent. The cleavage agent may specifically cleave the nanoparticle aggregates at the cleavage sites, thereby releasing individual nanoparticle cores from the nanoparticle aggregate. The cleavage site may be an ester (e.g. —C(O)O—). The ester may be recognized by an enzyme. The enzyme may be an esterase. The individual nanoparticles may include a capping substituent having a capping functional group such as, for example, a therapeutic moiety or targeting moiety, as described herein, including embodiments thereof.

The nanoparticle aggregates of the methods may include capping substituents substituted with a capping functional group, wherein the capping functional group is as described herein, including embodiments thereof. The capping functional group may be a biological moiety, a targeting moiety, a therapeutic moiety, a water soluble polymer moiety, or a detectable moiety. The capping functional group may be a hydrophobic moiety or hydrophilic moiety. The targeting moiety may allow the nanoparticle aggregate to localize at a targeting site. The targeting site may be a tissue, or targeted cellular location. When the capping functional group is a therapeutic moiety, the therapeutic moiety treats cancer in the subject in need thereof. The cancer may be a solid tumor cancer as described herein. When the capping functional group is a detectable moiety, the detectable moiety may be used to detect the nanoparticle aggregate in the subject. The detectable moiety may allow imaging locations of body using techniques in the art such as MRI.

V. Examples

Gold nanoparticle aggregates are networks of discrete nanoparticles aggregated together in a controlled manner. Gold nanoparticle aggregates have been studied in many ex vivo applications including surface enhanced Raman scattering (SERS)[1], chemical probing of single cells[2], diagnostics[3]. The potential use of nanoparticle aggregates in such applications in vivo is of great interest.

Here we describe a method to synthesis modular, consistent and biocompatible nanoparticle aggregates from small discrete citrate stabilized gold nanoparticles. The modular synthesis of the gold nanoparticle aggregates described here allows for a variety of functional groups to be conjugated to the surface of the nanoparticle aggregate s. The nanoparticles described here are able to be synthesized readily and the modularity of the synthesis allows for the conjugation of various functional groups to the surface, including PEG for biocompatibility, n-phenylmaleimide for organic solubility, fluorophores for fluorescence and any other functional group conjugated to a thiol reactive species. Here we demonstrate that the size of the aggregate is dependent, in part, on synthesis conditions including initial particle concentration, surfactant type, and the concentration of a polyvalent linker, for example, pentaerythritol tetrakis (3-mercaptopropionate) (PTMP).

Particle Concentration Influences Aggregate Size

Under the reaction conditions described, nanoparticle aggregate size can be influenced by the initial concentration of particle. An increase in particle concentration of the 10 nm particles results in an increase in aggregate size (FIG. 1). The most concentrated particles, $1.5 \times 10^{14}$ particles/ml, resulted in an average aggregate size of 99.27±8.57 nm. Smaller aggregates (31.01±1.94 nm) can be synthesized by decreasing the concentration of the nanoparticle aggregates by a factor of 100. The number of free nanoparticles remaining after the aggregation decreases as the concentration increases, suggesting an increase in reaction efficiency.

Aggregates can be Synthesized in a Range of PTMP

A concentration of at least 0.012 mM PTMP was used to form the aggregates. Within a range of 0.12 mM to 1.2 mM the size of the aggregates can controlled from 60 nm to 120 nm. FIG. 17. The concentration of PTMP appears to, in part, play a role in controlling the final size of the nanoparticle aggregates.

Surfactant Type, but not Length of Surfactant Influence Aggregate Size

Figure 3:
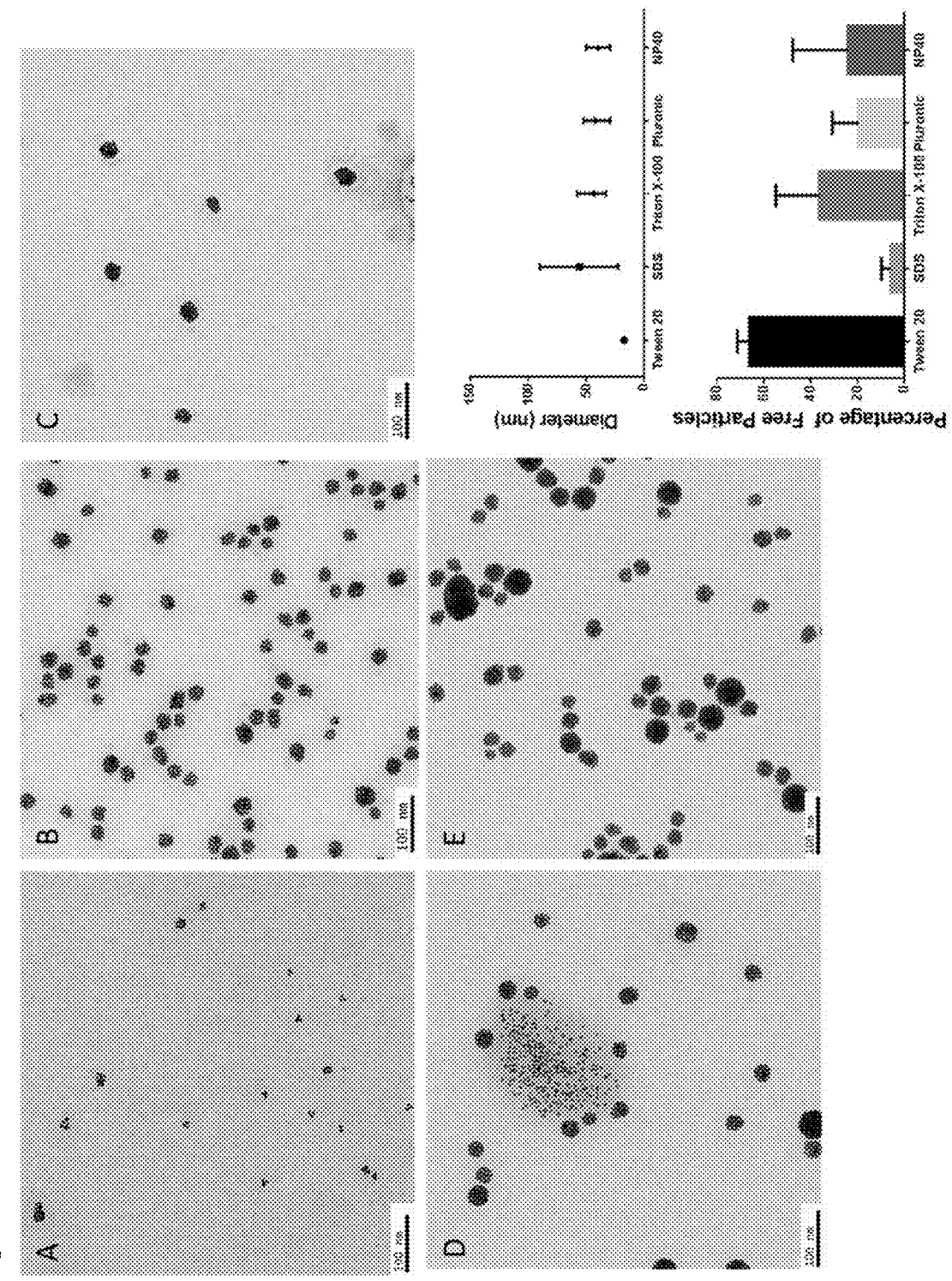
FIG. 3: Impact of surfactant on nanoparticle aggregate formation where A) shows use of 0.0133% solution of Tween 20; B) shows use of 0.0133% solution of SDS; C) shows use of 0.0133% solution of Triton-X-100; D) shows use of 0.0133% solution of Pluronic; E) shows use of 0.0133% solution of NP40; F) shows the average diameter; and G) shows the efficiency of the reaction.

The type of surfactant but not the size of the surfactant leads to differentially sized aggregates. Solutions of Tween20, TritonX100 and SDS used as surfactant lead to a smaller sized aggregates compared to the $PEG_{2000}$ solution (FIG. 3). Based on this result it was hypothesized that the size of the nanoparticle aggregates could be controlled via surfactant length. However, experiments using $PEG_{200}$ and $PEG_{8000}$ as surfactants showed similar aggregate sizes compared to $PEG_{2000}$, despite the change in surfactant length. Without being bound by any particular theory, it appears likely that the chemical characteristics of the chosen surfactants that Tween20, Triton X100, SDS, NP40, and pluronic are responsible for this result. All of the surfactants are amphiphilic and are used to create emulsions, which may partition limiting amounts of crosslinker and gold nanoparticles from the general solution resulting in a smaller aggregate size.

Figure 4:
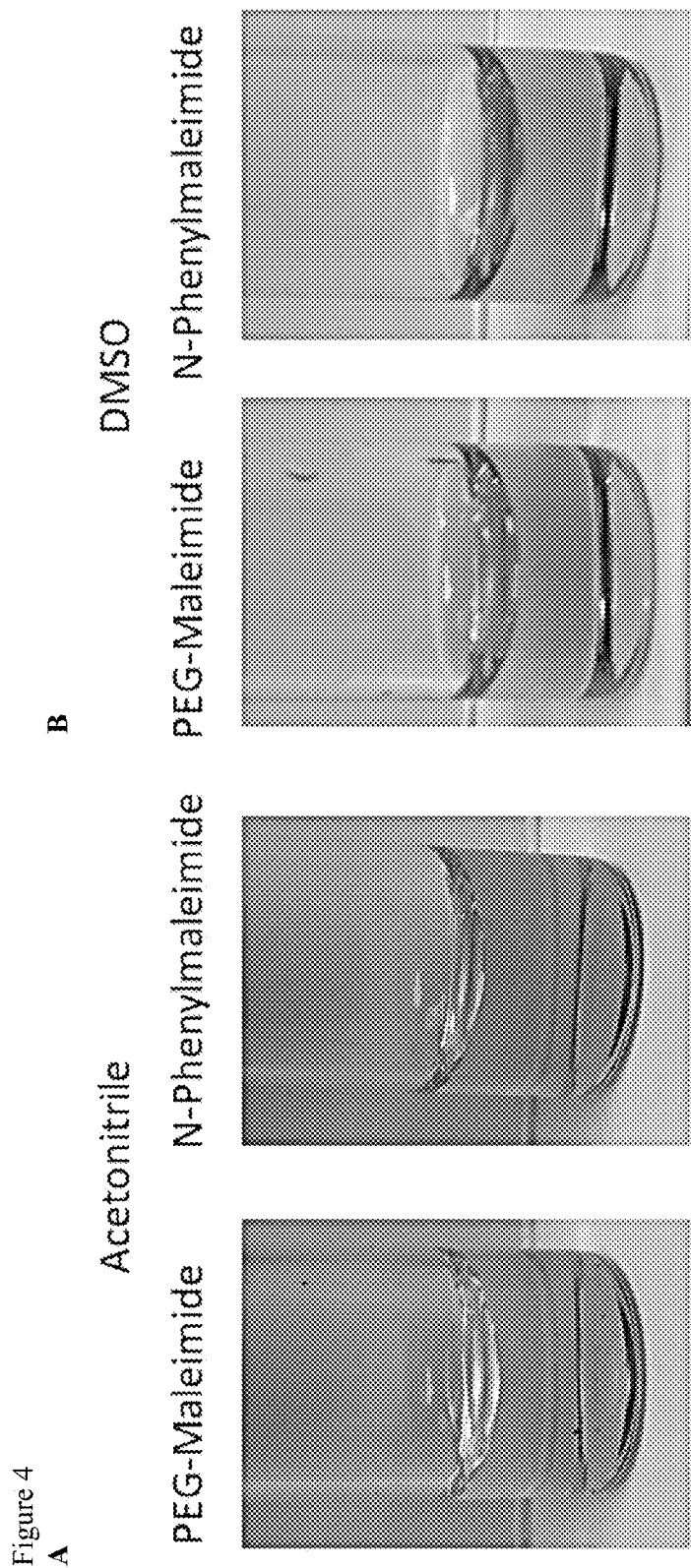
FIG. 4: Impact of capping substituent on nanoparticle aggregate formations where A) shows solubility of PEG-maleimide and phenylmaleimide in acetonitrile and B) shows solubility of PEG-maleimide and phenylmaleimide in DMSO.
Figure 5:
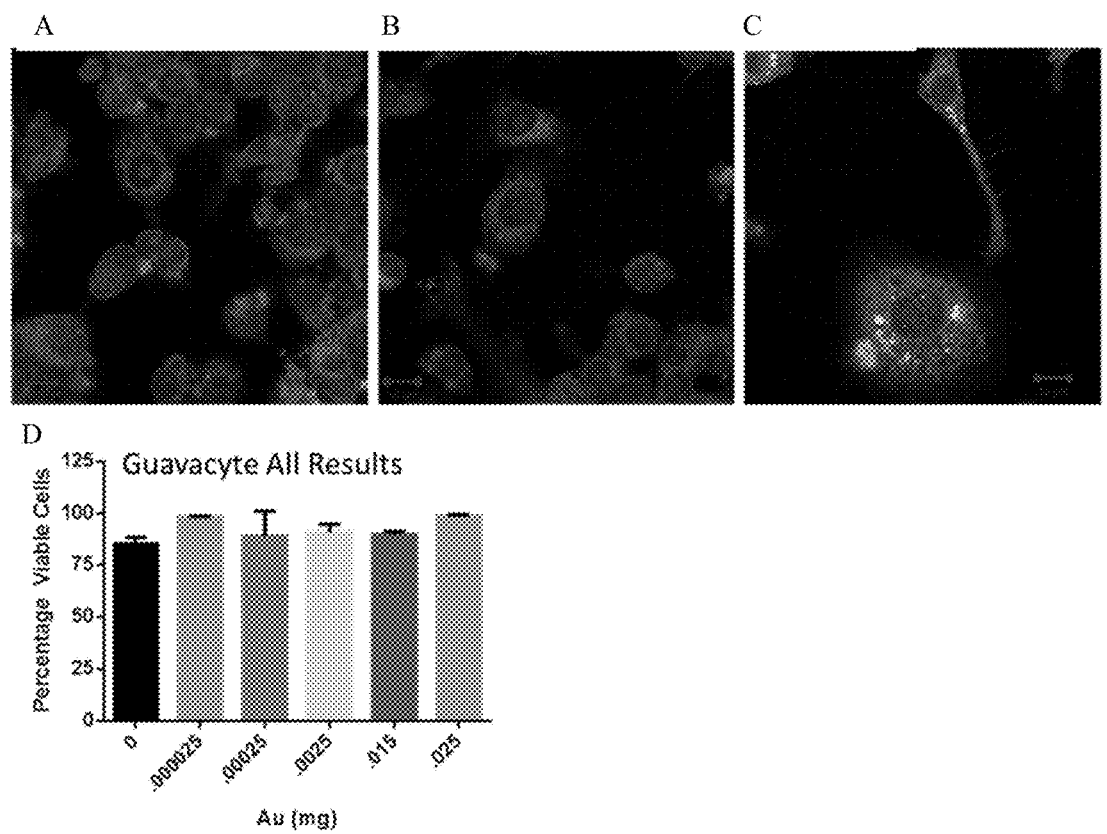
FIG. 5: N9 cells treated with increasing doses of FITC-PEG-Maleimide capped aggregates are taken up into N9 cells without influencing viability, where A) shows dose at 0.000025 mg Au; B) shows dose at 0.00025 mg Au; and C) shows dose at 0.025 mg Au(C).
Figure 6:
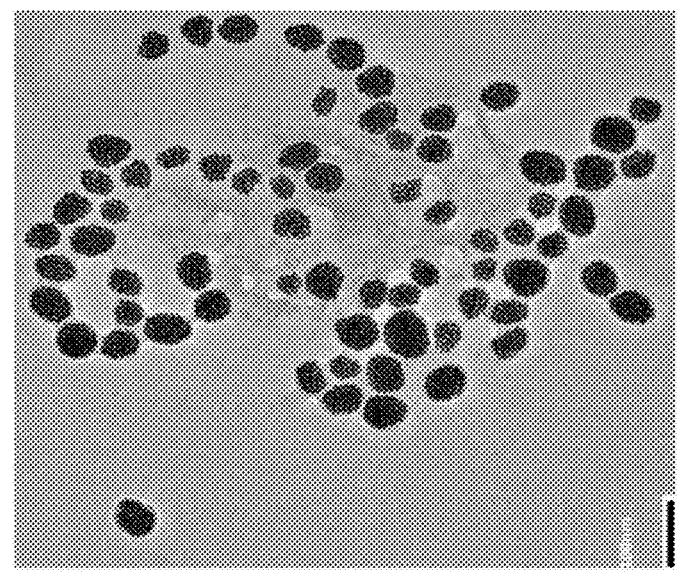
FIG. 6: Synthesis schemative of nanoparticle aggregates by crosslinking and capping.
Figure 6:
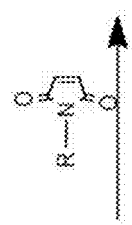
Figure 6:
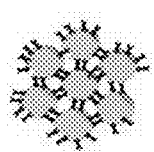
Figure 6:
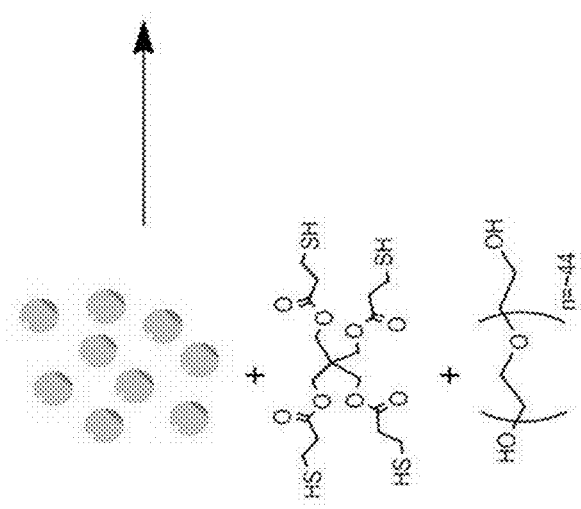
Figure 7:
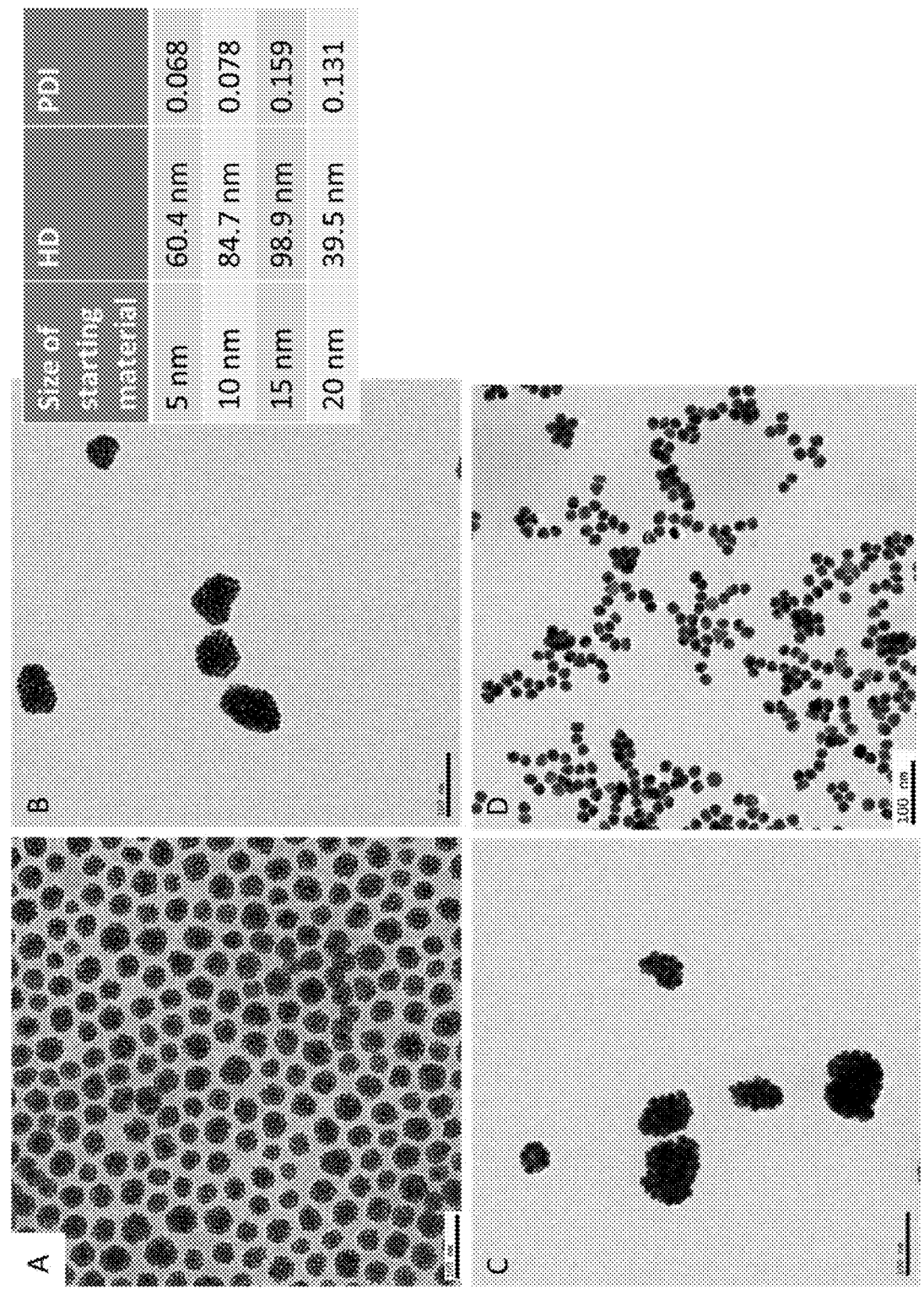
FIG. 7: Impact of nanoparticle core size on formation of nanoparticle aggregates where A) shows 5 nm particles; B) shows 10 nm particles; C) shows 15 nm particles; and D) shows 20 nm particles.
Figure 8A:
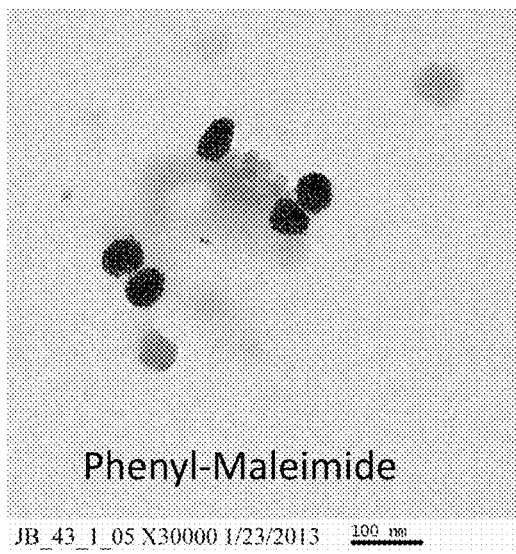
FIG. 8: Impact of capping substituent on formation of nanoparticle aggregates where A) shows phenyl-maleimide; B) shows PEG-maleimide; C) shows spectroscopic analysis of 5 nm nanoparticle cores forming nanoparticle aggregates capped with phenylmaleimide; D) shows solubility properties of the maleimide derivative capped nanoparticle aggregates; and E) shows the diameter of the maleimide derivative capped nanoparticle aggregates.
Figure 8B:
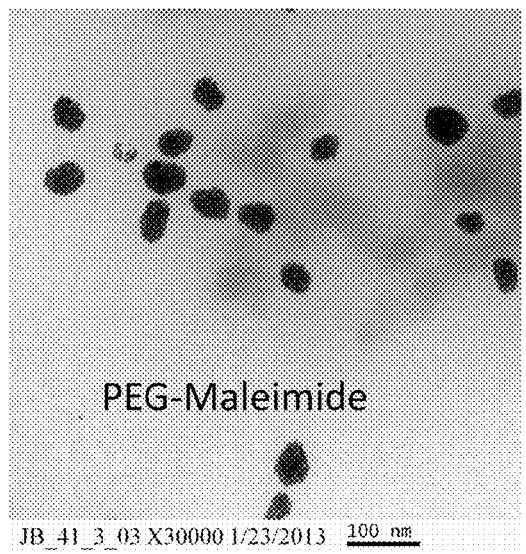
Figure 8C:
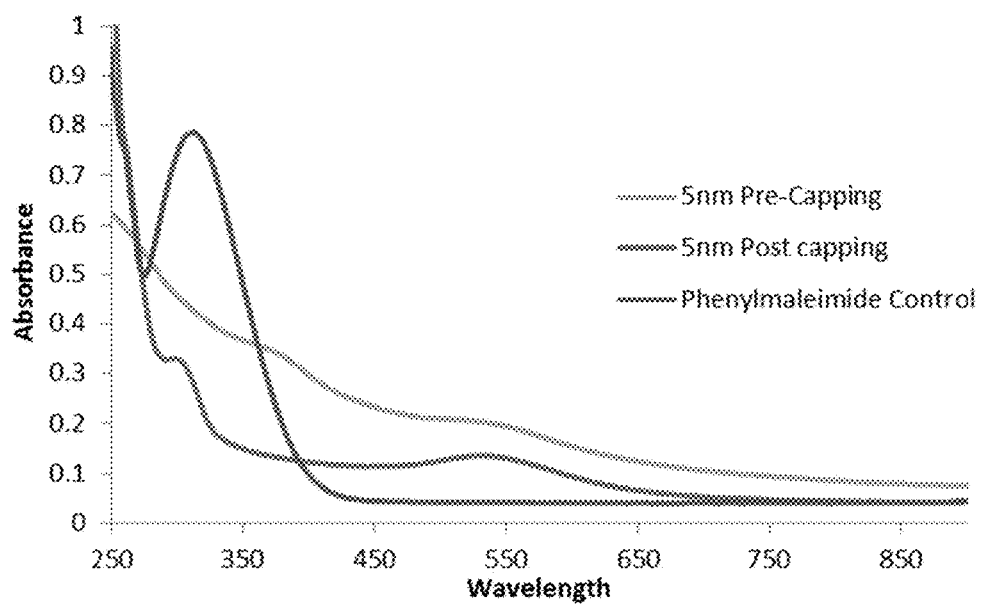
Figures 8D, 8E:
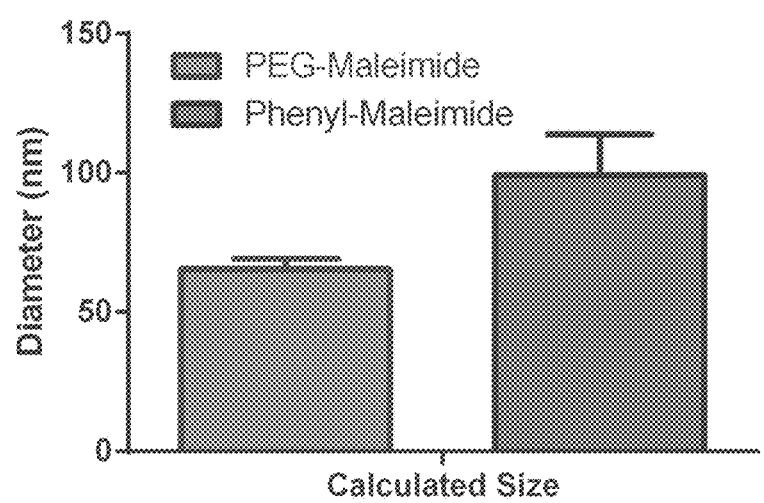
Figure 9:
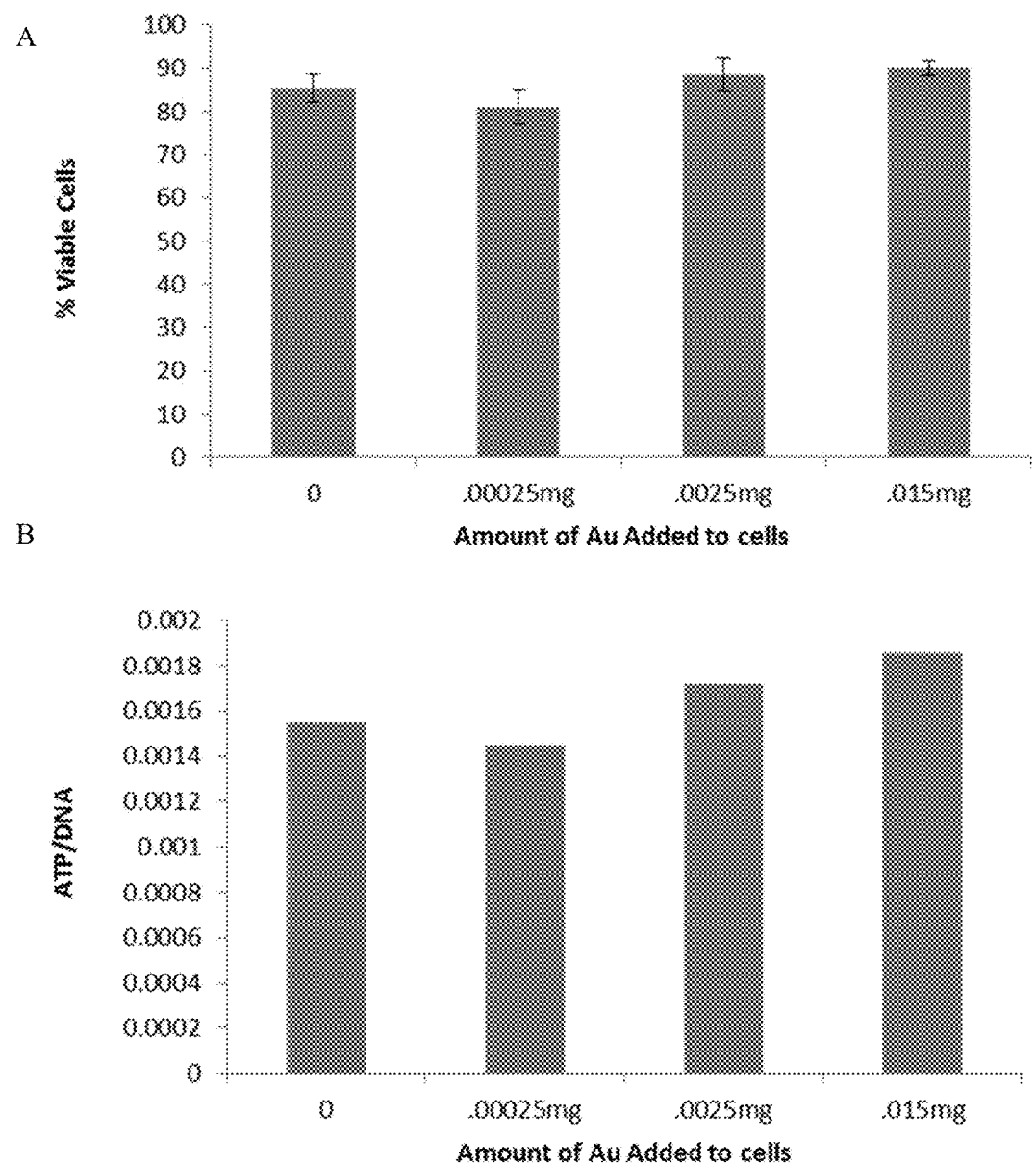
FIG. 9: Biocompatibility of PEG-maleimide capped nanoparticle aggregates where A) shows effect on cell viability and B) shows effect on ATP/DNA.
Figure 10:
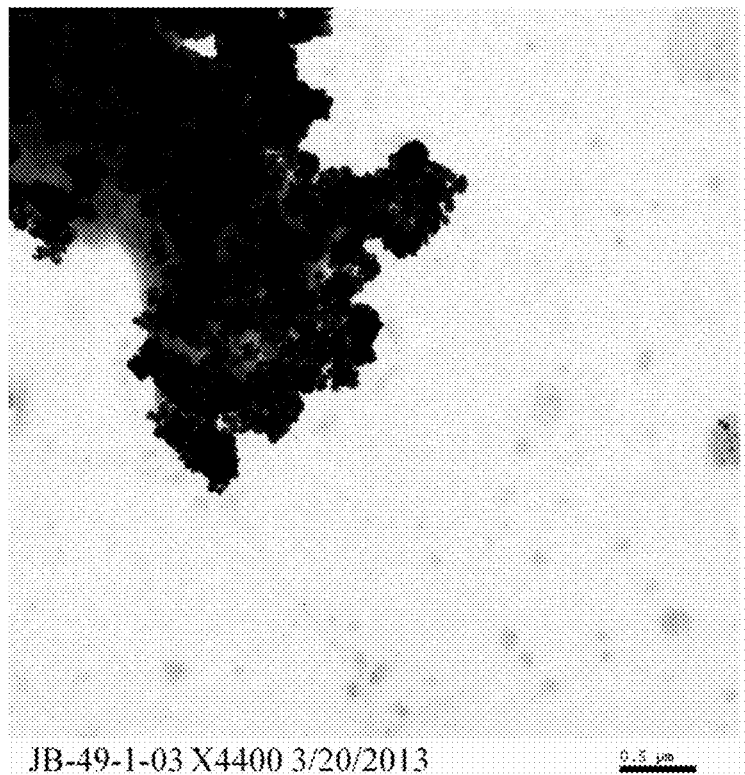
FIG. 10: Cleavage on nanoparticle aggregates having cleavage sites on both the nanoparticle linker and capping linker after exposure to base where A) is NaOH and B) is $NaHCO_3$.
Figure 10:
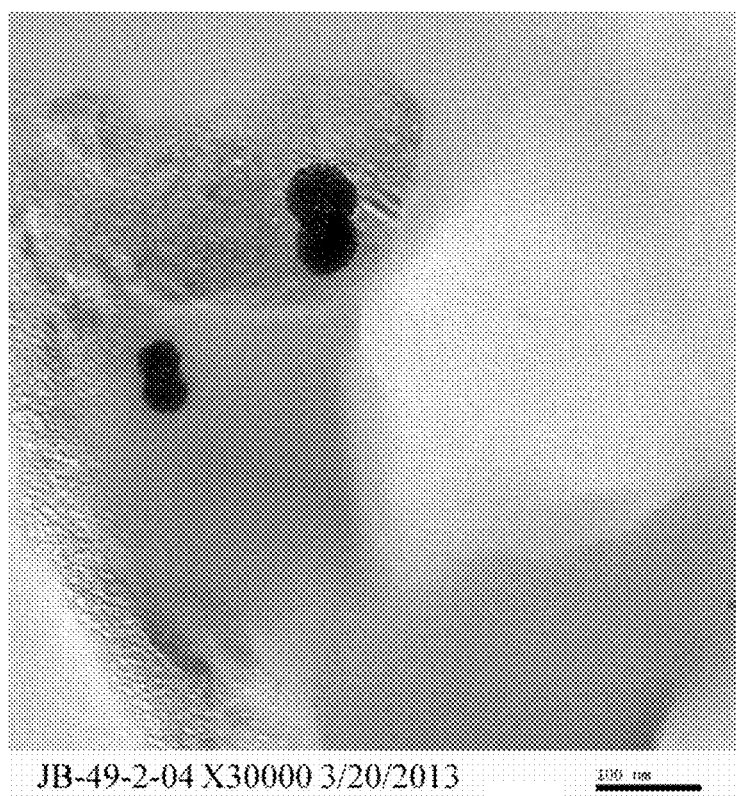
Figure 11:
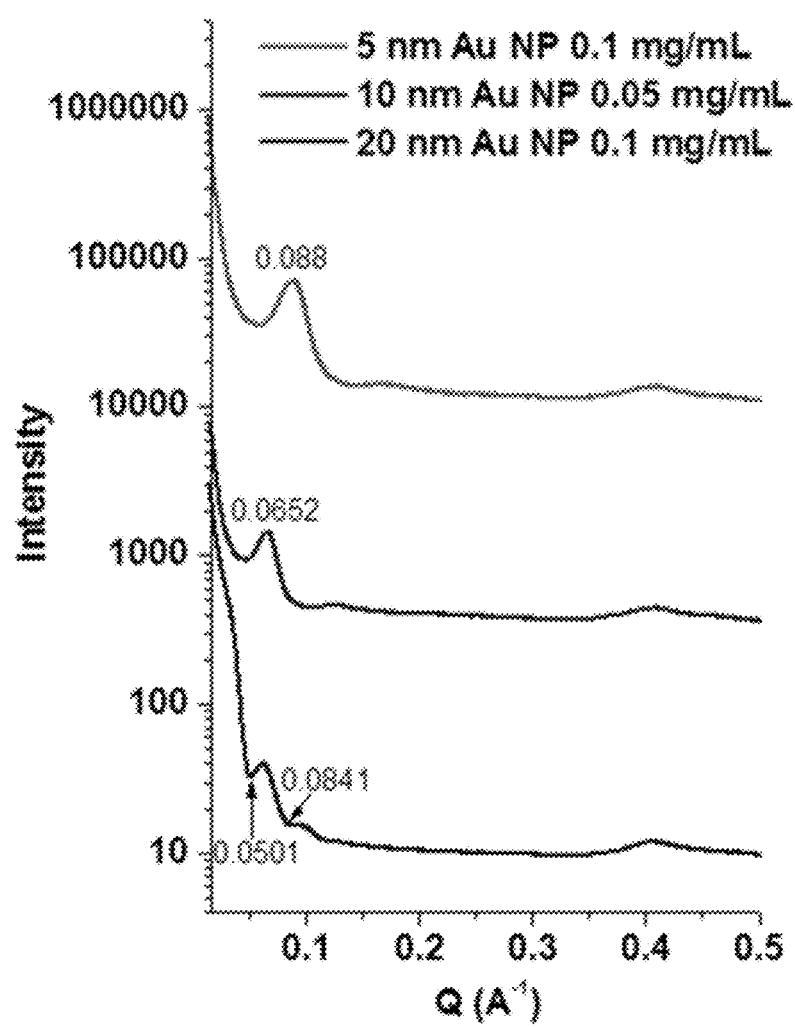
FIG. 11: SAXS results using differing Au nanoparticle cores.
Figure 12:
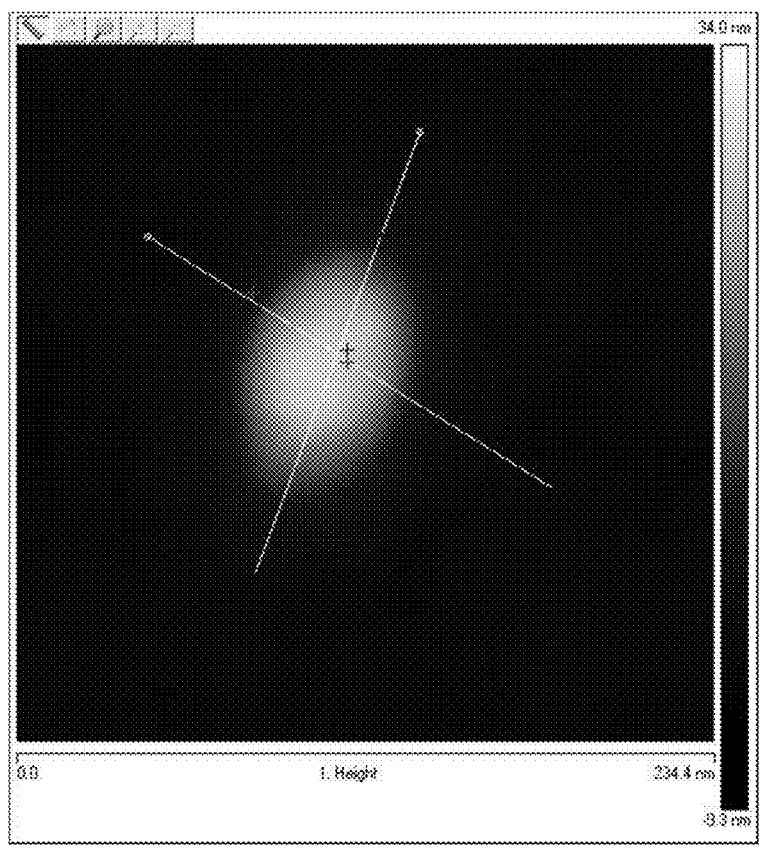
FIG. 12: A), B), and C) show AFM images taken on dried particles with width of ~81 nm and height of the aggregate about 30.7 nm.
Figure 12:
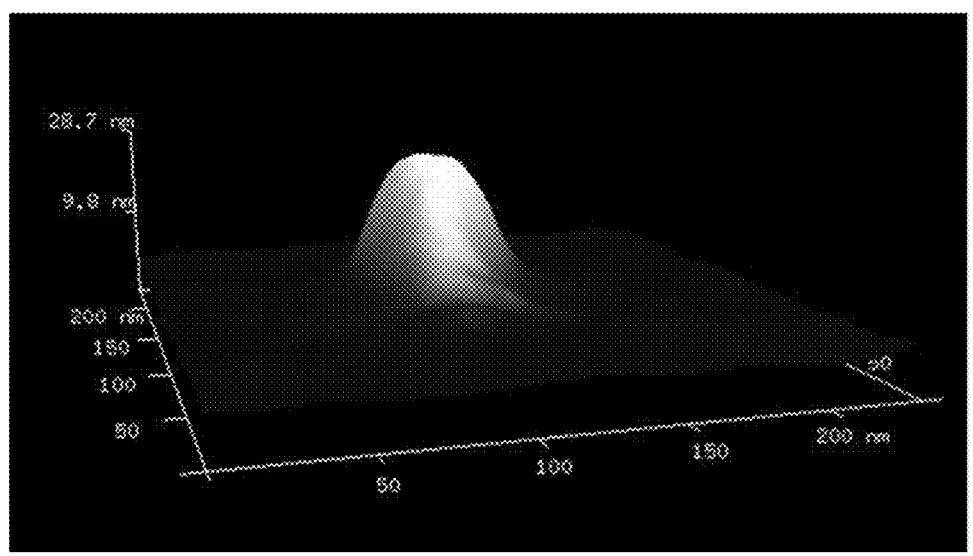
Figure 12:
Figure 13:
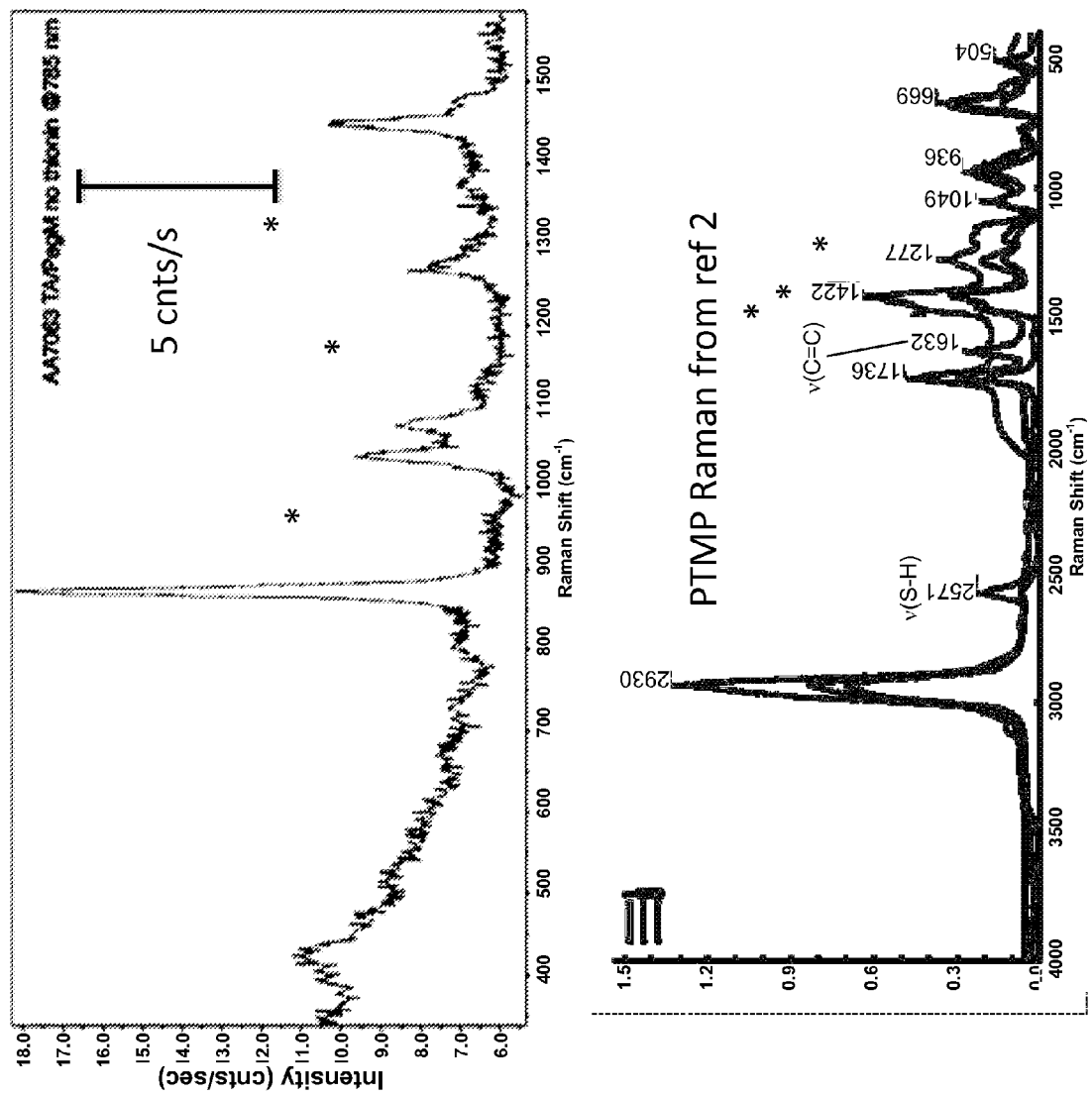
FIG. 13: SERS spectra from PTMP in aggregates, the reference 2 is Storha, A., Mun, E. A. & Khutoryanskiy, V. Synthesis of thiolated and acrylated nanoparticles using thiol-ene click chemistry: towards novel mucoadhesive materials for drug delivery. RSC Adv. (2013).
Figure 14:
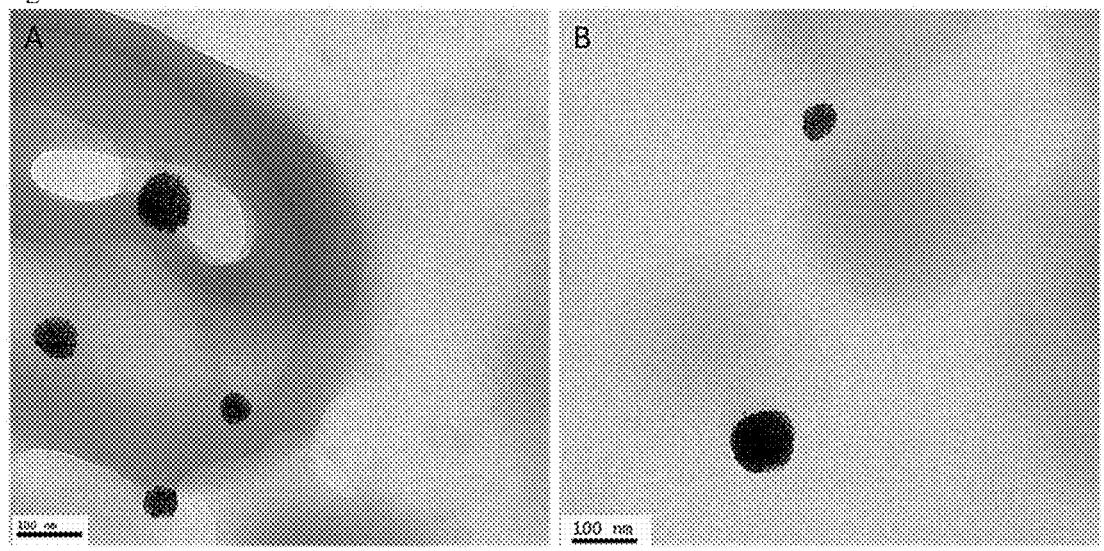
FIG. 14: Nanoparticle aggregates were conjugated to a targeting moiety, Folate, and a detection moiety FITC; particle size was determine by analyzing TEM images with Matlab; A) Folate+FITC+PEG; B) FITC+PEG Controls

The Capping Substituent of Nanoparticle Aggregates can Change their Characteristics Characteristics of the nanoparticle aggregates can be altered by changing the functional group conjugated to the nitrogen of the maleimide. Phenylmaleimide capped particles were soluble in methanol and slightly soluble in acetonitrile; while PEG-maleimide capped particles were soluble in water but soluble in neither methanol nor acetonitrile (FIG. 4). The change in the maleimide cap from PEG-maleimide to phenylmaleimide does not significantly alter the aggregate size. FITC-PEG-maleimide caps resulted in fluorescent nanoparticles that were able to be visualized using confocal microscopy in cellular studies (FIG. 5). Similar results were obtained using vinyl sulfone where a FITC-PEG-vinyl sulfone was used.

The ability to change the functionality of these nanoparticles is an important tool for broadening the potential uses of the nanoparticle aggregates. The nanoparticle aggregates herein can be used in organic and aqueous solvents depending on the capping agent used.

Nanoparticle Aggregates are Taken Up by Mouse Microglia/Macrophages and do not have an Effect on Cell Viability N9 cells treated with escalating doses of sterile filtered nanoparticle aggregates (FIG. 5) showed no change in cell metabolism nor in cell number compared to cells receiving no treatment. Nanoparticle aggregates capped with PEG-maleimide can be uptaken by N9 cells without influencing cell viability. Confocal microscopy images demonstrate that FITC-PEG-maleimide capped particles were taken up into N9 cells (FIG. 5).

The nanoparticle aggregates are found in the cytoplasm of the N9 cells, the bright punctuate regions in the cytoplasm, especially near the nucleus, suggests endosomal uptake of the nanoparticle aggregates. The spots in the nucleus suggest nuclear uptake as well.

The development of a modular and biocompatible nanoparticle aggregate represents an improvement over previous nanoparticle aggregates. The nanoparticle aggregate system discussed here opens the field to biomedical applications such as SERS. Biocompatible nanoparticle aggregates could be used in cell studies to highlight specific organelles[2] and multiplexing of these systems could allow for simultaneous identification of multiple cell types[8].

The modular synthesis of the nanoparticle aggregates allows for the use of these nanoparticle aggregates in a variety of functions including fluorescent cellular imaging, contrast imaging in vivo as well as a SERS substrate, via a maleimide attachment site. In particular, different thiol reactive agents could be used as a linker for the SERS analyte in order to modulate the distance between the analyte and the substrate in order to achieve the highest possible level of enhancement[9]. The consistent production of biocompatible nanoparticle aggregates will allow for the investigation of these nanoparticle aggregates as drug delivery vehicles or imaging agents[10].

Materials

All material was used as supplied. Citrate stabilized gold colloid suspension (5 nm, 10 nm, 15 nm and 20 nm) were purchased from Ted Pella. FITC-PEG-Maleimide were purchased from Nanocs. All other compounds were purchased from Sigma Aldrich. DAPI was purchased from Molecular Probes from Life technologies and DiI was purchased from Invitrogen.

Aggregate Synthesis

Actual Volumes:

Nanoparticle aggregates were synthesized by the dropwise addition of 250 µl of nanoparticles (5 nm AuNPs, 5e13 particles/ml) to a solution containing 58.1 µL of PTMP (4 mg/ml in ethanol), 5.3 µL of $PEG_{2000}$ (20 mg/ml in water), and 86.6 µl of $H_2O$. Additional syntheses were completed using 5.8 µL of PTMP (4 mg/ml in ethanol) and 52.3 µL of additional ethanol. Reaction vessels were shaken for two hours at room temperature and then were placed on the bench overnight.

Capping:

Nanoparticle aggregates were capped by the addition of 1.1 eq $PEG_{2000}$-Maleimide (20 mg/ml in water) for each mole of PTMP to the reaction vessel. After two hours of shaking at room temperature, the particles are centrifuged at 10,000 g for 10 minutes. The supernatant was removed and the particles were resuspended in 250 µl water.

Alternative Conditions for Testing

[PTMP] Variation:

As described above, at a concentration of at least 0.012 mM PTMP the nanoparticle aggregates form. The concentration range of PTMP between about 0.12 mM to 1.2 mM appears to control the particle size from 60 nm to 120 nm. FIG. 17. Initial reaction conditions described above were about 9 equivalents of crosslinker for each mole of PEG. To determine the dependence of aggregate size on crosslinker concentration 0.1, 1, 4.5, 9, and 20 equivalents of PTMP were tested. Nanoparticle aggregates were prepared as described above except the volume of crosslinker and water was varied to allow for a change in concentration of the crosslinker without changing the total reaction volume. For these experiments, 3 liquids were combined (as described above) the PTMP in ethanol, extra ethanol and particles in water. The extra ethanol was varied such that the total ethanol in the reaction from the PTMP and extra ethanol was held constant.

[Particle] Variation:

In order to determine the effect of particle concentration on the final aggregate size, 10 nm particles (5.7e12 particles) were concentrated or diluted to 4.5e10, 7e11, 5e13, or 1.5e14 particles/ml by centrifuging at 21,150 g for 30 minutes and removing the appropriate volume of supernatant to achieve 250 µl of particles at the specified concentration. Aggregates were synthesized as described above.

Surfactant Type Variation:

Particles were prepared as above, except in place of $PEG_{2000}$ 5.3 µL of 20 mg/ml solutions of the test surfactants (NP40, Pluronic, Triton X100, SDS, Tween20, $PEG_{200}$, $PEG_{1000}$, $PEG_{2000}$, $PEG_{8000}$) were added to the reaction vessel.

Capping Variation:

Nanoparticle aggregates were prepared as above except in lieu of $PEG_{2000}$-Maleimide, 1.1 eq for each mole of PTMP of maleimide caps (DOTA-$PEG_{2000}$-maleimide in water and N-Phenylmaleimide or N-4-bromophenylmaleimide in DMSO) were added to the reaction solution after the overnight incubation. To synthesize fluorescent particles, 10% of the capping solution was FITC-PEG-Maleimide and 90% was PEG-Maleimide. To prepare targeted particles, Folate-PEG-maleimide was used. N-Phenylmaleimide capped aggregates were resuspended in DMSO, other nanoparticle aggregates were resuspended in water.

Particle Characterization (Microscopy):

To determine the size of the metallic core of the aggregates 2 µl of aggregates solution were dried onto a 200 mesh carbon copper grid from TED Pella. TEM images were taken using FEI Tecnai 12 Twin. Images were analyzed using a Matlab program that found the edges of each aggregate/particle by identifying transitions in contrast in the TEM images and then calculated the area of each aggregate/particle in the image, the area was converted to diameter by assuming a circular shape of the aggregate/particle. The inefficiency of each reaction was determined by counting the number of free particles (defined as less than twice the single particle radius) and dividing by total events counted. Confocal images were taken on a Zeiss Inverted LSM510 META 2 photon microscope.

Particle Characterization

Particle composition was analyzed by both inductively coupled plasma mass spectrometry (ICP-MS) and by thermogravimetric analysis (TGA). Hydrodynamic diameter was determined by dynamic light scattering (DLS).

For TGA analysis, 20 mL of capped gold aggregates were concentrated by centrifugation. Particles were dried in the platinum sample holder under vacuum at 95° C. for 1 h. The sample was loaded into the TGA and the sample was heated from 20° C. to 900° C., at a rate of 20° C./minute.

Cell Growth and Viability Experiments:

N9 cells were cultured in DMEM media supplemented with 10% FBS, 1% Penicillin and streptomycin, 1% HEPES buffer and Plasmocin™. N9 cells were grown until 80% confluent then treated with escalating does of gold nanoparticle aggregates (5 µl gold solution and 100 µl fresh growth media). After a 24-hour treatment with particles, the media was removed, the cells were washed twice with PBS to remove free gold nanoparticle aggregates and then the cells were returned to serum containing media for 2 hours before the viability test. Two complementary assays were performed in order to ensure accuracy of the measurement. The first assay from Quava Technologies uses a proprietary Quava ViaCount Reagent that contains two fluorescent dyes, one dye is membrane permeant, it will stain all cells, and the second dye is membrane impermeable, only staining damaged cells (Product Literature). The cell count and cell viability were determined using flow cytometry. In the second assay, metabolic activity was measured by measuring the luminescence that results as the CellTiter-Glo® Substrate is converted into a luminescent substrate by ATP in cell lysate11. To normalize to cell number the amount of double stranded DNA was measured by the fluorescence of PicoGreen® reagent. PicoGreen reagent fluoresces upon binding to double stranded DNA.

REFERENCES 1. (a) Hossain, M. K.; Kitahama, Y.; Huang, G. G.; Kaneko, T.; Ozaki, Y., SPR and SERS characteristics of gold nanoparticle aggregates with different morphologies. Appl. Phys. B 2008, 93 (1), 165-170; (b) Schwartzberg, A. M.; Grant, C. D.; Wolcott, A.; Talley, C. E.; Huser, T. R.; Bogomolni, R.; Zhang, J. Z., Unique Gold Nanoparticle Aggregates as a Highly Active Surface-Enhanced Raman Scattering Substrate. The Journal of Physical Chemistry B 2004, 108 (50), 19191-19197.
2. Kneipp, J.; Kneipp, H.; McLaughlin, M.; Brown, D.; Kneipp, K., In vivo molecular probing of cellular compartments with gold nanoparticles and nanoparticle aggregate s. Nano Lett 2006, 6 (10), 2225-31.
3. Lee, K.; Drachev, V. P.; Irudayaraj, J., DNA-Gold Nanoparticle Reversible Networks Grown on Cell Surface Marker Sites: Application in Diagnostics. ACS Nano 2011, 5 (3), 2109-2117.
4. Boal, A. K.; Ilhan, F.; DeRouchey, J. E.; Thurn-Albrecht, T.; Russell, T. P.; Rotello, V. M., Self-assembly of nanoparticles into structured spherical and network aggregates. Nature 2000, 404 (6779), 746-748.
5. Storhoff, J. J.; Lazarides, A. A.; Mucic, R. C.; Mirkin, C. A.; Letsinger, R. L.; Schatz, G. C., What Controls the Optical Properties of DNA-Linked Gold Nanoparticle Assemblies? Journal of the American Chemical Society 2000, 122 (19), 4640-4650.
6. Klajn, R.; Bishop, K. J. M.; Fialkowski, M.; Paszewski, M.; Campbell, C. J.; Gray, T. P.; Grzybowski, B. A., Plastic and Moldable Metals by Self-Assembly of Sticky Nanoparticle Aggregates. Science 2007, 316 (5822), 261-264.
7. Hussain, I.; Wang, Z.; Cooper, A. I.; Brust, M., Formation of Spherical Nanostructures by the Controlled Aggregation of Gold Colloids. Langmuir 2006, 22 (7), 2938-2941.
8. Keren, S.; Zavaleta, C.; Cheng, Z.; de la Zerda, A.; Gheysens, O.; Gambhir, S. S., Noninvasive molecular imaging of small living subjects using Raman spectroscopy. Proceedings of the National Academy of Sciences 2008, 105 (15), 5844-5849.
9. Stiles, P. L.; Dieringer, J. A.; Shah, N. C.; Van Duyne, R. P., Surface-Enhanced Raman Spectroscopy. Annual Review of Analytical Chemistry 2008, 1 (1), 601-626.
10. Tam, J. M.; Tam, J. O.; Murthy, A.; Ingram, D. R.; Ma, L. L.; Travis, K.; Johnston, K. P.; Sokolov, K. V., Controlled Assembly of Biodegradable Plasmonic Nanoclusters for Near-Infrared Imaging and Therapeutic Applications. ACS Nano 2010, 4 (4), 2178-2184.
11. Niles, A. L.; Moravec, R. A.; Riss, T. L., In vitro viability and cytotoxicity testing and same-well multi-parametric combinations for high throughput screening. Current chemical genomics 2009, 3, 33-41.
12. Science, 277, 1997, p 1078.
13. J. Am. Chem. Soc., 2000, 122, pp 4640-4650.
14. Langmuir, 2006, 22, pp 2938-2941.
15. Science, 316 13 Apr. 2007, p 261.
16. J. Am. Chem. Soc., 2005, 127, pp 1519-1529.
17. Nature, 404, 13 Apr. 2000, p 746.

What is claimed is:
1. A nanoparticle aggregate comprising:
(i) a plurality of interior nanoparticle cores covalently bound together and enclosed by a plurality of exterior nanoparticle cores covalently bound together, wherein at least a portion of said plurality of interior nanoparticle cores are covalently bound to said plurality of exterior nanoparticle cores;
(ii) a plurality of interior polyvalent linkers covalently binding said interior nanoparticle cores together, covalently binding said exterior nanoparticle cores together, and covalently binding said portion of said interior nanoparticle cores to said exterior nanoparticle cores, wherein each of said plurality of interior polyvalent linkers comprises a central polyvalent moiety covalently bound to at least two nanoparticle linkers, each of said nanoparticle linkers covalently bound to one of said interior nanoparticle cores or one of said exterior nanoparticle cores, and wherein said plurality of interior polyvalent linkers do not bind a capping substituent to said interior nanoparticle cores;
(iii) a plurality of exterior polyvalent linkers covalently binding at least one capping substituent to said exterior nanoparticle cores, wherein each of said plurality of exterior polyvalent linkers comprises:
  (a) said central polyvalent moiety covalently bound to at least one of said nanoparticle linkers, said nanoparticle linkers covalently bound to one of said exterior nanoparticle cores; and
  (b) at least one capping linker covalently bound to said capping substituent, wherein said plurality of exterior polyvalent linkers comprise at least two nanoparticle linkers and capping linkers combined;
wherein the plurality of interior nanoparticle cores and the plurality of exterior nanoparticle cores are each independently titanium, zirconium, gold, silver, platinum, cerium, arsenic, iron, aluminum, carbon, boron, cadmium, selenium, zinc, silicon, or a metal oxide of any one of the foregoing; and
wherein the nanoparticle linker and the capping linker are each independently —C(O)—, —C(O)O—, —O—, —S—, —NH—, —NR$^1$—, —C(O)NR$^2$—, —S(O)$_n$—, —S(O)NR$^3$—, —OP(O)(OR$^4$)O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, an amino acid sequence, or a nucleic acid sequence;
R$^1$, R$^2$, R$^3$, R$^4$, are independently hydrogen, halogen, —N$_3$, —NO$_2$, —CF$_3$, —CCl$_3$, —CBr$_3$, —CI$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —OCH$_3$, —NHCNHNH$_2$, substituted or unsubstituted alkyl, substituted or unsubstituted heteroalkyl, substituted or unsubstituted cycloalkyl, sub- stituted or unsubstituted heterocycloalkyl, substituted or unsubstituted aryl, or substituted or unsubstituted heteroaryl; and n is 1 or 2.

2. The nanoparticle aggregate of claim 1, wherein said plurality of interior nanoparticle cores and said plurality of exterior nanoparticle cores are chemically identical.

3. The nanoparticle aggregate of claim 2, wherein said plurality of interior nanoparticle cores and said plurality of exterior nanoparticle cores comprise gold, silver, or platinum.

4. The nanoparticle aggregate of claim 1, wherein said plurality of exterior nanoparticle cores and said plurality of interior nanoparticle cores are about 2 to about 20 nm in diameter.

5. The nanoparticle aggregate of claim 1, wherein said nanoparticle linker is —C(O)—, —C(O)O—, —O—, —S—, —NH—, —NR$^1$—, —C(O)NR$^2$—, —S(O)$_n$—, —S(O)NR$^3$—, —OP(O)(OR$^4$)O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

R$^1$, R$^2$, R$^3$, R$^4$, are independently hydrogen, halogen, —N$_3$, —NO$_2$, —CF$_3$, —CCl$_3$, —CBr$_3$, —Cl$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —OCH$_3$, —NHCNHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n is 1 or 2.

6. The nanoparticle aggregate of claim 1, wherein said capping linker is —C(O)—, —C(O)O—, —O—, —S—, —NH—, —NR$^1$—, —C(O)NR$^2$—, —S(O)$_n$—, —S(O)NR$^3$—, —OP(O)(OR$^4$)O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

R$^1$, R$^2$, R$^3$, R$^4$, are independently hydrogen, halogen, —N$_3$, —NO$_2$, —CF$_3$, —CCl$_3$, —CBr$_3$, —Cl$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —OCH$_3$, —NHCNHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n is 1 or 2.

7. The nanoparticle aggregate of claim 1, wherein said plurality of exterior polyvalent linkers comprise at least three nanoparticle linkers and capping linkers combined.

8. The nanoparticle aggregate of claim 1, wherein said nanoparticle linker comprises a nanoparticle linker-cleavage site and wherein said capping linker comprises a capping linker-cleavage site.

9. The nanoparticle aggregate of claim 8, wherein said nanoparticle linker-cleavage site and said capping linker-cleavage site are independently an ester that is recognized by an esterase.

10. The nanoparticle aggregate of claim 1, wherein said capping substituent is substituted with a capping functional group, said capping functional group comprising a hydrophobic moiety, a hydrophilic moiety, a biological moiety, a therapeutic moiety, a targeting moiety, a water soluble polymer moiety, or a detectable moiety.

11. The nanoparticle aggregate of claim 1, wherein said nanoparticle aggregate is about 50 nm in diameter.

12. A method for preparing a nanoparticle aggregate of claim 1, said method comprising:

(i) contacting a plurality of nanoparticle cores with a first plurality of reactive polyvalent linkers thereby forming a plurality of polyvalent linkers covalently binding said nanoparticle cores together, wherein a first portion of said plurality of nanoparticle cores are covalently bound to together to form a plurality of interior nanoparticle cores and a second portion of said plurality of nanoparticle cores are covalently bound together to form a plurality of exterior nanoparticle cores enclosing said plurality of interior nanoparticle cores, wherein said plurality of exterior nanoparticle cores are covalently bound to a portion of said plurality of interior nanoparticle cores;

(ii) allowing a portion of said plurality of reactive polyvalent linkers to react with a portion of said exterior nanoparticle cores thereby forming a plurality of reactive exterior polyvalent linkers covalently bound to said portion of said plurality of exterior nanoparticle cores;

(iii) contacting said nanoparticle aggregate with a reactive capping substituent and allowing said reactive capping substituent to react with said plurality of reactive exterior polyvalent linkers thereby forming said nanoparticle aggregate.

13. The method of claim 12, wherein step (i), (ii) or (iii) is performed in the presence of a surfactant.

14. The method of claim 12, wherein said reactive polyvalent linkers are at a concentration of about 0.01 mM to about 2.7 mM combined.

15. A method of treating cancer in a subject in need thereof, said method comprising administering a nanoparticle aggregate of claim 1, wherein said nanoparticle aggregate comprises a therapeutic moiety to treat said cancer in said subject in need thereof.

16. The method of claim 15, wherein said cancer is melanoma, sarcoma, carcinoma, lymphoma, breast cancer, prostate cancer, lung cancer, non-small cell lung cancer, liver cancer, kidney cancer, urinary bladder cancer, testicular cancer, thyroid cancer, esophageal cancer, endometrial cancer, uterine cancer, pancreatic cancer, ovarian cancer, head and neck cancer, cervical cancer, brain cancer, or colon cancer.

17. The method of claim 15, wherein said therapeutic moiety is an anti-cancer agent.

18. A method of detecting a solid tumor in a subject in need thereof, said method comprising administering a nanoparticle aggregate of claim 1, wherein said nanoparticle aggregate comprises a detectable moiety to detect said solid tumor in said subject in need thereof.

19. The method of claim 18, wherein said detectable moiety is a fluorophore, a radionuclide, a radioisotope, a Raman tag, or an MRI contrast agent.

20. The method of claim 18, wherein said nanoparticle aggregate further comprises a targeting moiety.

* * * * *